(12) United States Patent
Tang et al.

(10) Patent No.: US 9,929,363 B2
(45) Date of Patent: Mar. 27, 2018

(54) COMPOSITION AND SYNTHESIS OF AGGREGATION-INDUCED EMISSION MATERIALS

(71) Applicant: THE HONG KONG UNIVERSITY OF SCIENCE AND TECHNOLOGY, Hong Kong (CN)

(72) Inventors: Benzhong Tang, Hong Kong (CN); Ni Xie, Hong Kong (CN); Wing Yip Lam, Hong Kong (CN)

(73) Assignee: THE HONG KONG UNIVERSITY OF SCIENCE AND TECHNOLOGY, Hong Kong (CN)

( * ) Notice: Subject to any disclaimer, the term of this patent is extended or adjusted under 35 U.S.C. 154(b) by 0 days.

(21) Appl. No.: 14/908,341

(22) PCT Filed: Aug. 5, 2014

(86) PCT No.: PCT/CN2014/083719
§ 371 (c)(1),
(2) Date: Jan. 28, 2016

(87) PCT Pub. No.: WO2015/018322
PCT Pub. Date: Feb. 12, 2015

(65) Prior Publication Data
US 2016/0211470 A1 Jul. 21, 2016

Related U.S. Application Data

(60) Provisional application No. 61/958,746, filed on Aug. 5, 2013.

(51) Int. Cl.
| | |
|---|---|
| C07D 307/91 | (2006.01) |
| C07D 333/76 | (2006.01) |
| C07C 13/54 | (2006.01) |
| C09B 62/343 | (2006.01) |
| G01N 21/64 | (2006.01) |
| H01L 51/00 | (2006.01) |
| C07D 407/06 | (2006.01) |
| C07D 409/06 | (2006.01) |
| C07C 15/18 | (2006.01) |
| C07F 9/58 | (2006.01) |
| C09K 11/06 | (2006.01) |
| C09K 11/07 | (2006.01) |
| G01N 33/483 | (2006.01) |
| C09B 23/10 | (2006.01) |
| C09B 23/14 | (2006.01) |
| C09B 57/00 | (2006.01) |
| H01L 51/50 | (2006.01) |

(52) U.S. Cl.
CPC .......... *H01L 51/0091* (2013.01); *C07C 13/54* (2013.01); *C07C 15/18* (2013.01); *C07D 307/91* (2013.01); *C07D 333/76* (2013.01); *C07D 407/06* (2013.01); *C07D 409/06* (2013.01); *C07F 9/581* (2013.01); *C09B 23/105* (2013.01); *C09B 23/148* (2013.01); *C09B 57/00* (2013.01); *C09B 57/008* (2013.01); *C09K 11/06* (2013.01); *C09K 11/07* (2013.01); *G01N 33/4833* (2013.01); *H01L 51/005* (2013.01); *H01L 51/0058* (2013.01); *H01L 51/0061* (2013.01); *H01L 51/0073* (2013.01); *H01L 51/0074* (2013.01); *C09K 2211/1007* (2013.01); *C09K 2211/1011* (2013.01); *C09K 2211/1014* (2013.01); *C09K 2211/1029* (2013.01); *C09K 2211/1088* (2013.01); *C09K 2211/1092* (2013.01); *C09K 2211/188* (2013.01); *H01L 51/5012* (2013.01)

(58) Field of Classification Search
None
See application file for complete search history.

(56) References Cited

U.S. PATENT DOCUMENTS

2012/0237964 A1  9/2012  Tang et al.

FOREIGN PATENT DOCUMENTS

JP           03006570 A   *   1/1991

OTHER PUBLICATIONS

Yang Liu et al. "Enlarged tetrasubstituted alkenes with enhanced thermal and optoelectronic properties" Chem. Commun., vol. 49, Jul. 3, 2013 (Jul. 3, 2013), pp. 7216-7218.
Roman Popielarz et al. "Radical Ions in Photochemistry. Carbon-Carbon Bond Cleavage of Radical Cations in Solution: Theory and Application" J.Am.Chem.Soc., vol. 112, Dec. 31, 1990 (Dec. 31, 1990), pp. 3068-3082.
Yang Liu et al. "Systemic Studies of Tetraphenylethene-Triphenylamine Oligomers and a Polymer: Achieving Both Efficient Solid-State Emissions and Hole-Transporting Capability" Chem. Eur.J, No. 18, Dec. 31, 2012 (Dec. 31, 2012), pp. 9929-9938.
Lutz M. Engelhardt et al. "Lewis-Base Adducts of Group 11 metal(I) compounds.LI. Synthesis and Structural Characterization of Mononuclear Chloro-, Bromo- and Iodopyridinebis(triphenylphosphine)copper(I) Complexes" Aust. J.Chem., vol. 42, Dec. 31, 1989 (Dec. 31, 1989), pp. 895-905.
Takanori Suzuki et al. "Biphenyl-type electron acceptors exhibiting dynamic redox properties: a novel electrochromic system with 'write protect' option" Chem.Commun., Dec. 31, 1998 (Dec. 31, 1998), pp. 1331-1332.
S. H. Doss et al. "Carbenadibenzocycloheptane: Steady-State and Time-Resolved Spectroscopic Laser Studies" J. Org. Chem., vol. 52, Dec. 31, 1987 (Dec. 31, 1987), pp. 434-438.
ISR issued in International application No. PCT/CN2014/083719 dated Nov. 15, 2014.

* cited by examiner

*Primary Examiner* — Zinna Northington-Davis
(74) *Attorney, Agent, or Firm* — Nath, Goldberg & Meyer; Joshua B. Goldberg; Stanley N. Protigal

(57) ABSTRACT

The present subject matter relates to compositions containing and synthesis of fluorescent materials e made from tetraphenylethylene (TPE) derivative compounds exhibiting aggregation induced emission (AIE) properties. Further contemplated herein are applications for TPE derivative compounds such as electroluminescent devices since they have a high efficiency, low turn on voltage, and excellent brightness. Additionally, application of TPE derivatives exhibiting AIE properties in various fields such as OLEDs, fingerprinting and forensic technology, and various other biological and industrial sectors are discussed.

18 Claims, 23 Drawing Sheets

FIG. 4A
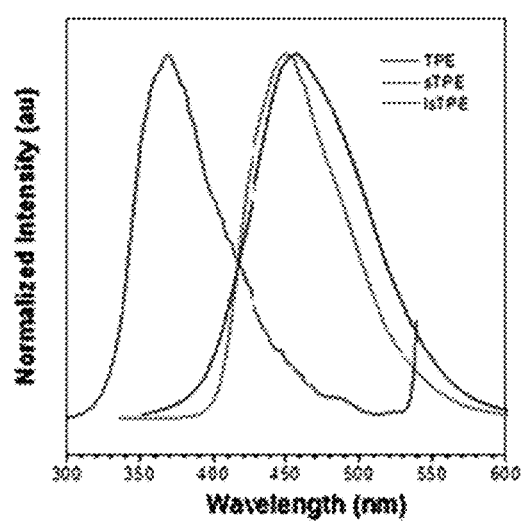
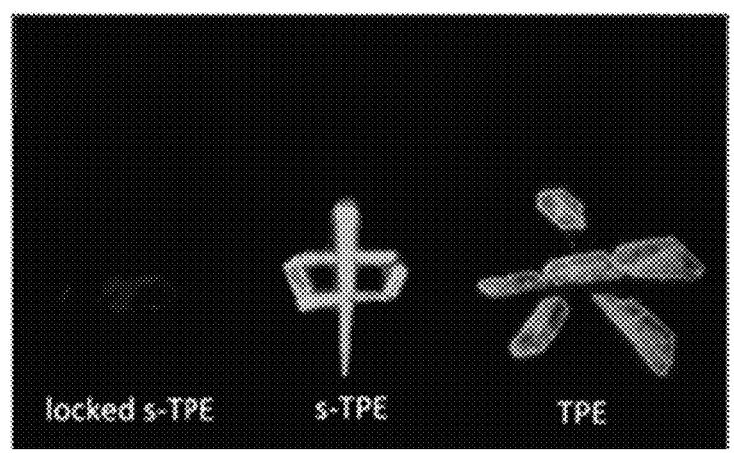
FIG. 4B

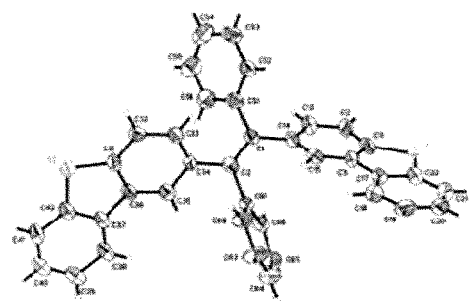
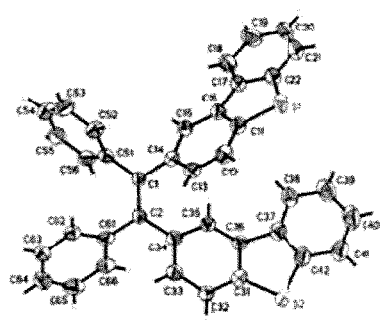
*Fig. 10*
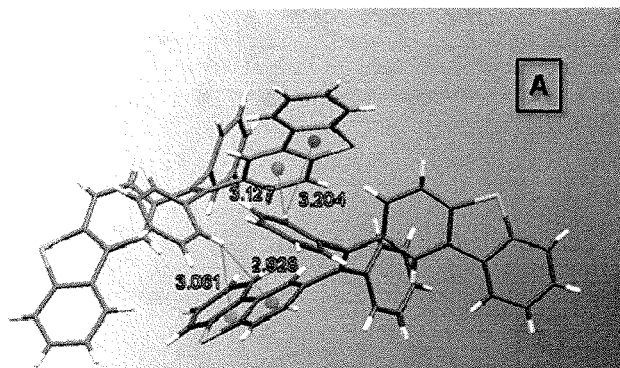
*Fig. 11A*
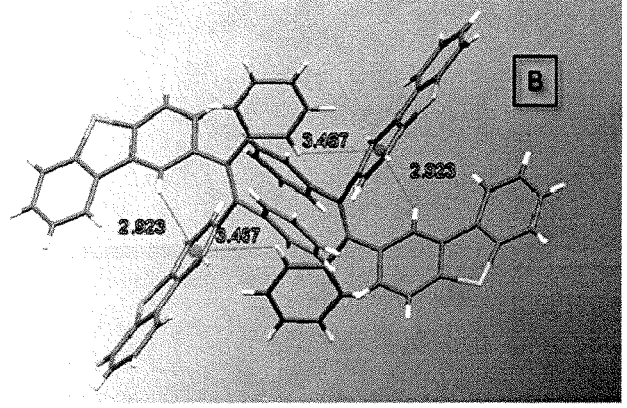
*Fig. 11B*

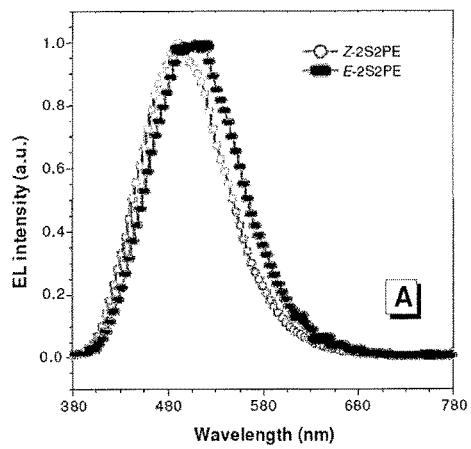
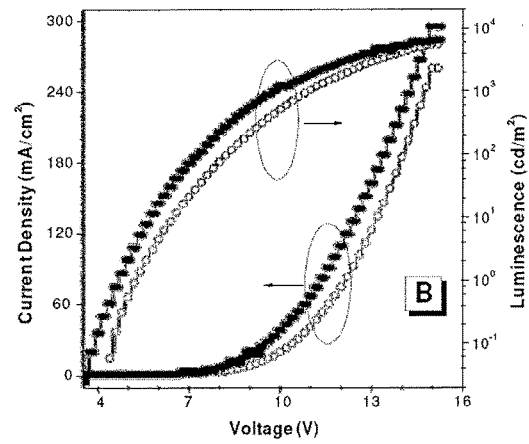
Fig. 14A  Fig. 14B
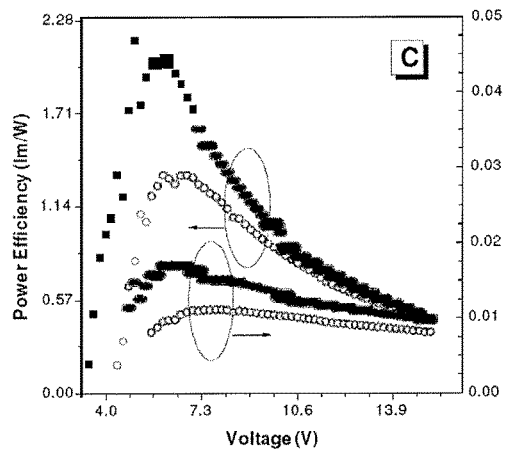
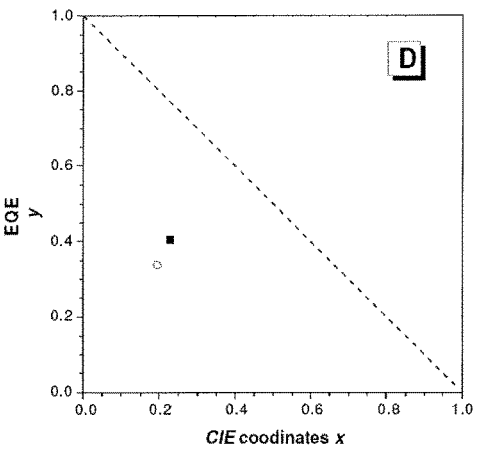
Fig. 14C  Fig. 14D

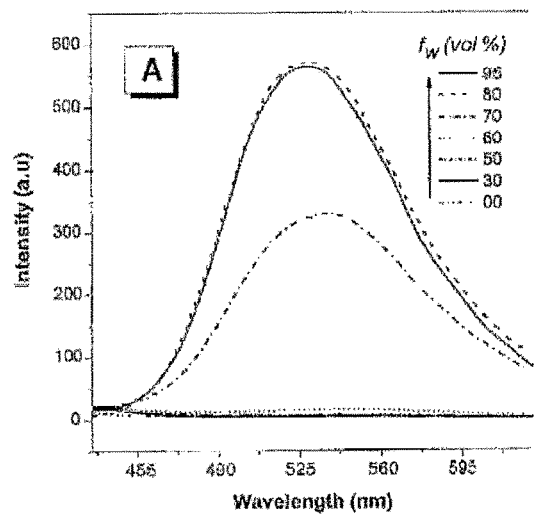
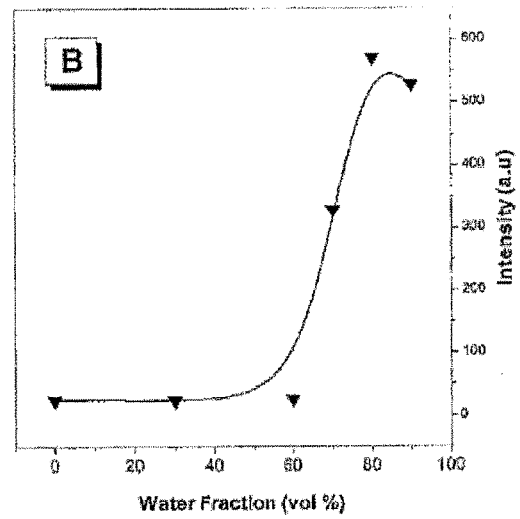
*Fig. 18A*    *Fig. 18B*
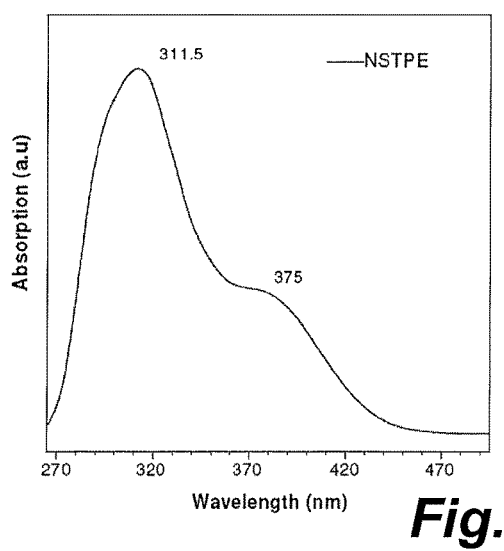
*Fig. 19*

DiCyano-DBTPE

COMPOSITION AND SYNTHESIS OF AGGREGATION-INDUCED EMISSION MATERIALS

RELATED APPLICATIONS

This is a National Phase Application filed under 35 U.S.C. 371 as a national stage of PCT/CN2014/083719, filed Aug. 5, 2014, an application claiming the benefit of U.S. Provisional Application No. 61/958,743, filed Aug. 5, 2013, the content of each of which is hereby incorporated by reference in its entirety.

TECHNICAL FIELD

The present subject matter relates to compositions containing and synthesis of fluorescent materials made from tetraphenylethylene (TPE) derivative compounds exhibiting aggregation induced emission (AIE) properties. Further contemplated herein are applications for TPE derivative compounds such as electroluminescent devices since they have a high efficiency, low turn on voltage, and excellent brightness. Additionally, application of TPE derivatives exhibiting AIE properties in various fields such as OLEDs, forensic technology and the examination of latent prints, and various other biological and industrial sectors are discussed.

BACKGROUND

Electroluminescence is the energy absorbed by molecules that are subject to electric current or a strong electric field that elevates the electrons to the excited state, which can be created by various sources. The most widely used and convenient source is ultraviolet (wavelength from 100 to 400 nm) or visible light photons, which can be simply accomplished even from a hand-held UV lamp.

The efficiency of electroluminescent devices based on organic fluorescent materials is hardly obtained higher than 25%, because under electrical excitation, 25% of the excited photos are in a singlet state, while the others (75%) are in the triplet state. Phosphorescent material is, therefore, required for such application. However, it is expensive to prepare phosphorescent materials as they normally possess heavy metals such as Ir (III) and Pt (II) ions. Although organic materials show the advantages of structure and low price, their fluorescence properties make them less attractive for device application.

Another optical phenomenon is chemiluminescence where the light is emitted due to a chemical reaction. Luminol or 3-aminophthalhydrazide is a chemiluminescence compound that gives bright blue light when oxidized by hydrogen peroxide or blood. It is widely used in crime scene investigations of trace blood wiped by the suspect. Chemiluminescence from luminol derivatives are widely investigated, but some other types of known chemiluminescence systems, using peroxyoxalic derivatives, adamantine derivatives, coelenterazine derivatives, and/or acridinium derivatives have also been investigated.

However, these days, electroluminescence and chemiluminescence are generated with the help of UV light, which is known to be a major source of human skin cancer. For this reason, there is a need for fluorescent materials that can emit light without the help of UV excitation.

A recent phenomenon that has been discovered is triboluminescence or mechanoluminescence. Triboluminescence is an optical phenomenon where the crashing or pressing of chemical bonds generates light. This phenomenon is of particular importance because light is generated without aid of an excitation source, for example UV light. This kind of effect can be used broadly in anti-counterfeiting, disposable application or sensing the instant motion generated in short amount of time upon the material with triggering the material collapsed to give off emission.

Organic dyes are rich in variety and have been widely used as readily processable light-emitting materials, particularly in the area of organic optoelectronics. Due to their poor miscibility with water, organic dyes are prone to aggregate in aqueous media, which normally weakens their light emissions. This effect is commonly known as aggregation-caused quenching (ACQ).

For sensitive detection, fluorescent materials must emit intense visible light upon photoexcitation. However, light emissions from most luminophores are rather weak. This aggregation-caused quenching (ACQ) is due to emission quenching caused by the aggregation of luminophores in the solid state. When dispersed in aqueous media or bound to biomolecules, luminogenic molecules are inclined to aggregate, which usually quenches their fluorescence, and thus greatly limits their effectiveness as bioprobes. The ACQ effect also makes it difficult to assay low-abundance molecular species in biological systems because the fluorescence signals from minimal amounts of luminophores matching the bioanalyte levels may be too weak to be determined accurately. In addition, at high luminophore concentrations, the emissions are further weakened, rather than enhanced, due to the ACQ effect.

Accordingly, there is a great need for the development of fluorescent materials that exhibit electroluminescence, and chemiluminescence to obtain readily available light-emitting materials, particularly in the area of organic optoelectronics. Further, there is also a need to develop materials exhibiting triboluminescence properties that are able to emit light without UV excitation.

SUMMARY

Therefore, the present subject matter relates to materials resistant to the ACQ effect to obtain readily processable light-emitting materials. In addition, the present subject matter relates to materials capable of excitation without the help of UV light.

The present application discusses a novel composition, A s-TPE composition for cell imaging, use as a halogen sensor, or as a light enhancement having formula I wherein formula I is

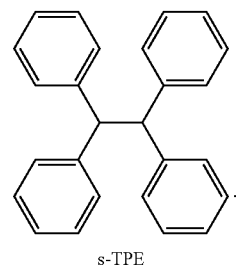 [SMILES: c1ccc(C(c2ccccc2)C(c2ccccc2)c2ccccc2)cc1 ; "."]

s-TPE

Further, in some embodiments, a TPE derivative composition having a luminogen exhibiting aggregation induced emission comprising: at least one luminogen having a backbone structure selected from a group consisting of

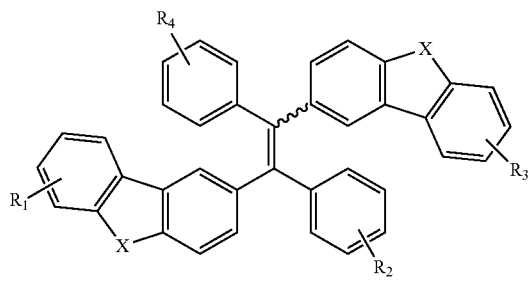

wherein $R_1$, $R_2$, $R_3$, and $R_4$ each can be independently selected from the group consisting of hydrogen, alkyl, unsaturated alkyl, heteroalkyl, cycloalkyl, heterocycloalkyl, aryl, and heteroaryl; and wherein each X is independently selected from the group consisting of O, S, Se, Te, C, Si, Ge, P, As, and Sb. Additionally, a method of synthesizing the TPE derivatives is also disclosed.

Further, in another embodiment, a one-pot method of synthesizing an aromatic ketone derivative comprising: (a) reacting a carboxylic starting material, of formula I with thionyl chloride and DMF to obtain $Ar_1$-carbonyl chloride, wherein $Ar_1$ is selected from the group consisting of toluene, methoxyphenyl and halogenated phenyls; and (b) reacting $Ar_1$-carbonyl chloride with DBT under DCM reflux to obtain an aromatic ketone derivative of Formula II, wherein $Ar_2$ is DBT;
wherein Formula I is

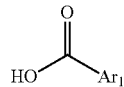

and wherein Formula II is

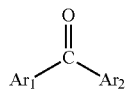

Further, in another embodiment, the present application also discloses aromatic ketone derivative composition used in synthesizing TPE-derivatives having the formula

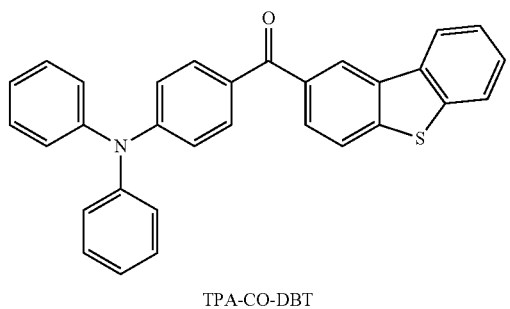 [SMILES: O=C(c1ccc(N(c2ccccc2)c2ccccc2)cc1)c1ccc2sc3ccccc3c2c1]

TPA-CO-DBT

In certain embodiments, a TPE derivative composition is disclosed having a luminogen exhibiting aggregation induced emission comprising: at least one luminogen having a backbone structure selected from the group consisting of

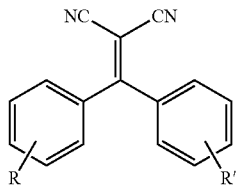

wherein each R and R' are independently selected from the group consisting of H, alkyl, unsaturated alkyl, heteroalkyl, cycloalkyl, heterocycloalkyl, aryl, heteroaryl, and wherein each X is independently selected from the group consisting of O, S, Se, Te, C, Si, Ge, P, As, and Sb.

Finally, an organometallic composition containing luminogens with AIE properties and tribolumescence, comprising: at least one luminogen having a backbone structure selected from the group consisting of:

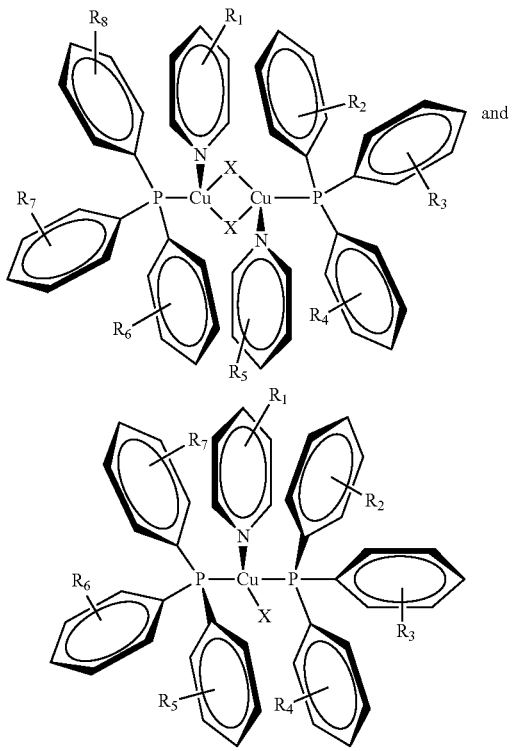

wherein each $R_1$, $R_2$, $R_3$, $R_4$, $R_5$, $R_6$, $R_7$ and $R_8$ are independently selected from the group consisting of H, alkyl, unsaturated alkyl, heteroalkyl, cycloalkyl, heterocycloalkyl, aryl, and heteroaryl; wherein each X is selected from the group consisting of F, Cl, Br, I, and At. Additionally, a method of synthesizing the organometallic composition is also disclosed.

The present application also discusses a novel procedure to convert s-TPE to TPE under mild conditions which is highly promising in the biological fields and the industrial sector. Additionally, dibenzothiophene (DBT) and dibenzofuran (DBF)-containing TPE derivatives 1,2-bis(dibenzo[b,d]thiophen-2-yl)-1,2-diphenylethene (STPE) 1,2-bis(dibenzo[b,d]furan-2-yl)-1,2-diphenylethene (OTPE) are synthesized such that STPE and OTPE emit efficiently in the solid state and enjoy high morphological and thermal stability. Further, the synthesis of various STPE derivatives, as well as their AIE properties, is discussed herein. Additionally, the present subject matter relates to synthesis of the DBT-derivative 2-(bis(4-((4-(1-(dibenzo[b,d]thiophen-2-yl)-2,2-diphenylvinyl)phenyl) ethynyl) phenyl) methylene) malononitrile (Dicyano-DBTPE), which is shown to be an efficient electron acceptor core in AIE engineering.

Further, the present subject matter relates to a general protocol for fingerprint detection. The present application also relates to replacement of UV excitation sources, and the mechanism of triboluminescence with respect to AIE materials having an organometallic core.

LIST OF ABBREVIATIONS USED

ACQ Aggregation-induced quenching
AEE Aggregation-enhanced emission
AIE Aggregation-induced emission
AIPE Aggregation-induced phosphorescence
$Alq_3$ Tris (8-hydroxyquinolinate) aluminum
Ar Aromatic
au Arbitrary unit
cm Centimeter
CV Cyclic voltammetry
δ Chemical shift
d Diameter
DDPD N,N-Dicyclohexyl-1,7-dibromo-3,4,9,10-perylenetetracarboxylic diimide
Δf Solvent polarity parameters
DFT Density functional theory
DMF N,N'-Dimethylformamide
DMSO Dimethyl sulfoxide
DNT 2,4-Dinitrotoluene
DPA Dipropylamine
DSC Differential scanning colorimeter
ε Molar absorptivity
ED Electron diffraction
$E_g$ Energy band gap
$E_{onset-ox}$ Onset oxidation potential
eq Equation
ESIPT Excited-state intramolecular proton transfer
$Et_3N$ Triethylamine
φ Fluorescence quantum efficiency
FRET Förster Resonance energy transfer
fs Femto-second
FSNPs Fluorescent silica nanoparticles
$f_w$ Water fraction
$g_{em}$ Emission dissymmetry factor
HOMO Highest occupied molecular orbital
HPS Hexaphenylsilole
HRMS High resolution mass spectra
ICT Intra-molecular charge transfer
IR Infra-red
ITO Indium tin oxide
$K_{SV}$ PL quenching constant
λ Wavelength
LCD Liquid crystal display
LE Locally excited
LLS Laser light scattering
$λ_{ab}$ Absorption maximum
$λ_{em}$ Emission maximum
$λ_{ex}$ Excitation wavelength
$λ_{onset}$ Onset absorption wavelength
LUMO Lowest unoccupied molecular orbital
MALDI Matrix-assisted laser desorption/ionization
mM Millimolar
mmol Millimole
mV Minivoltage
$M_w$ Relative weight average molecular weight
V Frequency
NBS N-Bromosuccinimide
nd Not determined
$η_{EL}$ Maximum external EL efficiency
nm Nanometer
NMR Nuclear magnetic resonance
NPB N,N'-Bis(1-naphthalenyl)-N,N'-bis(phenyl)benzidine
OFETs Organic field-effect transistor
OLED Organic light-emitting diodes
PL Photoluminescence
$PPh_3$ Triphenylphosphine
ppm Part per million
RIR Restriction of intramolecular rotations
RNA Ribonucleic acid
$S_0$ Ground state
$S_1$ Excited state
τ Lifetime
$T_1$ Excited triplet state
$T_d$ Decomposition temperature for 5% weight loss
TEM Transmission electron microscopy
TGA Thermogravimetric analysis
THF Tetrahydrofuran
$TiCl_4$ Titanium(IV) chloride
TICT Twisted intramolecular charge transfer
TLC Thin-layer chromatography
TMS Tetramethylsilane
TPBi 1,3,5-Tris(1-phenyl-1H-benzo[d]imidazol-2-yl)-benzene
TPE Tetraphenylethene
TsOH p-Toluenesulfonic acid monohydrate
UV Ultra violet
V Voltage
$V_{on}$ Turn-on voltage
WOLEDs White organic light-emitting diodes
XPS X-ray Photoelectron spectroscopy
XRD X-ray Diffraction
μm Micrometer

BRIEF DESCRIPTION OF THE DRAWINGS

FIGS. 4A and B show photoluminescence of crystals. FIG. 4A shows Photoluminescence spectra of crystals of TPE, s-TPE and ls-TPE. Excitation wavelength (nm): 330 (TPE and s-TPE) and 280 (ls-TPE). FIG. 4B is a series of Fluorescence photos of crystals of TPE, s-TPE and ls-TPE under 365 nm UV illumination.

FIG. 8A shows PL spectra of STPE in THF and THF/water mixtures with different water fractions.

FIG. 9A represents PL spectra of OTPE in THF and THF/water mixtures with different water fractions.

FIG. 10 shows ORTEP drawings of (A) E-STPE and (B) Z-STPE.

FIGS. 11A and B are schematic diagrams depicting the weak interaction of CH•••π interactions. FIG. 11A depicts the interactions in E-STPE, and FIG. 11B depicts the interactions in Z-STPE.

FIG. 13A depicts fabricated OLED devices with OTPE and STPE of Electroluminescence (EL) spectra; FIG. 13B depicts fabricated OLED devices with OTPE and STPE of Brightness (right axle) power efficiency (left axle) versus voltage; FIG. 13C depicts fabricated OLED devices with OTPE and STPE of External quantum efficiency (right axle) and current density (left axle) versus voltage; and FIG. 13D depicts fabricated OLED devices with OTPE and STPE of CIE coordinates of OTPE and STPE. Configuration: ITO/NPB (60 nm)/Dye (20 nm)/TPBi (10 nm)/Alq3 (30 nm)/LiF (1 nm)/Al (100 nm).

FIGS. 14A-D are graphical diagrams depicting OLED devices of STPE isomers. FIG. 14A depicts OLED devices of STPE isomers Electroluminescence (EL) spectra; FIG. 14B depicts Luminescence (right axle) and current density (left axle) versus voltage spectra; FIG. 14C depicts External quantum efficiency (right axle) and power efficiency (left axle) versus voltage; and FIG. 14D depicts CIE coordinates of Z- and E-STPE. Configuration: ITO/NPB (60 nm)/Dye (20 nm)/TPBi (10 nm)/Alq3 (30 nm)/LiF (1 nm)/Al (100 nm)

FIG. 15A shows the PL Spectrum of TPA-CO-DBT emission quenching process (from vol. 0% to 70%).

FIG. 16A depicts the PL Spectrum of TPA-CO-DBT emission in different solvents.

FIGS. 18A and B are graphical diagrams illustrates the PL spectrum. FIG. 18A illustrates the PL spectrum of NSTPE in THF/water mixtures. FIG. 18B illustrates the PL spectrum of maximum intensity of increasing water fraction.

FIG. 19 shows Absorption spectrum of NSTPE in THF Solution, with the main peak at 311.5 nm with a shoulder at 375 nm.

FIG. 20A depicts fabricated OLED devices with NSTPE with (square) and without (circle) hole transporting layer of (A) Electroluminescence (EL) spectra. FIG. 20B depicts fabricated OLED devices with NSTPE with (square) and without (circle) hole transporting layer brightness (right axle) power efficiency (left axle) versus voltage; FIG. 20C depicts fabricated OLED devices with NSTPE with (square) and without (circle) hole transporting layer external quantum efficiency (right axle) and current density (left axle) versus voltage. FIG. 20D depicts fabricated OLED devices with NSTPE with (square) and without (circle) hole transporting layer CIE coordinates. Configuration: ITO/NPB-HTL (60 nm)/ Dye (20 nm)/TPBi (10 nm)/Alq3 (30 nm)/LiF (1 nm)/Al (100 nm)

FIG. 21A illustrates PL spectra of DiCyano-DBTPE in THF and THF/water mixtures with different water fractions.

FIG. 26A shows PL spectra of LX-1 in pyridine and pyridine/water mixtures with different water fractions ($f_W$).

FIG. 27A depicts π-π stacking. FIG. 27B depicts CH-π interaction in LX-1 crystals. FIG. 27C depicts Cu—I•••H. FIG. 27D depicts CH•••π interaction in LX-2 crystals.

DETAILED DESCRIPTION

Definitions

Figure 1:
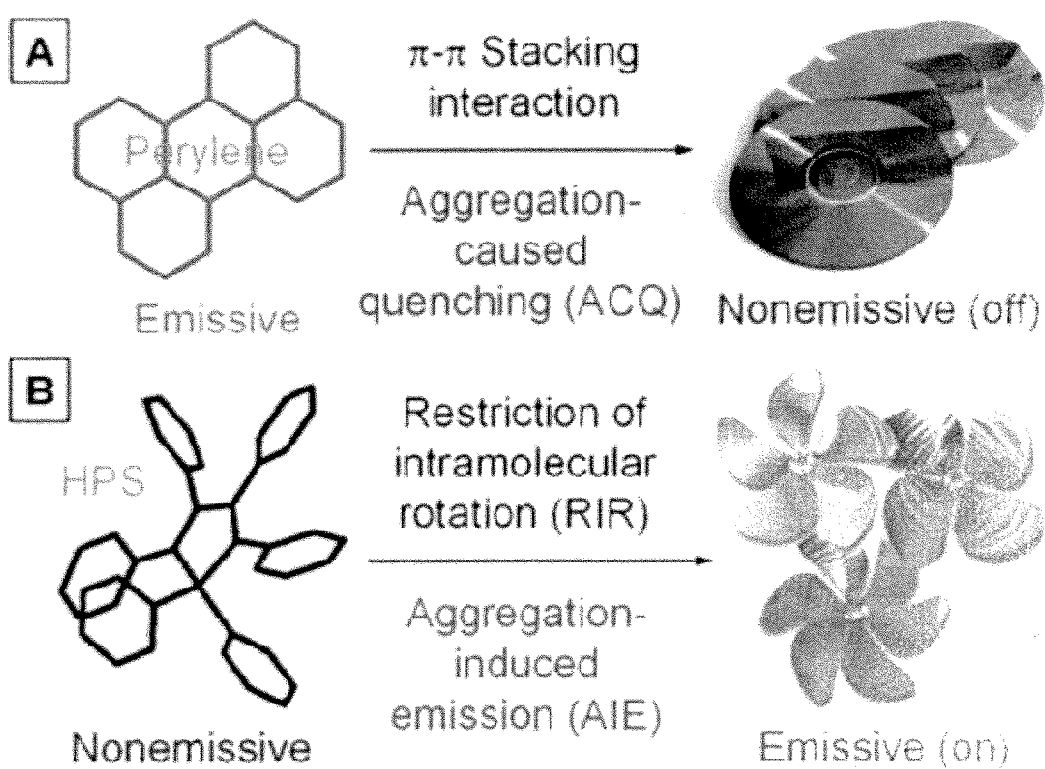
FIG. 1 demonstrates (A) planar luminophoric molecules such as perylene tend to aggregate as discs pile up, due to the strong π-π stacking interactions between the aromatic rings, which commonly turns "off" light emission. (B) Non-planar luminogenic molecules such as hexaphenylsilole behave oppositely, with their light emissions turned "on" by aggregate formation, due to the restriction of the intramolecular rotation of the multiple phenyl rotors against the silole stator in the aggregate state.

Unless, defined otherwise, all technical and scientific terms used herein have the same meanings as commonly understood by someone ordinarily skilled in the art to which the present subject matter pertains. The following definitions are provided for the purpose of understanding the present subject matter and for constructing the appended patent claims.

The term "acetyl" as used herein refers to the presence of a pendant acetyl group ($COCH_3$) in the structure of the molecules or the material described herein.

The phrase "aggregation caused quenching" or "ACQ" as used herein refers to the phenomenon wherein the aggregation of π-conjugated luminogens significantly decreases the fluorescence intensity of the luminogens. The aggregate formation is said to "quench" light emission of the luminogens.

The phrase "aggregation induced emission" or "AIE" as used herein refers to the phenomenon manifested by compounds exhibiting enhancement of light-emission upon aggregation in the amorphous or crystalline (solid) states whereas they exhibit weak or almost no emission in dilute solutions.

The term "alkyl" as used herein refers to an aliphatic hydrocarbon group which may be a straight or branched chain. The alkyl may comprise about 1 to 15 carbon atoms in the chain, optionally substituted by one or more groups.

The term "aryl" as used herein refers to an optionally substituted monocyclic or multicyclic aromatic carbocyclic moiety, such as phenyl, naphthyl, anthracene, tetracene, pyrene, etc. The aryl may comprise about 6 to 18 carbon atoms.

The term "cycloalkyl" as used herein refers to an optionally substituted non-aromatic monocyclic or multicyclic ring system. The cycloalkyl may comprise about 3 to 10 carbon atoms.

The phrase "emission intensity" as used herein refers to the magnitude of fluorescence/phosphorescence normally obtained from a fluorescence spectrometer or a fluorescence microscopy measurement.

The term "heteroalkyl" as used herein refers to an alkyl in which at least one carbon atom is replaced by a heteroatom.

The term "heteroaryl" as used herein refers to an optionally substituted aromatic monocyclic or multicyclic organic moiety. The heteroaryl may comprise about 5 to 10 ring members in which at least one ring member is a heteroatom. The heteroatom refers to an atom selected from the group consisting of nitrogen, oxygen, sulfur, phosphorus, boron and silicon.

The term "heterocycloalkyl" as used herein refers to a cycloalkyl group in which at least one ring member is a heteroatom. The heterocycloalkyl may comprise about 3 to 7 ring members.

The term "vinyl" as used herein refers to the presence of a pendant vinyl group ($CH_2=CH-$) in the structure of the molecules or the material described herein.

The term "luminogen" as used herein refers to a chemical compound that manifests luminescence.

Throughout the application, descriptions of various embodiments use "comprising" language; however, it will be understood by one of skill in the art, that in some specific instances, an embodiment can alternatively be described using the language "consisting essentially of" or "consisting of."

The term "a" or "an" as used herein includes the singular and the plural, unless specifically stated otherwise. Therefore, the term "a," "an," or "at least one" can be used interchangeably in this application.

For purposes of better understanding the present teachings and in no way limiting the scope of the teachings, unless otherwise indicated, all numbers expressing quantities, percentages or proportions, and other numerical values used in the specification and claims, are to be understood as being modified in all instances by the term "about." Accordingly, unless indicated to the contrary, the numerical parameters set forth in the following specification and attached claims are approximations that may vary depending upon the desired properties sought to be obtained. At the very least, each numerical parameter should at least be construed in light of the number of reported significant digits and by applying ordinary rounding techniques.

The present subject matter relates to the phenomenon, known as aggregation-induced emission (AIE), wherein nonemissive luminogens such as tetraphenylethene (TPE) are induced to emit efficiently in aggregate formation. The AIE effect dramatically boosts the fluorescence quantum yields of the luminogens, changing them from faint luminophores to strong emitters.

Aggregation-Caused Quenching (ACQ) and Aggregation-Induced Emission (AIE) Phenomena ACQ is a known phenomenon that causes planar luminophoric molecules to aggregate as discs and pile up due to the strong π-π stacking interactions between aromatic rings, which deters the luminophoric particles from emitting light, and therefore, turns off the light emission.

AIE, on the other hand, is a phenomenon where non-planar luminogenic molecules can turn on their light emissions by aggregate formation due to the restriction of the intramolecular rotation of the multiple phenyl rotors against the silole stator in the aggregate state.

The phenomena are explained in FIG. 1, which illustrates the ACQ phenomenon in perylene which is a planar luminophoric particle, as opposed to hexaphenylsilole, which is a non-planar luminophoric particle exhibiting AIE phenomena.

AIE molecules are endowed with strong light emission in the solid state because they preserve the highly twisted "propeller-like" conformation, which prohibits the π-π stacking that is detrimental to the light emission. Moreover, the intramolecular rotation of the molecules is restricted upon aggregation, which turns the dye molecules into strong emitters.

Figure 2A:
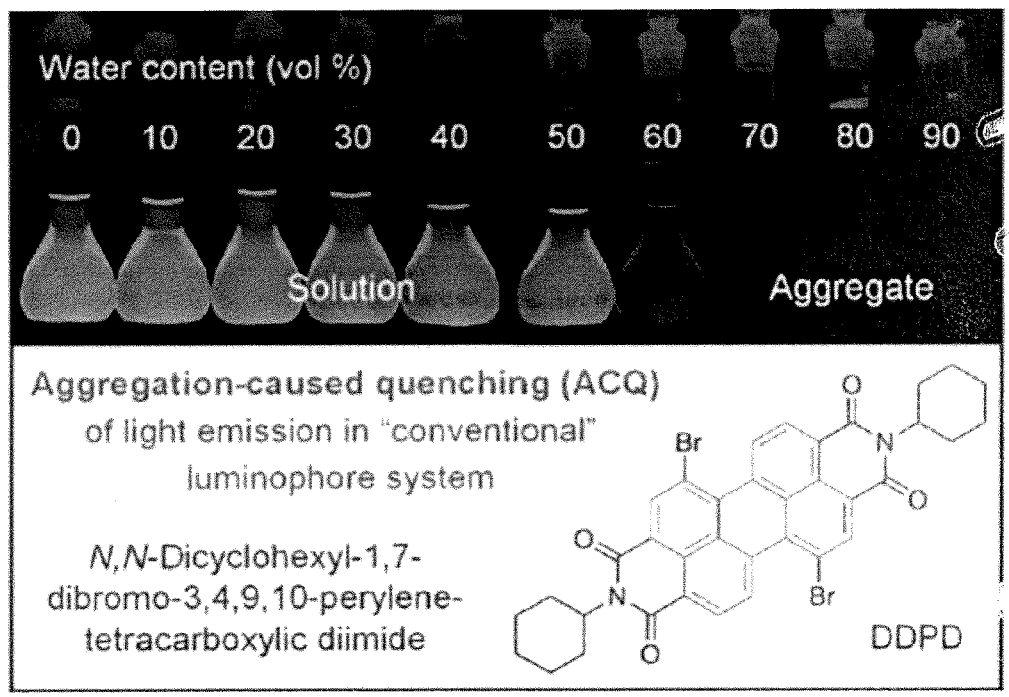
FIG. 2A shows photo luminescent photographs of solutions/suspensions of DDPD (10 μM) in THF/water mixtures with different water contents.
Figure 2B:
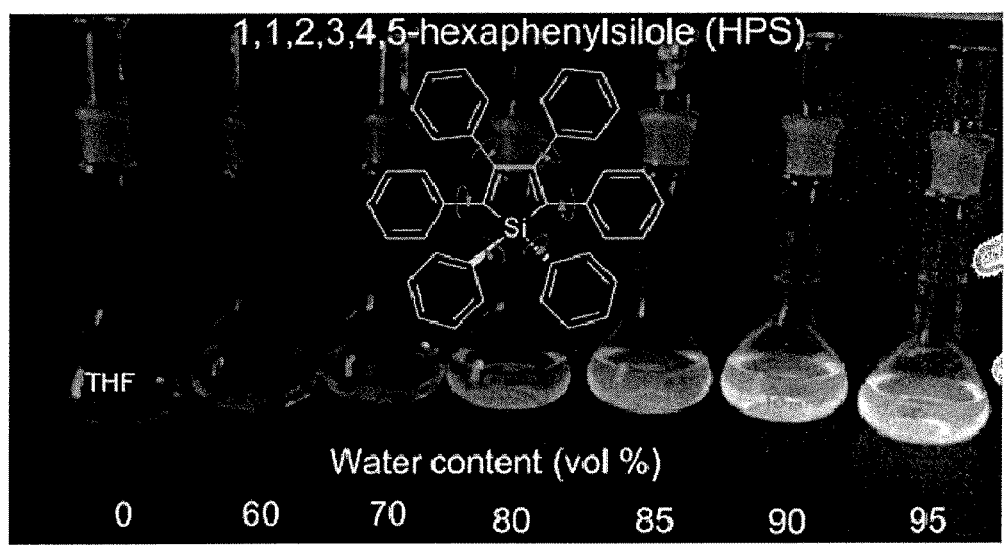
FIG. 2B shows photoluminescent photographs of solutions/suspensions of HPS (10 μM) in THF/water mixtures with different water contents.

FIGS. 2A and 2B further exemplify the ACQ vs. AIE phenomena. In FIG. 2A, DDPD is constructed from perylene and is shown to possess a planar structure. In pre-THF solution, DDPD shows a strong emission. Upon addition of water, a poor solvent of the luminogen, into the THF solution, which has weakened the light emission, the molecules aggregate at 60% water fraction, and faint emission is still observed. However, the solution is completely non-fluorescent when the water fraction is increased to 70%. Such phenomenon proves that the ACQ is a thorny problem when such a large disc-like dye is utilized in the aggregated state.

On the other hand, as shown in FIG. 2B, HPS shows an abnormal phenomenon that is the exact opposite of the ACQ effect, i.e., it exhibits the AIE effect. In pre-THF solution, HPS is completely non-emissive. However, when 60% of water is added to the THF solution, a faint emission is detected. As the water content in the solution is increased, higher fluorescent enhancement is observed. The THF/water mixture with a 90% water fraction shows very strong light emission. Therefore, such emissions can have many practical applications in various industries.

AIE Materials and Restriction of Intramolecular Rotation (RIR)

Most luminogens are synthesized with freely rotatable phenyl rings. In a solution state, the active intramolecular rotation quenches emissions of the molecules. However, after aggregation of the luminogens as nanoparticles in a poor solvent, in the solid state, the motion of the rotatable phenyl rings is restricted which eliminates the quenching effect, enabling excitation, and therefore, light emission. Therefore, the change in materials that exhibit ACQ effects to those that exhibit AIE effects can be explained due to the RIR mechanism.

Figure 3:
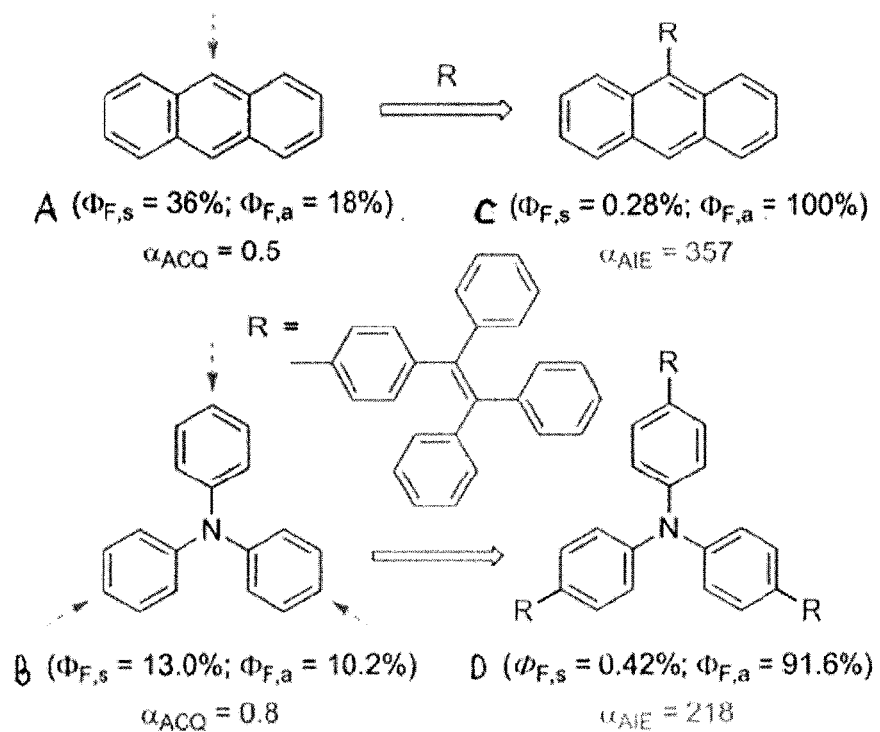
FIG. 3 shows the philosophy of transforming ACQ luminophores to AIE materials.

As depicted in FIG. 3, in one embodiment of the present application, a versatile method is developed to synthesize AIE-materials. It was found that when AIE exhibiting units, such as TPE, are appended onto ACQ luminophores, the resulting luminogens exhibit AIE characteristics without causing any adverse effects.

In this regard, FIG. 3 demonstrates that anthracene (A) and triphenylamine (C) are classic ACQ materials, which possess high solution state emission but emit faintly upon aggregate formation. However, compounds B and D, which are formed on the incorporation of TPE, exhibit absolute solid state quantum yields of more than about 90%, while their solution-state quantum yields are relatively low and less than 1%. This occurs because the twisted formation of the TPE unit prevents undesirable π-π stacking interactions between molecules, thereby turning the dye molecules into strong emitters.

Synthesis of s-TPE and Conversion of s-TPE to TPE

In one embodiment of the present subject matter, an s-TPE composition is synthesized. The sTPE composition is tetraphenylethane having a structure as shown below:

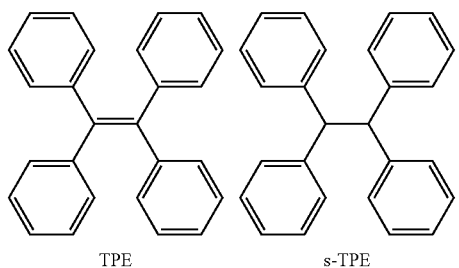

TPE                  s-TPE

As seen here, the phenyl rings of the TPE are held together by a double bond, whereas the presently synthesized s-TPE molecule does not have a double bind holding the four phenyl rings. However, in one embodiment of the present application, it has been unexpectedly found that both TPE and s-TPE are AIE materials. Accordingly, the s-TPE conjugation structure is counter-intuitive based on the TPE structures presently available. That is, the AIE effect of the s-TPE structure is counter-intuitive because it exchanges the central ethenylene bond for a non-restrictive ethylene bond. One of ordinary skill in the art would expect there is no longer a restriction of the intramolecular rotation of the multiple phenyl rotors in the aggregate state based on the presence of the ethylene rather than ethenylene central bond, and thus the AIE effect would be diminished. In fact, s-TPE has been found to exhibit intense luminescence upon UV excitation that has been unprecedented.

By locking the freely rotatable phenyl rings of TPE through cyclization, it was expected that the resulting compounds would change their emission behaviors from AIE to aggregation-caused quenching, ACQ. However, unexpectedly, it was found that s-TPE and other locked derivatives of TPE, shown below, were also AIE active.

Compound 1

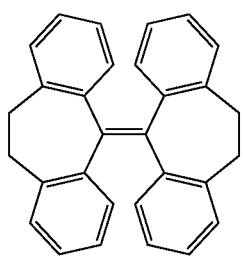

Compound 2

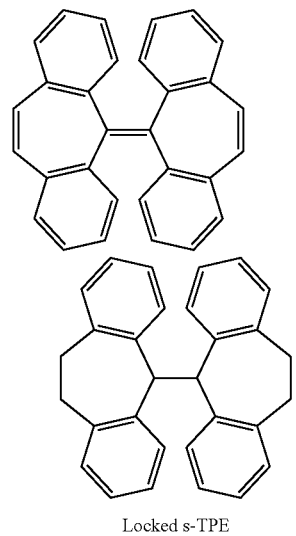

Locked s-TPE

Compounds 1 and 2, which were previously known, were studied to determine the cause of these unexpected results. Quantum energy allows excited state calculation by the TD-DFT method using 6G-BLG* and predicts ideal molecular distribution. On comparing the reorganization energies of compound 1 and 2, it was found that since compound 2 has more carbon double bonds, it has a more rigid structure than compound 1. Therefore, in another embodiment of the present application, the comparison of the reorganizational energies indicated that while the "locked" phenyl rings are unable to rotate without constraint, they are able to "vibrate". While TPE, which has phenyl rings that can rotate freely, can exhibit better AIE properties, the vibration of the locked rings of compounds 1 and 2, which occurs exclusively within the molecule, is the main factor for the AIE properties of compounds 1 and 2.

Further, the strength of emissions of TPE, s-TPE, and ls-TPE (or locked s-TPE) was studied. As shown in FIG. 4, the emission of light and wavelength of TPE as compared to s-TPE and ls-TPE varies. Studies have shown that the reason for the variation is due to the propeller shaped conformation of the AIE system. It is due to the ordered arrangements of phenyl rings to that a large Stokes shift can be seen.

Figure 5:
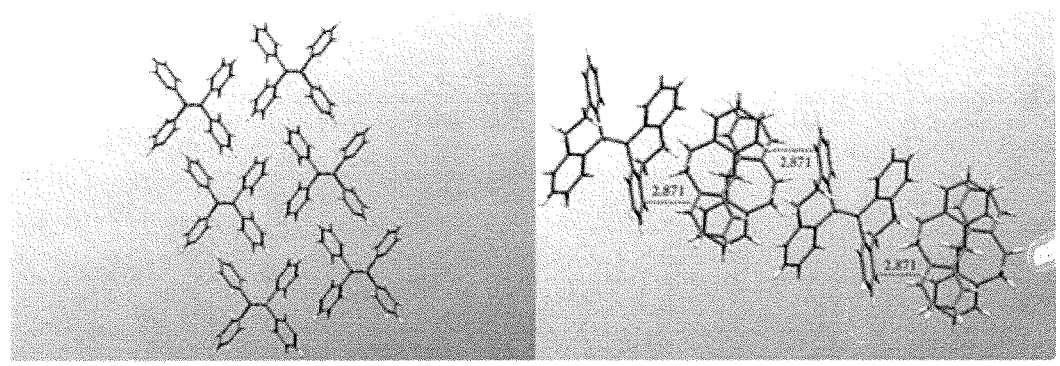
FIG. 5 shows weak intermolecular interactions of CH•••π (<3 Å) observed in (left) s-TPE and (right) ls-TPE.

Additionally, as depicted in FIG. 5, weak molecular interactions of CH . . . π are observed in the s-TPE and ls-TPE. The much redder emission of (~100 nm) of s-TPE crystals compared to that of ls-TPE verifies that both compounds are in the crystal state, and the vibrational excitation state are omitted in equal considerations. The molecular conformation is also possible for this phenomenon. In one embodiment, it was seen in FIG. 5 that s-TPE possess four phenyl rings in an ordered and relatively intimate distance intramolecularly. In another embodiment, it was noticed that ls-TPE is semi-ordered with two sets of phenyl rings facing in opposite directions and shifting less towards the red spectrum.

This theory was further confirmed by studying a group of single bonded s-TPE derivatives, as shown below. In one embodiment, the preparation of these s-TPE derivatives, with or without methyl groups, was devised and is explained in detail in the Example section of this application.

Chemical Structures of single bonded TPE derivatives

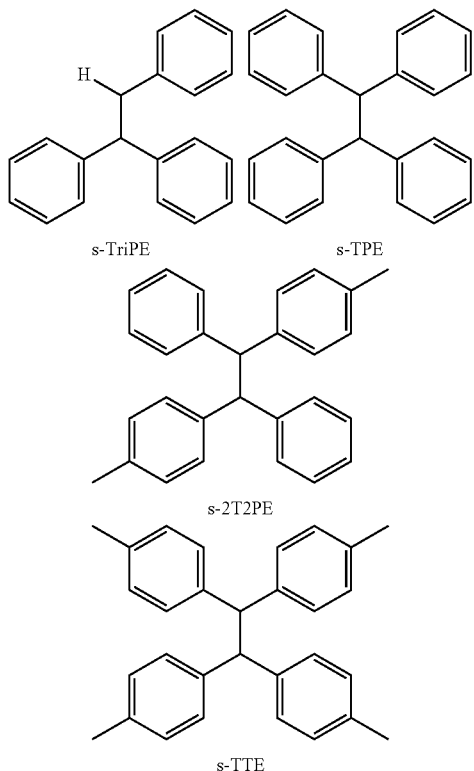

Figure 6:
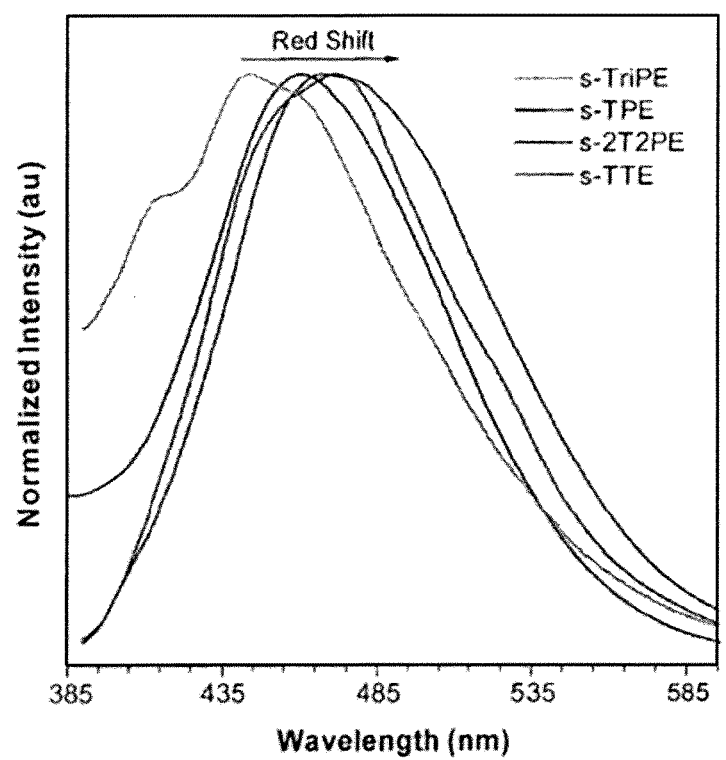
FIG. 6 shows solid-state photoluminescence spectra of s-TriPe, s-TPE, s-2T2PE and s-TTE at room temperature.

When the shift in wavelength towards the red spectrum was studied, it was found that when the number of methyl groups on the phenyl rings increase from 0 (s-TPE) to 4 (s-TTE) the emission maximum shifts from 449 nm for s-TPE to 467 nm for 2-T2PE and then 472 nm for s-TTE, as can be seen in FIG. 6. Therefore, in some embodiments of the present application, it can be seen that while the emission spectrum moves towards the red region, the extent is small. This is likely due to the presence of methyl groups that are electron saturated and hence do not exerts a strong effect on the electron transition of the molecules.

In one embodiment of the present application, a s-TPE compound for cell imaging, use as a halogen sensor, or as a light enhancement having a backbone structure of formula I is discussed. Formula I is represented by

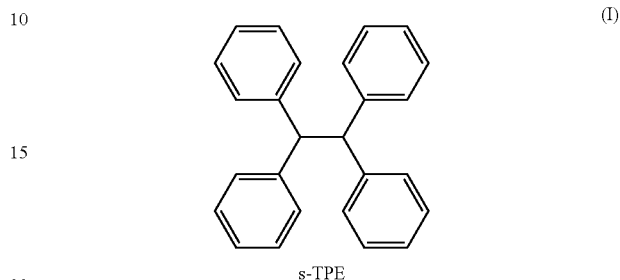

Further, in another embodiment, a method of producing an s-TPE composition is disclosed, the method comprising, (a) hydrogenating a suspension of TPE in methanol; (b) filtering the mixture after a given time period to obtain a solvent; (c) evaporating the solvent under vacuum to obtain a crude product; and (d) purifying the crude product to obtain s-TPE composition.

In one embodiment, as seen in FIG. 5, the s-TPE composition exhibits a Stockes shift of about 100 nm. Further, in another embodiment, the s-TPE emits light in the bluish-green region. In yet another embodiment, the phenyl rings of s-TPE are unlocked, and therefore are freely rotatable.

In another embodiment, a method of converting s-TPE to TPE is disclosed, the steps comprising: brominating a DCM (dichloromethane) solution of s-TPE under UV excitation to produce a bromine product, and eliminating the product to produce TPE. In some embodiments, the method of converting s-TPE to TPE is reversible. Shown below is the transformation of s-TPE to TPE under mild conditions.

Transformation of s-TPE to TPE under mild conditions

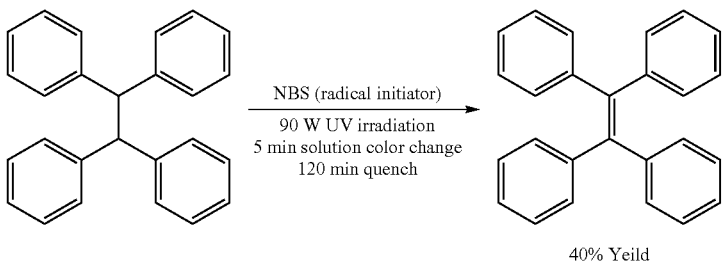

Mechanism proposed:

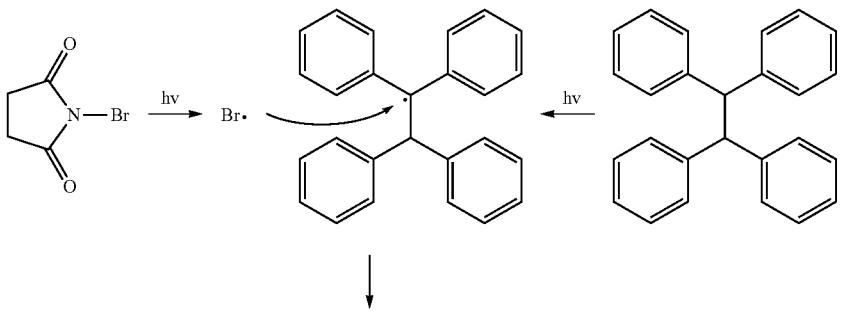

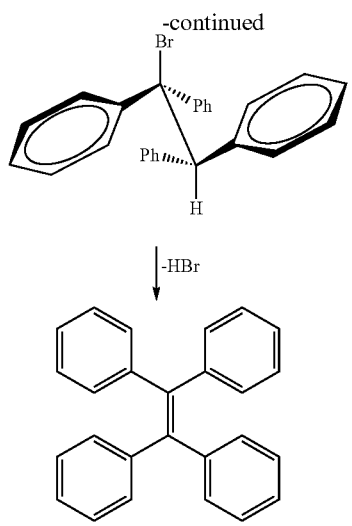

↓ -HBr

This novel procedure of conversion of s-TPE to TPE under mild conditions is highly promising, and has application in the biological and industrial sectors. Additionally, this method of conversion of s-TPE to TPE is potentially highly advantageous for designing luminogenic dyes with AIE characteristics.

Composition and Synthesis of Dibenzothiophene Functionalized Aggregated-Induced Emission Light Active Materials While it is known that thiophene is excellent with electron rich conjugation systems in its oligomer and polymer structures, dibenzothiophene (DBT) and dibenzofuran (DBF) are known to possess superior electronic properties since they are more planar. In one embodiment of the present application, DBT- and DBF-functionalized ethanes were synthesized via McMurry coupling reactions.

In another embodiment, a synthesis of new materials that possess AIE properties was obtained. In some embodiments, the DBT- or DBF-TPE derivative composition has a luminogens exhibiting AIE having at least one luminogen with a backbone structure selected from a group consisting of:

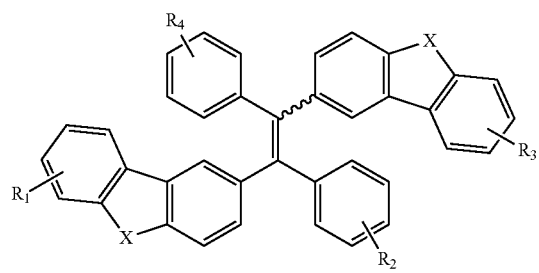

wherein $R_1$, $R_2$, $R_3$, and $R_4$ each can be independently selected from the group consisting of hydrogen, alkyl, unsaturated alkyl, heteroalkyl, cycloalkyl, heterocycloalkyl, aryl, and heteroaryl; and wherein each X is independently selected from the group consisting of O, S, Se, Te, C, Si, Ge, P, As, and Sb.

In an embodiment, the luminogen is STPE when X is sulfur. Further, in another embodiment, the luminogen is OTPE when X is oxygen. In various embodiments, each can independently further include hydrogen, alkyl, heteroalkyl, cycloalkyl, heterocycloalkyl, aryl, heteroaryl, or a combination thereof.

In some embodiments, STPE and OTPE are insoluble in water, and soluble in organic solvents. Further, in other embodiments, the DBT- or DBF-TPE derivative composition is soluble in organic solvents such as DCM, chloroform and THF.

In some embodiments, the DBT- or DBF-TPE derivative composition is resistant to high voltage. Further, in other embodiments the DBT- or DBF-TPE derivative composition emits red light or green light mixed with blue emissions. Additionally, due to the DBT- or DBF-TPE derivative composition having AIE properties, the luminogen emits light in its solid state. As far as practical applications, the DBT- or DBF-TPE derivative compositions are very useful in electroluminescent devices.

Additionally, the present subject matter also discloses a method of synthesizing a TPE derivative composition having a luminogen which exhibits aggregated induced emission comprising the steps: (a) adding benzoyl chloride to DBT or DBF; (b) refluxing the reaction mixture to obtain an intermediate compound; and (c) subjecting the intermediate compound to McMurry coupling reactions to obtain a TPE derivative. In some embodiments, the intermediate compound is Dibenzo[b,d]thiophen-2-yl(phenyl)methanone or Dibenzo[b,d]furan-2yl(phenyl)methanone. In another embodiment, aluminum chloride and dichloromethane are added to step (a) of the method for synthesizing TPE-derivatives.

In one embodiment, when DBT is used in step (a), an E-isomer of STPE is formed from a solution of DCM and methanol, wherein in step (a) the DBT is dissolved in the DCM solution, and methanol is gradually dropped into the solution. In other embodiments, when DBT is used in step (a), a Z-isomer is collected by filtration of the THF solution.

Two TPE derivatives were obtained using DBT and DBF as building block. The reactions were catalyzed by AlCl$_3$ and good yield was achieved for 1a and 2a, the formulas of which are shown below. The method of synthesizing these compounds is further explained in the Examples section.

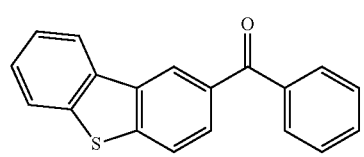

1a

-continued

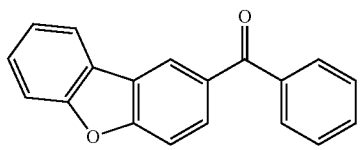

2a

In one embodiment, the products are easily separated, owing to their relatively higher polarity than the reactants. In another embodiment, one or more McMurray coupling reactions took place and STPE and OTPE were both obtained in satisfactory yields. It was surprisingly found that the big planar structures do not result in byproducts with ethane structures. So far, this is the most efficient method to synthesize DBT and DBF-containing AIE molecules.

Figure 7:
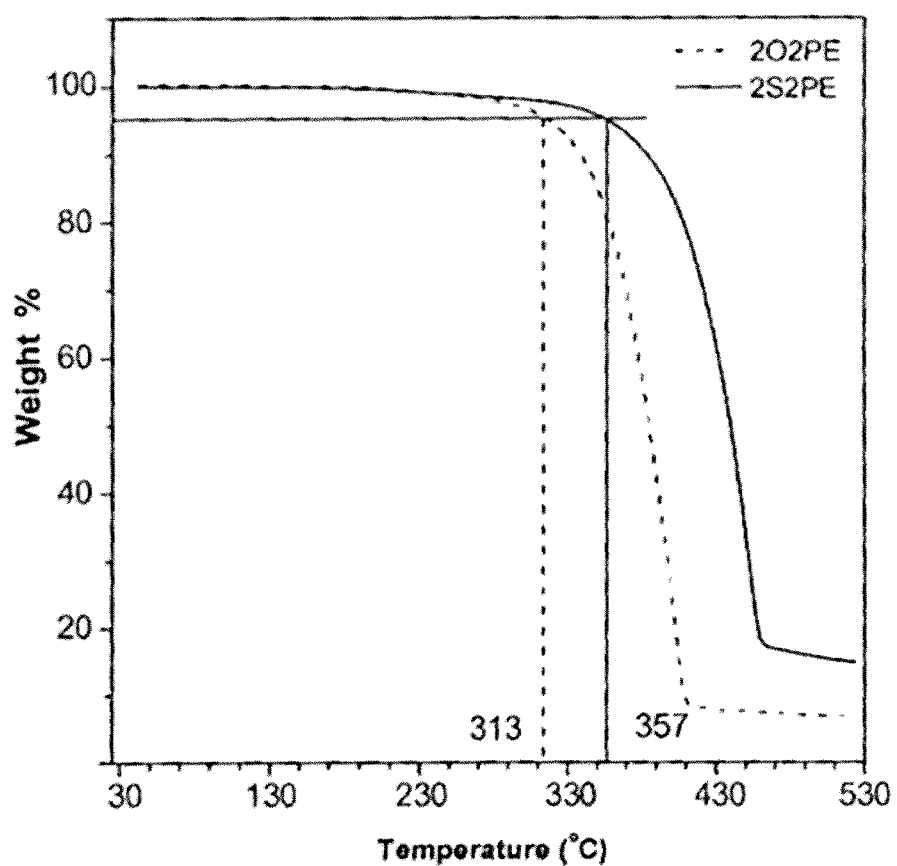
FIG. 7 depicts TGA measurement of STPE and OTPE.

Thermal stability of both molecules was measured as shown in FIG. 7. Their decomposition temperatures with only 5% weight loss are both above 300° C. according to TGA measurements. For example, in one embodiment, it was seen that the decomposition temperature of STPE is as high as 357° C. OTPE and STPE can both retain 50% of their weight even over 370° C. and 430° C. In addition, it was observed in another embodiment that with respect to element X, the replacement of sulfur with oxygen in the two materials give a decomposition temperature difference of about 40° C. This is seen predominantly because the sulfur atom is larger than the oxygen atom and STPE has a stronger interaction than OTPE, which is responsible for the relatively higher thermal stability. Therefore, it is understood in one embodiment of the application that a strong thermoresistance of the materials endows them with a high thermal stability in their potential applications such as device fabrication, especially organic light-emitting diodes.

Figure 8A:
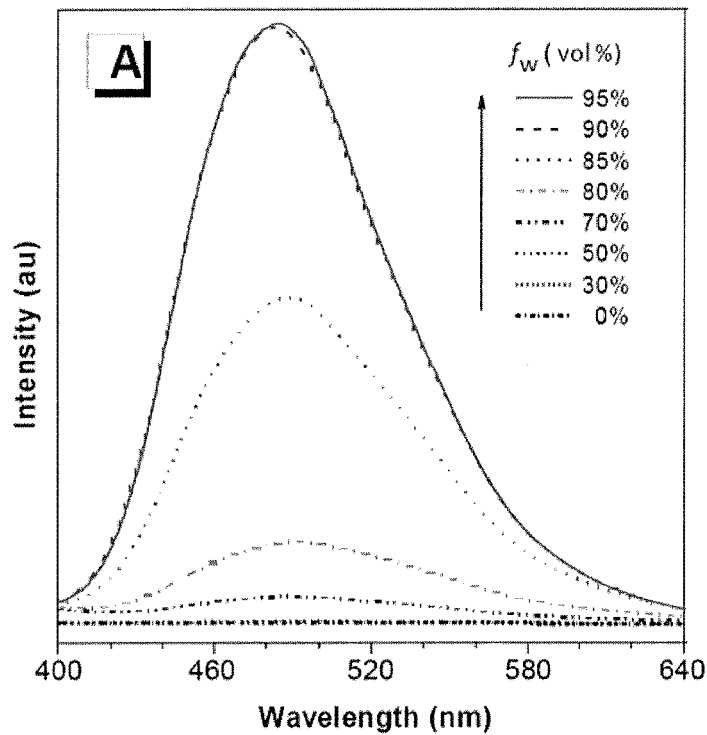
FIGS. 8A and B are graphical depictions of photoluminescence of STPE.
Figure 8B:
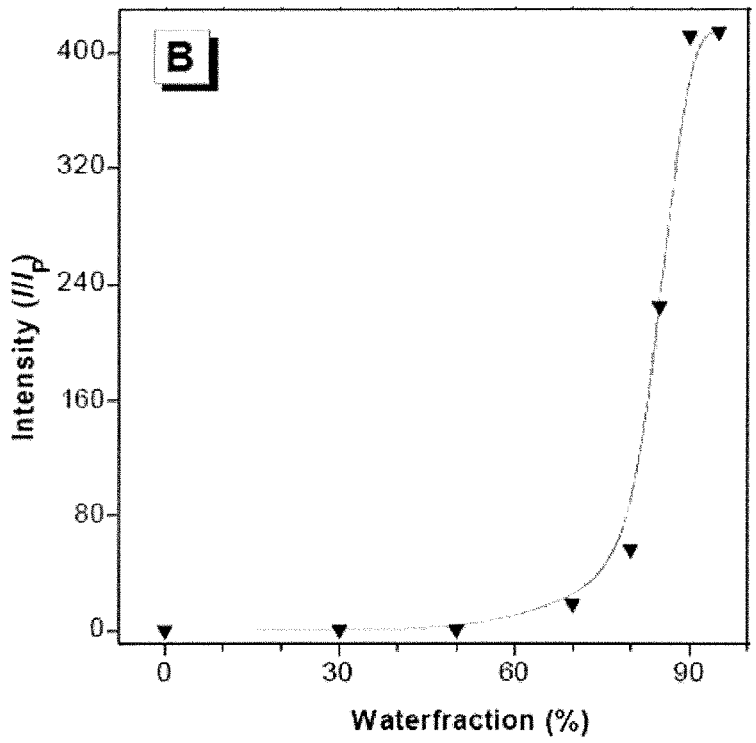
FIG. 8B shows change of PL intensity of STPE at water fraction in THF/water mixture. Dye concentration: 20 µM; excitation wavelength: 330 nm.

In some embodiments of the present subject matter, the two compounds STPE and OTPE have good solubility in common organic solvents such as THF, DCM and chloroform, while they cannot dissolve in water. THF/water mixtures were thus chosen to study how the aggregate affects their luminescence, using a photoluminescence spectrophotometer. As shown in FIG. 8, the THF solution of STPE is non-emissive. When poor solvent water is slowly added with vigorous stirring while keeping a fixed dye concentration of $10^{-5}$ M, an emission peak appears at 485 nm. FIG. 3B shows the emission intensity changes with the water fraction. Obviously, in the pure solution state (100% THF), the emission is barely detected by the PL spectrophotometer. There is no prominent enhancement of the intensity until the water fraction reaches 70%. Intense emission of the nanoaggregates was observed afterwards and the intensity reaches the maximum at a water fraction of 95%.

Figure 9A:
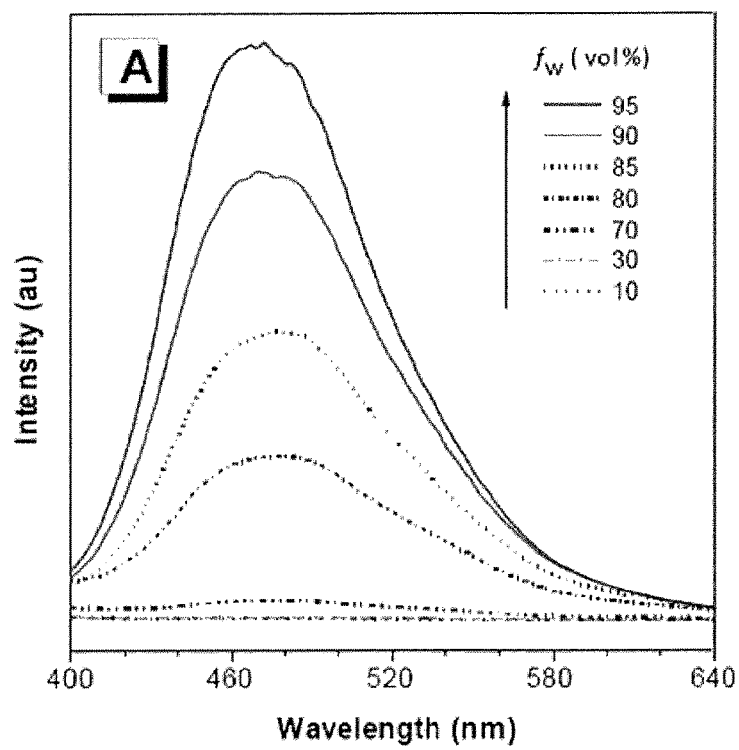
FIGS. 9A and B are graphical depictions of photoluminescence of OTPE.
Figure 9B:
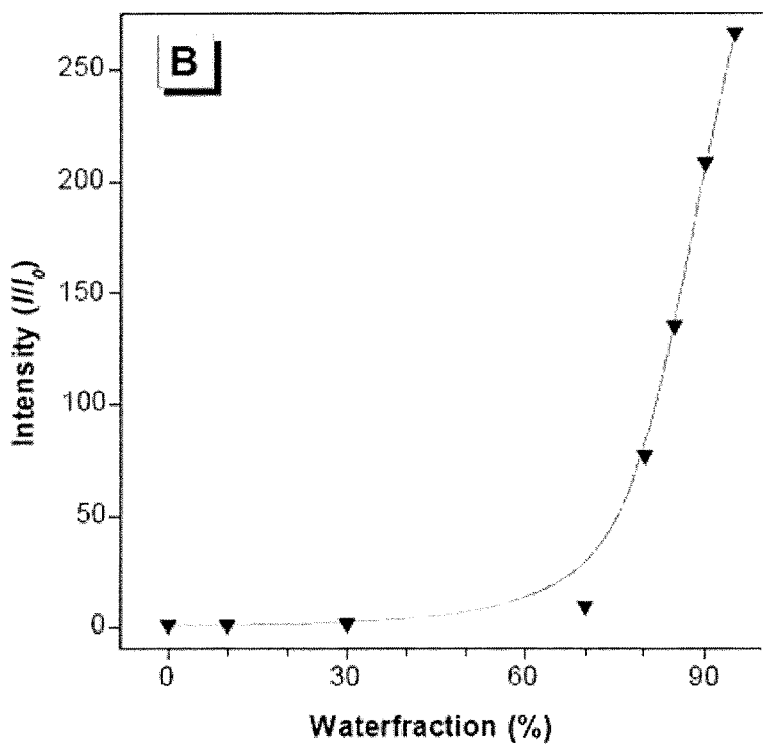
FIG. 9B shows change of PL intensity of OTPE at water fraction in THF/water mixture. Dye concentration: 20 µM; excitation wavelength: 330 nm.

In another embodiment of the present application, a similar phenomenon was observed with OTPE, as shown in FIG. 9. The trend of the intensity enhancement towards increasing water fraction was almost the same, but the maximum emission peak at 470 nm was 15 nm blue-shifted compared with STPE. The prominent enhancement of the luminescence was observed at 80% water fraction.

The RIR mechanism that was previously explained was used to interpret the experimental data discussed above. In one embodiment, it was seen that the intramolecular interactions of the dye are absent in the solution state. Abundant solvent molecules surround the dye molecules and the intramolecular free rotation can take place in the solution state. When more poor solvent water was added into the solution, the hydrophobic molecules started to aggregate. Hence, nanoaggregates formed in such THF/water mixtures as suspensions. Therefore, in some embodiments, it was seen that the internal rotations of dye molecules were restricted by the aggregations. Hence, the excited state non-radiative relaxation pathways were blocked, leaving the system emissive upon excitation.

Advantageously, it was seen in one embodiment of the present application, although STPE and OTPE both have big coplanar hetero-atom fused aromatic conjugation systems, the potential π-π stacking interaction does not affect their AIE behavior. In some embodiments, the intermolecular interactions in their crystalline states were inspected to determine why there is no quenching of emission in the aggregated state despite the big planar structure.

In one embodiment of the present subject matter, a single crystal of the E-isomer of STPE was obtained from the DCM and methanol mixed solution. In another embodiment, the Z-isomer of STPE was collected by filtration of the hot THF solution, which appeared as insoluble precipitates in the solution. The powder was then dissolved in a large amount of DCM and a single crystal of Z-isomer was obtained from the DCM/methanol mixed solution as shown in FIG. 10. Meanwhile, through similar methods, only micro needle crystals were formed from an OTPE mixed solution, which were not qualified for single crystal analysis. The detailed crystal parameters of E- and Z-isomers of STPE are shown in the Tables as discussed in the Examples section.

In one embodiment of the present application, the E- and Z-isomers of STPE were analyzed. Close inspection of the ORTEP drawing of the E- and Z-isomers of STPE suggest that the phenyl and DBT rings are twisted away from the ethene core plane and form a propeller-shaped structure, as shown in FIG. 10. Additionally, in one embodiment, intermolecular interactions were analyzed through molecular packing. The weak interactions found in the packing crystal cell units are shown in FIG. 11. Generally, there is one major interaction in the isomers: it is the CH•••π interaction. In one embodiment, it was found that the CH•••π interaction of the two isomers shares no common points.

As shown in FIG. 11A, the E-isomers only have intermolecular CH•••π interactions. On the labeled molecule of FIG. 11A, protons on the sp²-carbon of the adjacent phenyl ring interacts with the DBT unit in the blue molecule with a distance of 2.928 Å to the closest DBT phenyl ring π cloud center and 3.061 Å to the thiophene π center. For the Z-isomer (FIG. 11B), besides intermolecular CH•••π interactions with a distance of about 3.5 Å, the intramolecular CH•••π interactions between DBT protons on the 2-position proton to the adjacent DBT phenyl ring π center is observed with a distance of 2.923 Å. These intramolecular CH•••π interactions are responsible for the poor solubility of the Z-isomer in hot THF.

In one embodiment, it was seen that CH•••S interactions exist in the single crystal of the E-isomer between two neighboring DBT units from different STPE molecules. The fact that no π•••π interactions were observed advantageously explains why STPE presents no self-quenching emission in the aggregation state, but on the other hand, the CH . . . π interactions in isomers as well as the CH . . . S interactions in the E-isomers reinforce the twisted propeller like configuration explained above. Therefore, it prevents rotations or excimer formation, thus endowing the molecules with enhanced emission in the solid or aggregated state.

Figure 12:
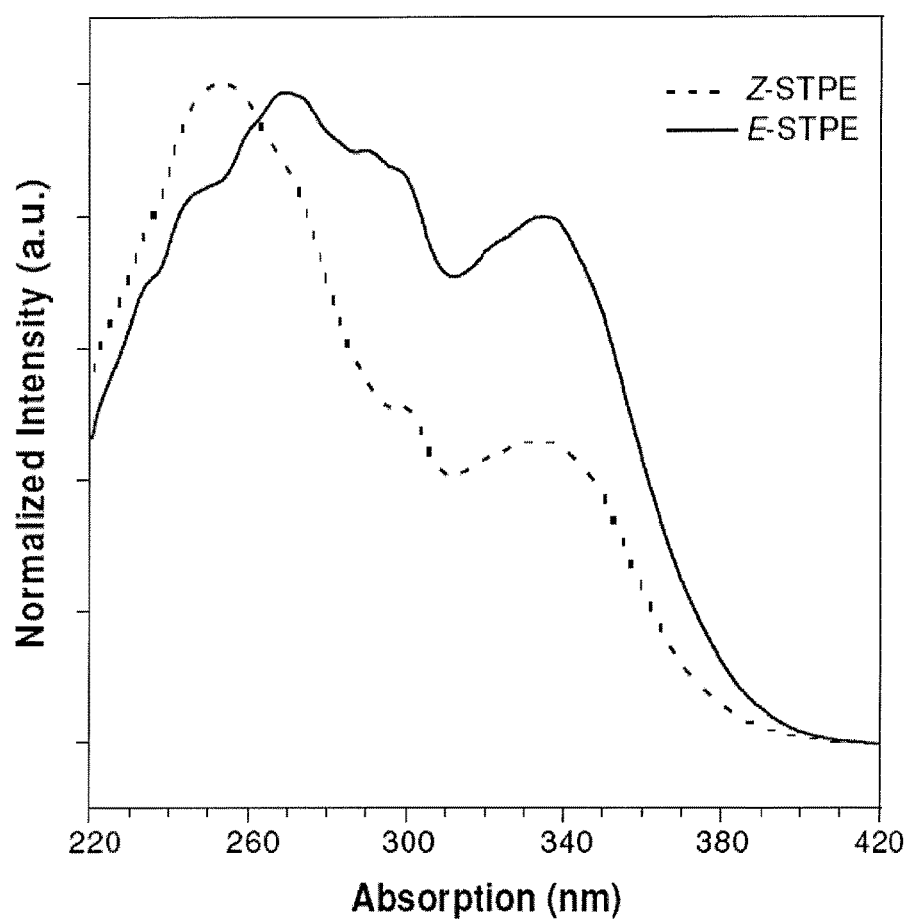
FIG. 12 shows the normalized absorption of STPE isomers in dry THF solution.

In one embodiment of the present application, the UV absorption spectra of E- and Z-STPE were studied, illustrations of which are shown in FIG. 12. The THF solution of the Z-isomer has a major absorption peak at 268 nm with a shoulder at 334 nm. The THF solution of the E-isomer has a blue-shifted main absorption peak at 252 nm and a relatively higher shoulder absorption at 344 nm compared with that of the Related to the conformation structure, in one it was seen that the Z-isomer is less conjugated than the E-isomer, as shown in FIG. 12.

The properties of STPE and OTPE are summarized in the Table below. The absolute fluorescent quantum yields of both compounds were measured by a calibrated integrating sphere. The quantum yield for STPE is 100% while that for OTPE is 69%, both suggesting high emission efficiency in the solid state.

| Properties of STPE and OTPE | | | | |
|---|---|---|---|---|
| Luminogen | $T_{95\%}$ (° C.) | $\lambda_{em}$ (nm) | $\Delta E$ (eV) | $\Phi_{F,A}$ (%) |
| STPE | 313 | 483 | 3.917 | 100 |
| OTPE | 357 | 463 | 3.935 | 69 |

Figure 13A:
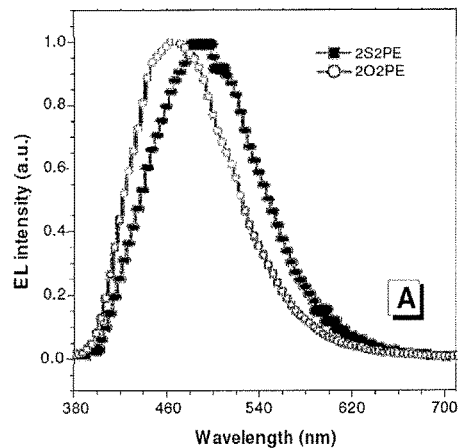
FIGS. 13A-D are graphical diagrams depicting fabricated OLED devices with OTPE and SITE.

[a]Abbreviation: $\lambda_{em}$ = emission maximum in THF/water mixture (1:9 v/v), $\Delta E$ = Energy gap predicted by computational calculation, $\Phi_{F,A}$ = absolute fluorescent quantum yield measured by a calibrated integrating sphere;

In some embodiments of the present subject matter, since STPE and OTPE are stable and AIE-active, the OLED devices were fabricated to test their electroluminescence (EL) properties. Unlike the conventional OLED device employing a guest and host combination mixture as the emitting layer, pure organic AIE-active compounds without doping luminogens can be achieved which perfectly solve the aggregation-caused quenching problem. The EL data is presented in FIG. 10. With the configuration of ITO/NPB (60 nm)/Dye (20 nm)/TPBi (10 nm)/Alq$_3$ (30 nm)/LiF (1 nm)/Al (100 nm), good performances were obtained with STPE in the bluish green region. In one embodiment, as shown in FIG. 13A, the EL spectra of STPE and OTPE were observed at 488 nm and 468 nm, respectively.

Figure 13B:
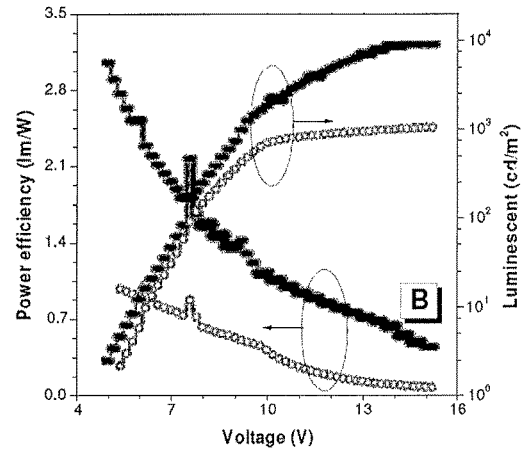
Figure 13C:
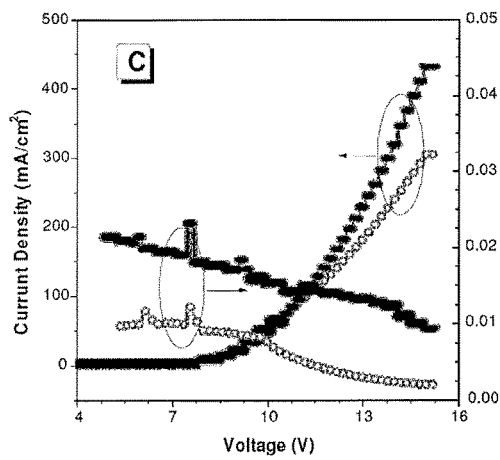
Figure 13D:
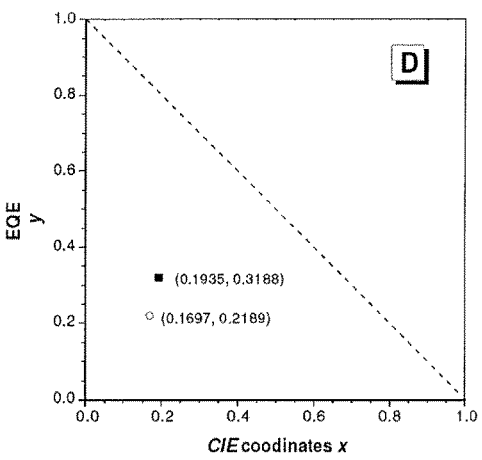

In some embodiments, on performing the EL study it was seen that STPE shows better brightness of up to $10^4$ cd/m$^2$, which is about one order of magnitude higher than that of OTPE (FIG. 13B). The turn on voltage to 1 cd/m$^2$ of both materials is about 5 V. The power efficiency (PE) and external quantum efficiency (EQE) are separately plotted in FIGS. 13C and 13D. STPE obviously had good EL performance, with an EQE value about 2%, which is more than two-fold higher than that of OTPE. The PE of the STPE device is about 3.0 mA/W while that of OTPE is less than 1.0 mA/W. Due to the high thermal stability of STPE, the device shows strong resistance to high voltage. However, in another embodiment, it was seen that OTPE is less stable under high voltage conditions compared with STPE. The PE and EQE of OTPE drop to 0 mA/cm$^2$ and 1 cd/m$^2$ above 10V, respectively.

By recalculating the EL spectrum, in one embodiment, the chromaticity diagram coordinates were obtained from the Commission internationale de l'éclairage (CIE) 1931, which is (0.1935, 0.3188) for STPE and (0.1697, 0.2189) for OTPE, respectively (FIG. 10D). With the CIE 1931 standard chart, it is possible to ascertain the color regardless of the ambient brightness because the luminance intensity is not considered in this xy-coordinate but only the chromaticity. According to the CIE 1931 standard, red (R) green (G) blue (B) and white (W) are defined as (0.64, 0.33), (0.30, 0.60), (0.15, 0.06) and (0.3127, 0.3290), respectively. From this chromaticity coordinates, x and y values represent the red emission fraction and the green emission fraction of measured light, respectively. In this case, the OTPE molecule shows an x value of 0.1697, close to the standard blue color x value (0.15), but its y value (0.2189) is much higher than the standard blue y value of 0.06. Thus, it gives a green light mixed with blue emission that matches the emission from the PL and EL measurements. The OTPE spectrum thus has a tail in the bluish green region.

The same trend is observed for STPE, which is red-shifted from OTPE as an emitter in an OLED device. The CIE 1931 coordinates' values calculated for STPE shows that the y value is 0.3188. This is a net enhancement compared with 0.2189 of OTPE. It nears the standard red color y value of 0.33, while the x value was not changed much by changing oxygen for sulfur.

The Table below shows the EL properties of STPE and OTPE.

| emitting layer | $\lambda_{EL}$ (nm) | $L_{max}$ (cd/m$^2$) | $\eta_{P,max}$ (lm/W) | $\eta_{ext,max}$ (%) | CIE (x, y) |
|---|---|---|---|---|---|
| STPE[I] | 488 | 9102 | 3.1 | 2.1 | 0.19, 0.32 |
| OTPE[I] | 464 | 1033 | 0.97 | 0.96 | 0.17, 0.22 |
| E-STPE[II] | 504 | 5523 | 1.3 | 1.0 | 0.23, 0.40 |
| Z-STPE[II] | 492 | 6626 | 2.0 | 1.7 | 0.20, 0.34 |

[a]Device configuration: [I]First time ITO/NPB (60 nm)/emitter (20 nm)/TPBi (10 nm)/Alq$_3$ (30 nm)/LiF (1 nm)/Al (100 nm), [II]Second time ITO/NPB (60 nm)/emitter (20 nm)/TPBi (10 nm)/Alq$_3$ (30 nm)/LiF (1 nm)/Al (100 nm)
Abbreviation:
$\lambda_{EL}$ = EL maximum,
$V_{on}$ = turn-on voltage at 1 cd/m$^2$,
$L_{max}$ = maximum luminance,
$\eta_{P,max}$ = maximum power efficiency,
$\eta_{ext,max}$ = maximum external quantum efficiency, and CIE = CIE 1931 color space coordinate.

E/Z isomers of STPE were successfully isolated in a large scale and their EL behavior was tested respectively, as shown in FIG. 14. According to the EL spectrum, the emission of the E-isomer is red-shifted from the Z-isomer. It matches the calculation results that the Z-isomer has a "V"-shape conjugation while the E-isomer has a linear conjugation. A small red shift on the EL spectra of the E-isomer is thus observed. In addition, better EL performance is observed from the E-isomer with longer conjugation when fabricated into the device, in terms of both the brightness and the efficiency (FIG. 14B). This is the first EL device study based on the E/Z isomers as the emitting layer material.

Synthesis and Development of AIE Luminescent Materials Containing DBT

In one embodiment, novel ethane derivatives functionalized with DBT units have been synthesized through the McMurry coupling reactions. In this embodiment, a new method of synthesis has been developed such that a TPE core is synthesized using DBT and DBF as building blocks to develop structures with AIE properties.

In another embodiment of the present application, a one-pot method of synthesizing an aromatic ketone derivative comprising: (a) reacting a carboxylic starting material of formula I with thionyl chloride and DMF to obtain Ar$_1$-carbonyl chloride, wherein Ar$_1$ is selected from the group consisting of toluene, methoxyphenyl, and halogenated phenyls; and (b) reacting Ar$_1$-carbonyl chloride with DBT under DCM reflux to obtain an aromatic ketone derivative of Formula II, wherein Ar$_2$ is DBT;

wherein Formula I is:
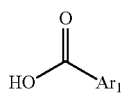
and wherein Formula II is:
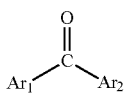
In another embodiment, Formula II above is TPA-CO-DBT.
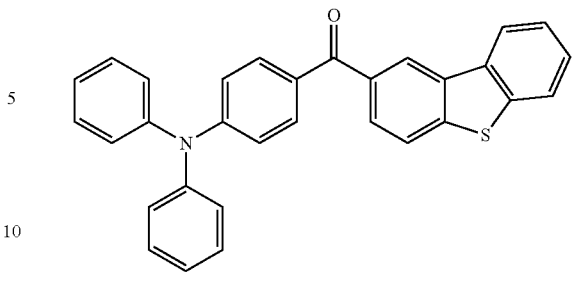
TPA-CO-DBT
In some embodiments, the various TPE-derivatives that are made from the one-pot method of synthesis are MxSTPE, TSTPE, NSTPE, and DiCyano-DBTPE, the structures of which are shown below.
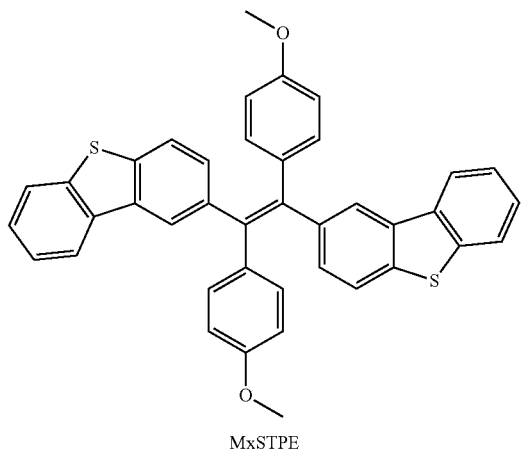
MxSTPE
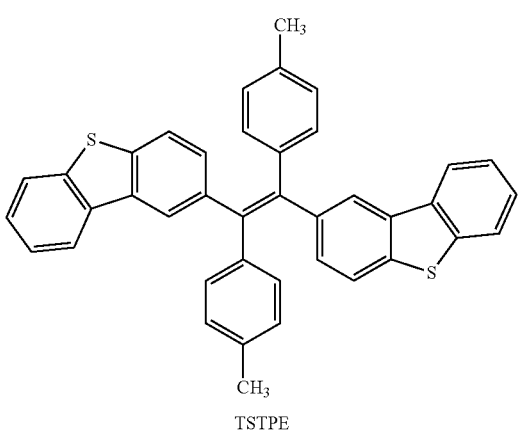
TSTPE
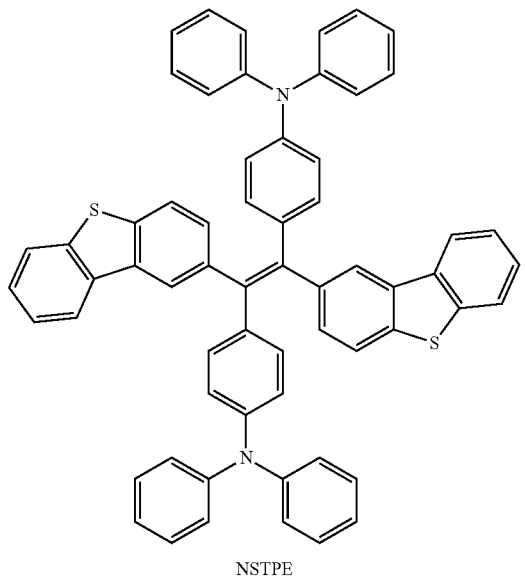
NSTPE -continued

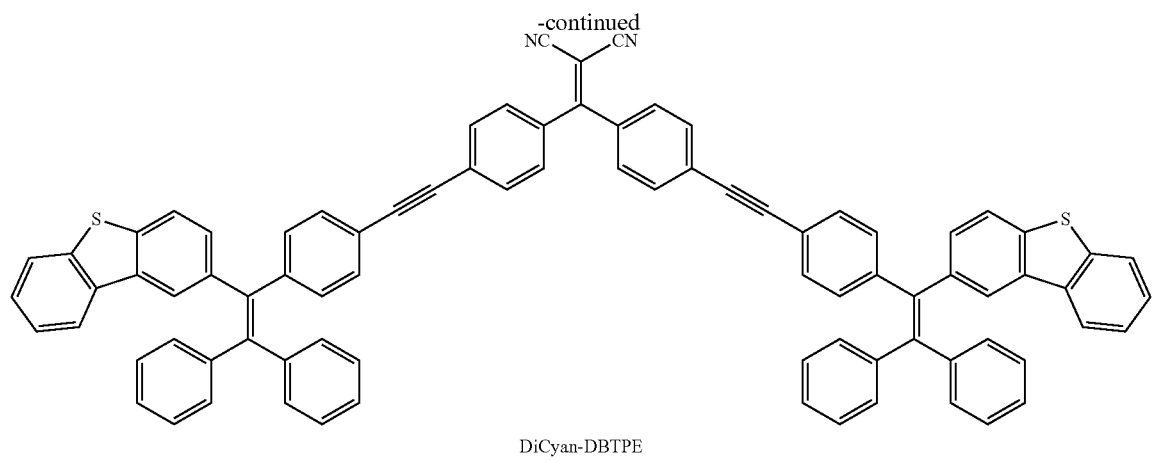

DiCyan-DBTPE

In another embodiment, when the TPA-CO-DBT that is synthesized from the one-pot synthesis method is subjected to TMF reflux, compounds such as MxSTPE, NSTPE, TSTPE, and DiCyan-DBTPE are obtained. The TPA-CO-DBT composition, therefore, is used as a building block to synthesize various TPE-derivatives. This approach to synthesizing TPE-derivatives using TPA-CO-DBT as a building block is novel, and at the same time economical.

Further, in another embodiment, TPA-CO-DBT exhibits a powerful emission under UV light. Further, in some embodiments, it has been seen that TPA-CO-DBT emits light in the bluish-green wavelength of 480 nm. In other embodiments, the TPA-CO-DBT composition in a methanol and water mixture system behaves like an AIE luminophore.

In some embodiments, it is seen that the TPE-derivatives that are synthesized from the TPA-CO-DBT core emit light, as far into the red region of the light spectrum.

In one embodiment, a TPE derivative composition having a luminogen exhibiting AIE properties is disclosed comprising: at least one luminogen having a backbone structure:

wherein each R and R' are independently selected from the group consisting of H, alkyl, unsaturated alkyl, heteroalkyl, cycloalkyl, heterocycloalkyl, aryl, and heteroaryl; and wherein each X is independently selected from the group consisting of O, S, Se, Te, C, Si, Ge, P, As, and Sb.

In some embodiments, the at least one luminogen attaches to a second luminogen via a spacer molecule, which is selected from the group consisting of a carbon single bond, a carbon double bond, a carbon triple bond, or a combination thereof. In another embodiment, the groups R and R' are either TPE or s-TPE. Further, in some embodiments, the TPE composition is DiCyan-DBTPE, the formula of which is below:

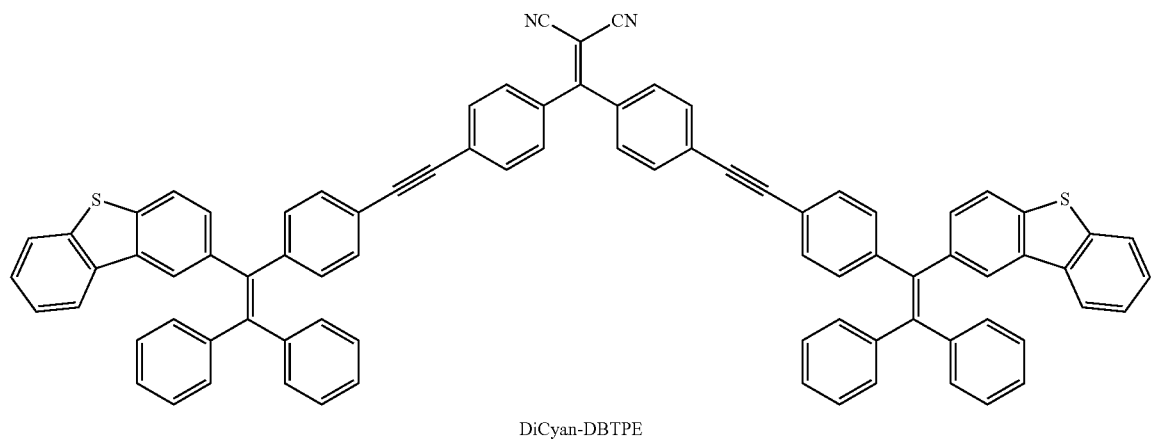 [SMILES: N#CC(C#N)=C(c1ccc(C#Cc2ccc(C(=C(c3ccccc3)c3ccccc3)c3ccc4sc5ccccc5c4c3)cc2)cc1)c1ccc(C#Cc2ccc(C(=C(c3ccccc3)c3ccccc3)c3ccc4sc5ccccc5c4c3)cc2)cc1]

DiCyan-DBTPE

In some embodiments, it is seen that DiCyan-DBTPE emits a light closer to the red wavelength when placed in a mixture of THF and water.

Uses of the DiCyan-DBTPE composition are in forensic studies, such as fingerprint detection. In some embodiments, DiCyan-DBTPE is synthesized in powder form so that it can be used on fingers.

In the field of organic photovoltaic (OPV), thiophene and its derivatives are considered to be excellent materials for absorbing solar light and also electron-rich conjugated systems in its oligomer form and polymer structures. Dibenzothiophene (DBT) is considered as a more planar poly aromatic hydrocarbon structure than thiophene and its electronic properties have been shown to be better than that of thiophene. Due to the electronic affinity of sulfur being higher than oxygen, dibenzofuran (DBF) is another upgraded compound candidate for OLED application and device design print detection.

Specifically, with respect to the "one-pot" synthesis, the reaction can be understood further by the reaction, as shown below:

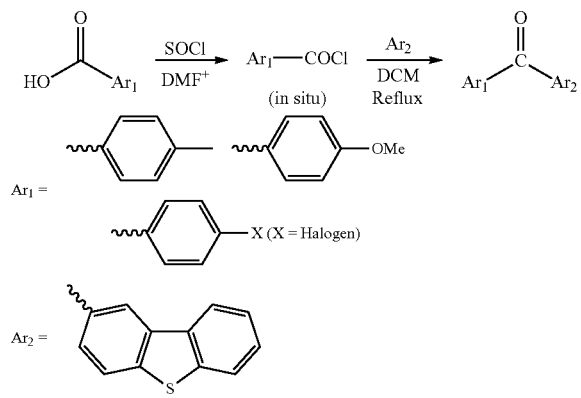

"One = pot" synthesis scheme of ketone derivatives by carboxylic stating materials In some embodiments, the aromatic compound DBT as Ar₂ were fixed on the second step while the Ar₁ was varied between toluene, methoxyphenyl, and halogenated phenyls. Careful consideration needs to be taken while choosing the Ar₁ moities as they need to be tolerant to SOCl₂. In one embodiment, the reaction can be pushed towards completion in only two hours if two drops of DMF are added to the mix before refluxing with thionyl chloride. When the refluxing solution becomes transparent, the reaction is deemed to be complete. Some carboxylic acids have a low melting point and are easily melted at the refluxing temperature. This renders the transparency observation mentioned above useless. In most embodiments, these reactions were refluxed for a little more than two hours to ensure completion.

In an embodiment of the present application, studies on TPA-CO-DBT were performed to analyze whether TPA-CC-DBT behaves like an AIE or ACQ compound using a THF/water mixture. It was surprisingly found in one embodiment that TPA-CO-DBT enjoys not a single, but two separate processes upon increasing water fraction, which is further differentiated into two sets. In some embodiments, the first process is an emission quenching along with a red shift, shown in FIG. 15A; the other is an emission enhancement with a blue shift, shown in FIG. 15B.

Figure 15A:
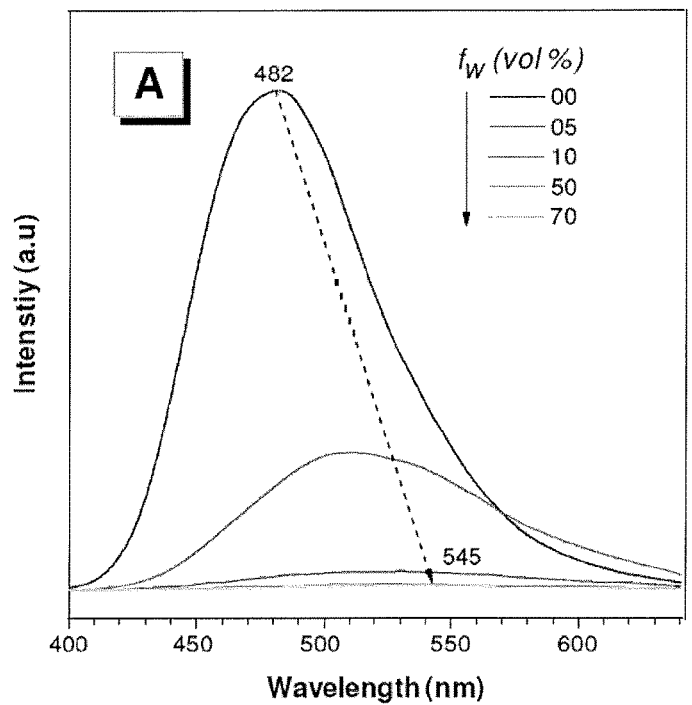
FIGS. 15A and B are graphical diagrams depicting the PL Spectrum of TPA-CO-DBT emission.
Figure 15B:
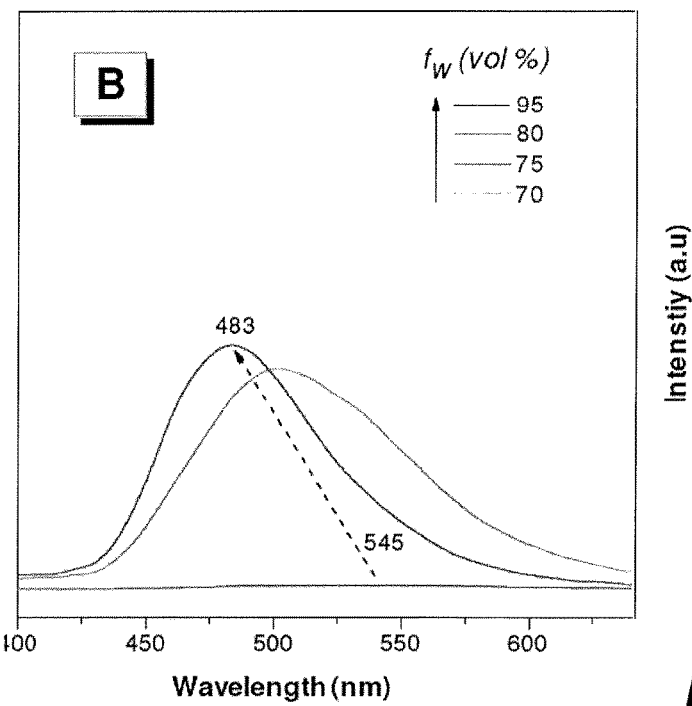
FIG. 15B shows the PL Spectrum TPA-CO-DBT emission quenching process enhancement process (from vol. 70% to 95%) as the water fraction increases.

FIG. 15A shows a red shift when the water fraction is increased. Starting from 482 nm in the pure THF solution, the 5% water fraction mixture system emission shifts more than 20 nm. In some embodiments, it was seen that the relative intensity is quenched to half of the intensity value of the pure THF solution. In another embodiment, it was observed that the most important phenomenon is the quenching effect for the 5% water in THF solution when compared to the pure THF solution. This result is explained by the polarity increase in the solvent which is close to the TPA-CO-DBT's dipole moment, making the molecule rotate into a more planar conformation. The electron-donating part of the molecule became more conjugated with the electron deficient carbonyl group. In an embodiment, with higher water fractions, the intensity kept diminishing from 5% to 70% of water fraction. This was most likely due to the twisting intramolecular charge transfer (ICT) process.

In some embodiments, opposite to the ICT process, starting from 75% H₂O/THF, the intensity is recovered along with blue shifted back to 483 nm from 545 nm. This partial emission enhancement is typical of the AIE phenomenon. Due to the molecules aggregating in a high fraction of poor solvent environment along with the twisted molecular conformation resulting in poor internal conjugation at 90% water fraction, it blue shifts the emission rather than quenching it. Interestingly, in one embodiment, the peak shape of 8% H₂O/THF was seen to be abnormal; it was measured with a wider spectra but the tail covers the spectra of 90% H₂O/THF. In another embodiment, the molecular conformation of TPA-CO-DBT was twisted around itself so tightly that its emission upon UV excitation can be very powerful, following the RIR mechanism idea.

Figure 16A:
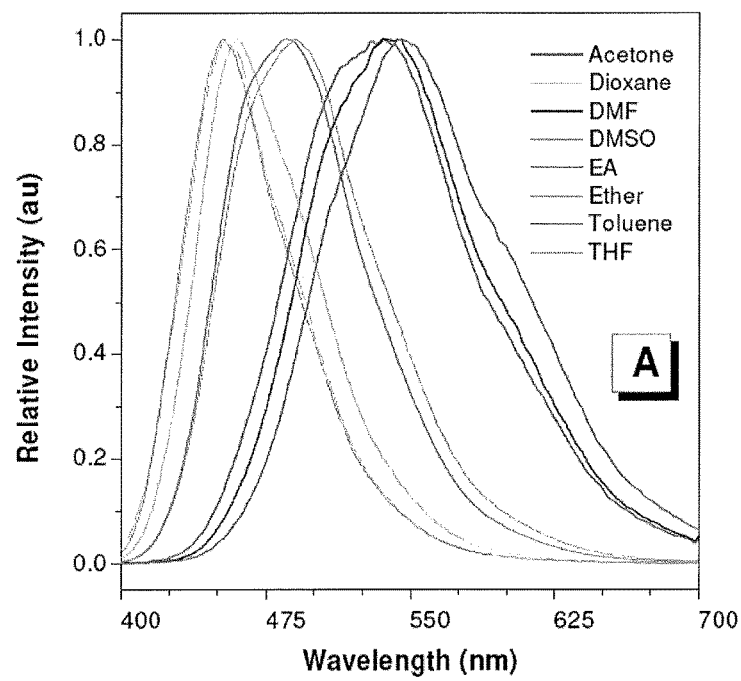
FIGS. 16A and B are graphical diagrams depicting the PL Spectrum of TPA-CO-DBT emission.
Figure 16B:
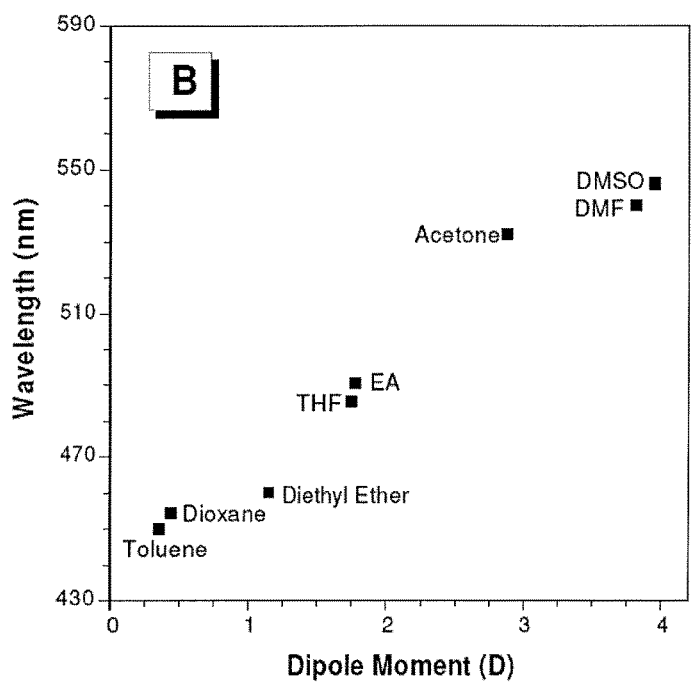
FIG. 16B depicts the PL Spectrum of TPA-CO-DBT emission versus different dipole moments of the solvent.

As FIG. 16A shows, in one embodiment, various solvents were investigated to study the luminescence properties of TPA-CO-DBT. For easier interpretation, the dipole moment is presented in ascending order from toluene to DMSO along the emission wavelength shift in FIG. 16B. A common way to classify solvents is to divide them between polar and non-polar ones with a subdivision for polar ones whether they are aprotic or protic. Here, it is possible to group toluene, dioxane, and diethyl ether into non-polar solvents and all the others as polar solvents. In one embodiment, the TPA-CO-DBT emission in non-polar solvent is shorter than 470 nm. In this embodiment, it was seen that with the molecule dissolved but no twist in the given non-polar low dipole moment solvent, the emission of TPA-CO-DBT is, therefore, blue as indicated by the twisted rigid conformation.

When the dipole moment becomes more polar (larger than 1.5 dipole moment), the solvent effect becomes apparent as the emission of TPA-CO-DBT shifts towards longer wavelengths. As indicated earlier, the increasingly polar environment around TPA-CO-DBT untwists its various subunits. The conjugation of the entire molecule becomes longer, explaining the red shift. By increasing the dipole moment of solvent, the released twisted subunits are less and less twisted, exacerbating the phenomenon.

In order to further study the behavior of TPA-CO-DBT in methanol, in one embodiment, its luminescence was studied with various fractions of water in MeOH. In some embodiments, with the water fraction increase, the emission intensity was enhanced especially after reaching 60% H₂O in MeOH. But the 90% showed an intensity drop due to TPA-CO-DBT precipitating. This entire data set demonstrates that TPA-CO-DBT in a methanol and water mixture system behaves like a typical AIE luminophore. In another embodiment, as the water is added to the methanol solution of TPA-CO-DBT, the emission is enhanced and the emission peak is at 480 nm. The bluish green emission wavelength of 480 nm suggests that the twisted conformation is the one present in the aggregates formed in the emissive solution. Therefore, all protic solvents that can dissolve TPA-CO-DBT were tested. In some embodiments the selected solvents were methanol, ethanol, isopropanol, and acetic acid, all of which have a hydroxyl group that can exchange hydrogen atoms. Triethylamine was also tested since amine groups can also kill emission of TPA-CO-DBT in the solution state for comparison. It was seen that all of these solvent mixtures presented AIE behavior, making TPA-CO-DBT a unique polar protic solvent for the AIE system.

Figure 17:
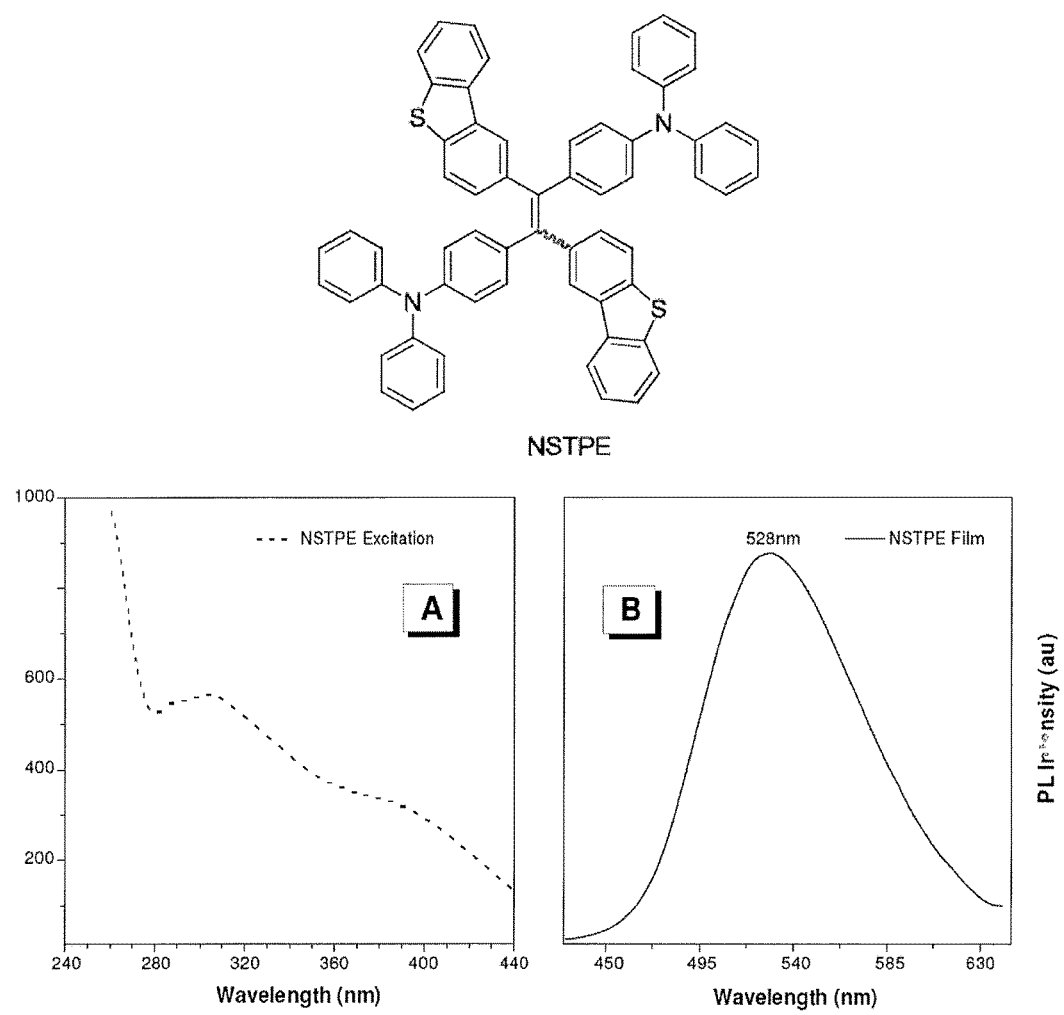
FIG. 17 shows the Excitation (A) and Emission (B) of the NSTPE spectrum.
Figure 20A:
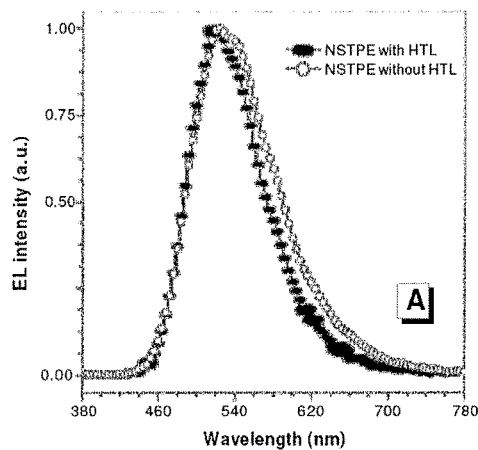
FIGS. 20A-D are graphical diagrams depicting fabricated OLED devices with NSTPE with (square) and without (circle) of hole transporting layer.
Figure 20B:
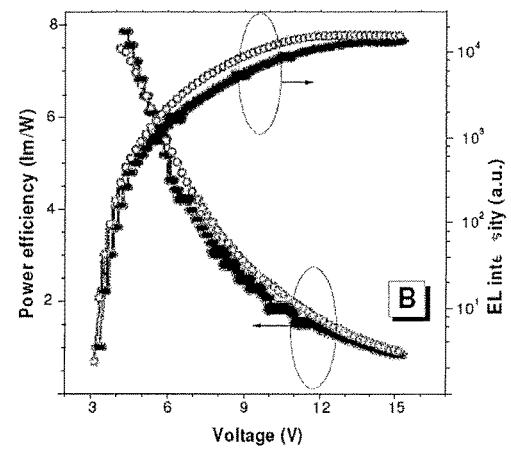
Figure 20C:
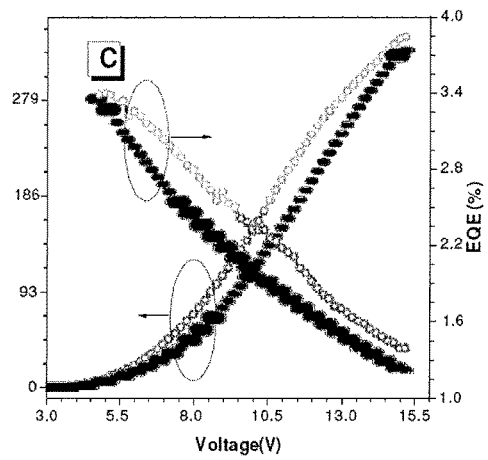
Figure 20D:
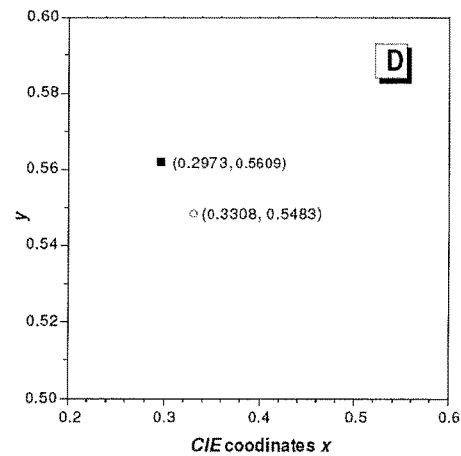

In an embodiment, the solid-state sample was cast in a film and the PL was measured, as shown in FIG. 17. With the excitation covering from 300 nm to more than 400 nm, the emission of NSTPE film had its maximum emission at 528 nm indicating it is a green AIE material. The fact that the film excitation covers a wide spectrum is believed to be caused by the solid state physical interactions which are fixed and the twisted angles of the molecules are restricted in the aggregated form. Therefore, the ground state of the material can be excited by different wavelengths corresponding to various restricted degree of solid state luminogenic molecules.

The solution state photoluminescence is reported in FIG. 18. In one embodiment, the faint emissive solution state is kept at 60% THF/water fraction mixture. In this embodiment, it was seen that with a higher water fraction, luminescence started to emit more intensely after 60% water fraction, then the intensity kept increasing until 80% THF/water fraction was reached. However, a minor drop of the maximum intensity was obtained with an even higher water fraction as shown in FIG. 18B; the decreased intensity of the sample was believed to be due to the precipitation in the hydrophilic THF/water solution. When comparing the emission maximum wavelength with the solid state film photoluminescence, the maximum wavelength was not shifted significantly. However, in some embodiments, a blue shift of the maximum emission from 70% water fraction solution to 80% water fraction solution was clearly observed. This is a typical AIE behavior. Again, the RIR explains how the overall conformation is so twisted that the internal conjugation is shortened. Thus, the conjugation structure is disrupted and the electronic donor part has poor communication with the rest of the molecule, reducing the donor-accept effect and producing the blue shift spectra.

In one embodiment, to better understand the conjugation structure of the molecule NSTPE, the UV-vis absorption was measured and the data is plotted in FIG. 19. The major peak at 311 nm is the core tetraphenylethene (TPE) absorption while the shoulder at 375 nm corresponds to the D-A conjugation absorbing energy. Noteworthy, the absorption shape of the spectra varies from the excitation in FIG. 17A to the excitation maximum peak in FIG. 19. However, the main peak at the shorter wavelength is relatively absorbing higher intensity than the shoulder. The reason behind this is that the molecules in the solution are well dispersed and rarely interact with each other. In some embodiments, the conjugation chain of NSTPE is confirmed by the shoulder peak at the wavelength of 375 nm. Good electron communication between the triphenylamine and the dibenzothiophene moieties could explain this. When all the building blocks are polyaromatichydrocarbons (PAH), the electron properties are believed to be promising when fabricated into a device.

In one embodiment, the electroluminescence (EL) measurements are based on the organic light-emitting diodes (OLED) device fabrication, with the configuration of ITO/NPB-HTL (60 nm)/Dye (20 nm)/TPBi (10 nm)/Alq$_3$ (30 nm)/LiF (1 nm)/Al (100 nm). In some embodiments, the electroluminescent NSTPE device emits at the wavelength of 520 nm. With the pure NSTPE as the emitting layer and no other luminogen as dopant, the EL resulted in a brightness of $10^4$ cd/m$^2$. So far this NSTPE device is the best one in the TPE family with a standard layers configuration. The power efficiency is around 8.0 lm/W while the external quantum efficiency is measured at about 4%. To follow up on these good results and given the well-known hole transporting property of triphenylamine, the reducing hole-transporting layer (HTL) version of the device was made (circle dots, FIG. 20). Being so clearly above the square dots, the circle dots, without HTL, are indicating a significant improvement in power efficiency and external quantum efficiency, but also in current density versus voltage.

On the other hand, the EL spectra without HTL (FIG. 20B) is broader compared to the standard configuration device. The main reason for this is that the NPB as HTL with a 60 nm thickness is partially absorbing the EL generated light and makes the spectra of the standard configuration device covering a narrower spectrum. This is believed the reason for the low device efficiency. The CIE coordinates of both devices are plotted in FIG. 20D. With the x axle representing the red intensity and the y representing the green intensity, the CIE graphic shows that the device emission with HTL is located with higher y and lower x values than the emission from the device without HTL. Then, the absolute color of the spectrum of the device with HTL is greener than for the device without HTL. In the device without HTL, less light is blocked by the fabricated layer so the original green light is balanced with a more powerful red emission measured (x value increased), thus making the CIE coordinate less green, with a lower y value. In order to compare the EL and PL spectrum, the maximum emission wavelength was not varied significantly.

Figure 28:
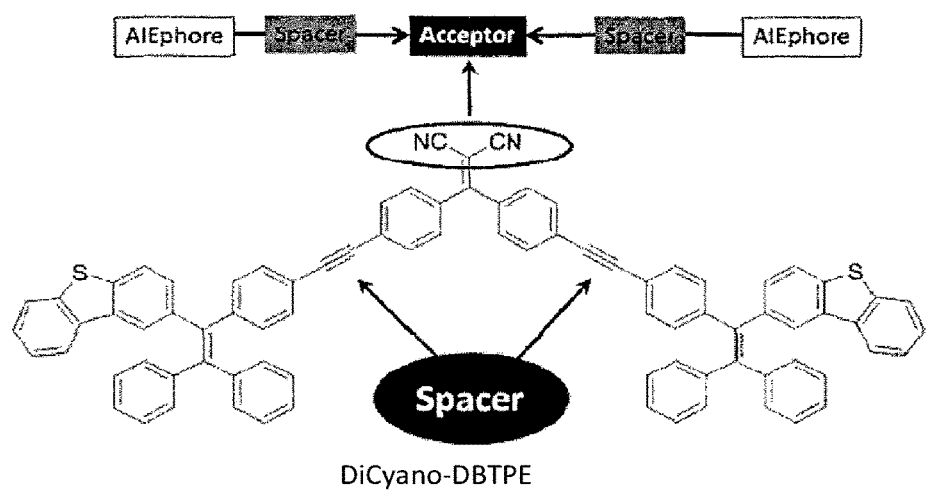
FIG. 28 shows certain new structures derived from DBT emitting in the red region.

In some embodiments, while AIE-active NSTPE emits in the green region, AIE-active materials with longer emission wavelengths would be much more attractive in real applications. Therefore, further the study of DBT derivatives to include new structures derived from DBT emitting in the red region have been synthesized, as shown in FIG. 28.

In one embodiment, the structure of DiCyano-DBTPE is divided into three parts: electron-acceptor, spacer, and AIE luminogen to boost the AIE property. The electronic withdrawing ability of the dicyano group is high and also improving the electron communication by pulling electrons to its electronic deficient site. Since the STPE with two dibenz othiophenes (DBTs) moieties was proven to be AIE-active, it establishes that the AIE luminogen with one DBT moiety is AIE-active.

In an embodiment, the two terminal AIE luminogens are passively pushing the electrons to the center. In most embodiments, a symmetrical structure is employed here for several reasons. First, this structure counter-balances the possibility that the weak electron donating group (AIE luminogen) has to extend the electronic cloud to the center di-cyano core site at the same time. The reason the AIE luminogen is counted as a weak electron donor is because of the center electron, which has a withdrawing ability that induces the entire AIE luminogen as a weak electron donor. Further, a symmetric structure has better resistance that effects solvents when they emit light.

Figure 21A:
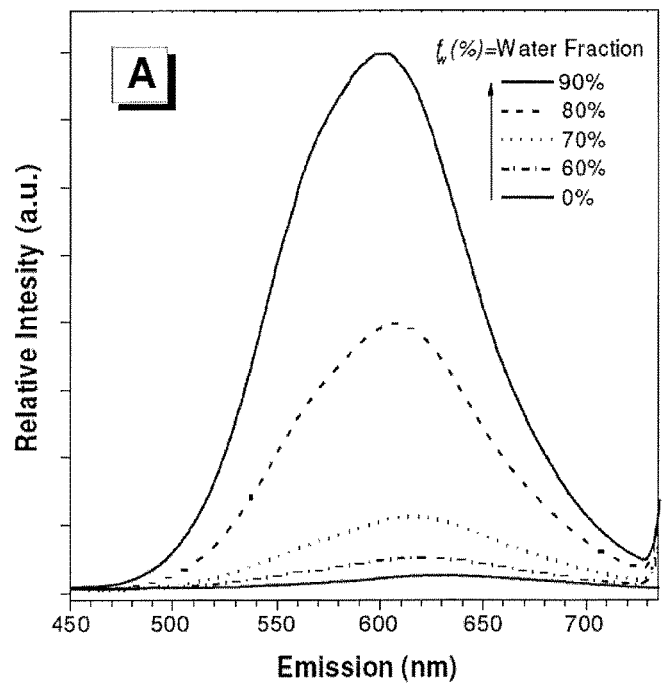
FIGS. 21A and B are graphical diagrams depicting PL spectra of DiCyano-DBTPF in THF and THF/water mixtures with different water fraction.
Figure 21B:
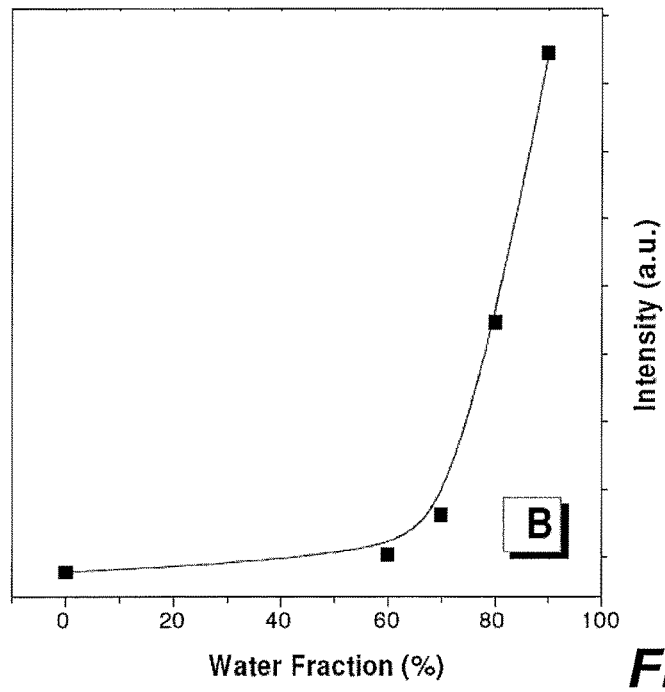
FIG. 21B depicts change of PL intensity of DiCyano-DBTPE at water fraction in THF/water mixture. Dye concentration: 20 µM; excitation wavelength: 360 nm.

In a preferred embodiment, the desired structure was obtained and the photoluminescent properties were studied (FIG. 21). FIG. 21A shows that water addition to the solution of DiCyano-DBTPE enhances the intensity of the emission of the THF/water mixture solution starting from the 60% water fraction sample. By keeping the concentration as low as $10^{-5}$ M, the intensity is increased until the 90% water fraction sample, touching the roof of the spectrum. No drop of the intensity is directly pointing out that this dye behaves in a fashion typical of the AIE phenomenon (shown in FIG. 21B). Upon water addition, a small blue shift can be observed and it is easier to interpret the shifting of the emission in FIG. 22.

Figure 22:
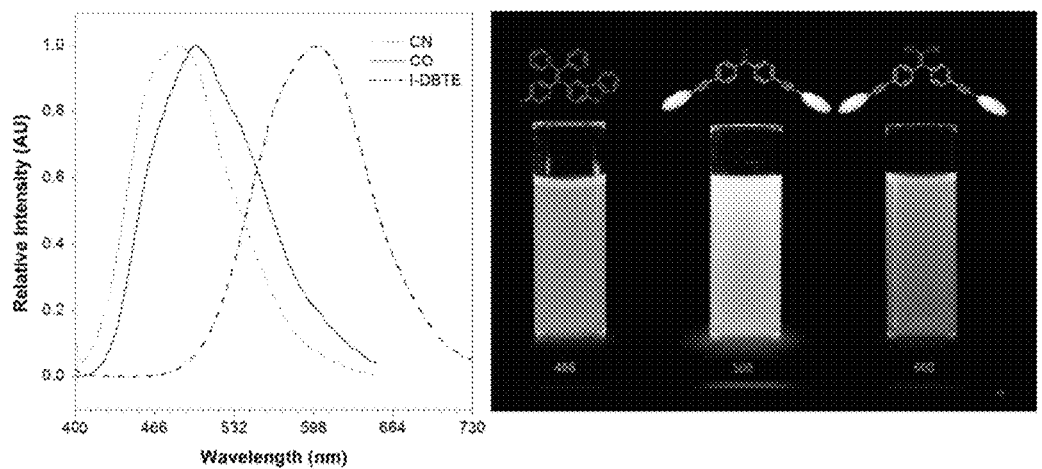
FIG. 22 shows PL (left panel) emission shift of different structures (right panel) photography of the AIE molecules involved in synthesizing DiCyano-DBTPE.

In FIG. 22, another embodiment shows that DiCyano-DBTPE samples are taken under 365 nm excitation. The emission is enhanced with the water fraction increasing from left to right. The non-emissive vial with faint light is positioned on the left and no emission is observed till the water fraction reaches 60%. However, at 70% water fraction a more red light emission can be seen as compared to the sample having a water fraction at 80%. Further, at a 90% water fraction, a shorter wavelength shift can be seen. In this embodiment, it was noticed that at 80% water fraction, the light emitted was in the red region, and at 90% water fraction, the light emitted was clearly in the orange region.

Figure 23:
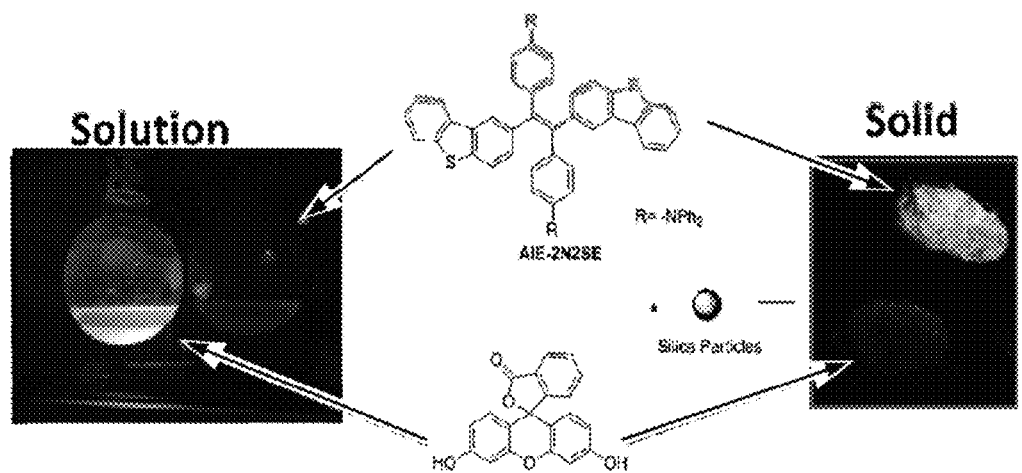
FIG. 23 illustrates the manufacture procedure of fingerprint detecting AIE powder

Additionally, in one embodiment of the present application, AIE powder was manufactured. In some embodiments, AIE exhibiting luminogens are highly advantageous in revealing human grease, and therefore can be used in forensic analysis/latent print analysis. Since human grease is abundantly expressed on the surface of everyone's fingers, such trace amounts of bio waste can be used as raw materials for detection experiments. In order to prove the advantages of the material's solid state luminescent properties, the fluorescein with the same molecular concentration was applied in a control experiment as shown in FIG. 23. The fluorescein was a typical dye to make aquatic media fluorescent, but it was an ACQ dye with no emission in the aggregated state. As shown in FIG. 23, when fluorescein was dissolved in the flask, it was highly emissive. It however turned non-emissive when the particles formed after evaporation of the solution. On the other hand, the AIE material that was selected was emissive after the fingerprinting powder was produced. Further, on measuring the difference of the photoluminescence of both materials, it was found that a difference of more than 300 fold was seen in the intensity between the ACQ and AIE materials.

Figure 24:
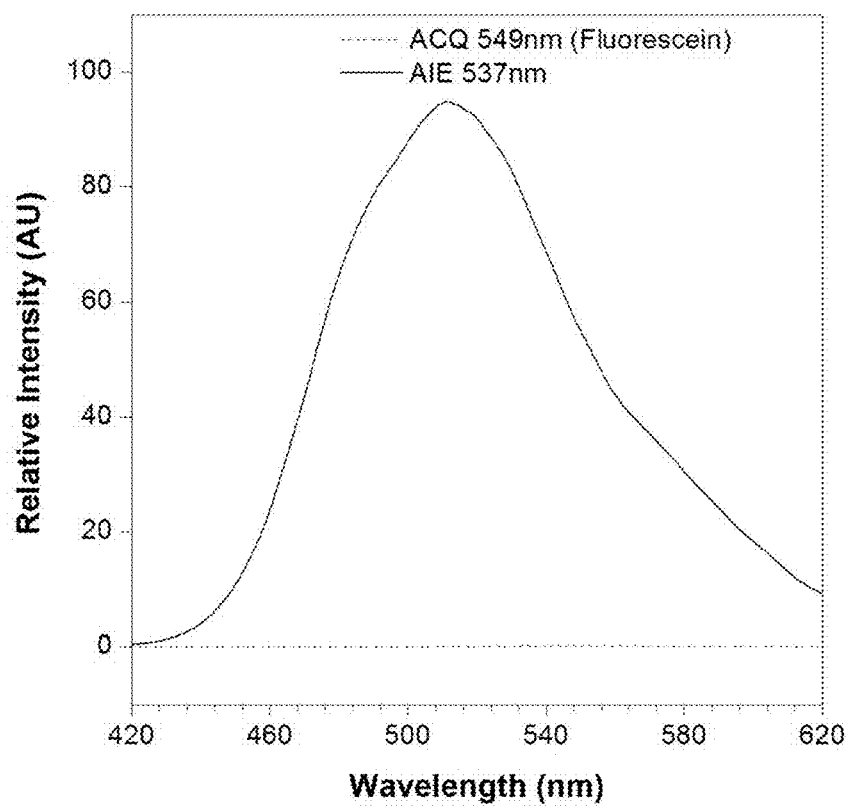
FIG. 24 depicts a PL spectrum of ACQ and AIE dye (NSTPE) compared in solid state sample.

For a better comparison, the photoluminescence of both ACQ and AIE materials were measured. The powder loaded with ACQ and AIE dye each is filled with quartz cell with the fixed height and laid in the reflection site on the optical way. A difference of more than 300 folds in the intensity between the ACQ and the AIE was observed, as shown in FIG. 24. This result is unexpected because the nature of the ACQ dyes itself and its self-quenching property in the aggregated state. The AIE mechanism is promising for such signal amplifications to enhance the resolution of the fingerprint images.

Figure 25:
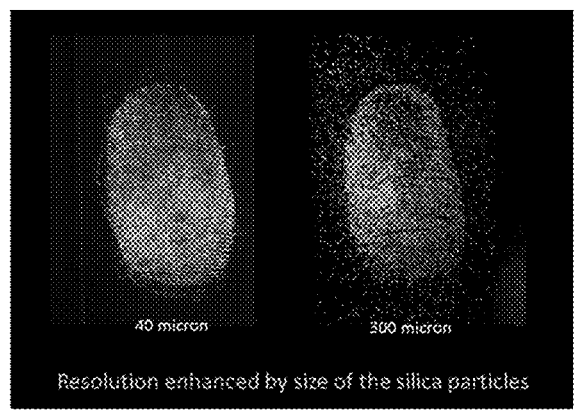
FIG. 25 shows a comparison of the resolution of fingerprints based on the size of AIE material used.

In one embodiment, it was found that the particle size of the AIE active materials should be kept smaller than the size of the human fingerprint ridges, as shown in FIG. 25. The AIE-active 300 micron particles stained the latent pattern were recorded, but the relevant details could barely be seen with only the shape of a finger. The powder was gently applied on the surface to be investigated and after shaking the object, the AIE-active material attaches to the grease of the fingerprint forming a clear white pattern. After the excess powder is shaken off, the fingerprint image is obtained within seconds, and due to the high intensity of the light that is being emitted, any cell phone camera can be used to take and send the picture of the fingerprint for further analysis.

Composition and Synthesis of Aggregation-Induced Emission Materials for Triboluminescence and Chemiluminescence In one embodiment of the present application, a phenomenon called triboluminescence was studied. Triboluminescence is generated when the chemical bonds in crystalline materials are broken by crashing. This is of very high importance because triboluminescence obviates the need to use UV light as a source of excitation. This is highly advantageous because UV light has been known to be a carcinogen. In need of these novel luminogenic materials, a new family of organometallic complexes with aggregation-induced emission characteristics is synthesized. Further, in another embodiment of the application an easily controlled method to trigger luminescent materials to emit light has been developed by utilizing energy released from chemical reaction. Such kind of luminescence is known as chemiluminescence. In some embodiments of the present application, materials that are capable of solid state chemiluminescence is further discussed.

In one embodiment of the present application, an organometallic composition containing a luminogen with AIE properties and triboluminescence comprising: at least one luminogen having a backbone structure selected from the group consisting of

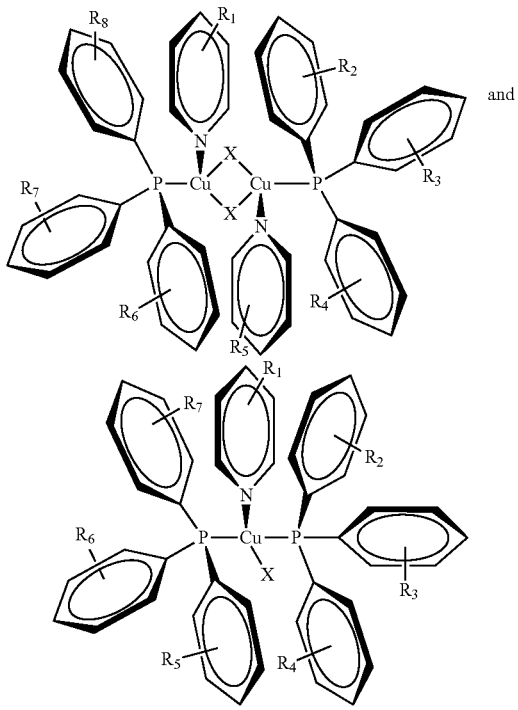

and wherein each $R_1$, $R_2$, $R_3$, $R_4$, $R_5$, $R_6$, $R_7$, and $R_8$ are independently selected from the group consisting of H, alkyl, unsaturated alkyl, heteroalkyl, cycloalkyl, heterocycloalkyl, aryl, and heteroaryl; and wherein each X is selected from the group consisting of F, Cl, Br, I, and At.

In one embodiment, the organometallic composition is a luminogen with AIE properties and triboluminescence comprising: at least one luminogen having a backbone structure selected from the group consisting of

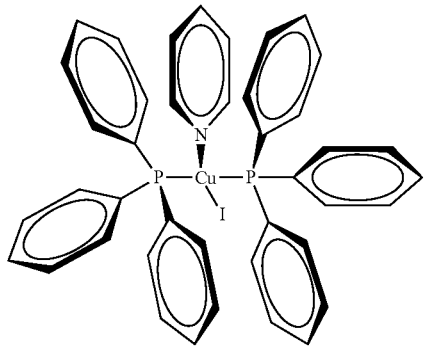

wherein each $R_1$, $R_2$, $R_3$, $R_4$, $R_5$, $R_6$, $R_7$, and $R_8$ are independently selected from the group consisting of H, alkyl, unsaturated alkyl, heteroalkyl, cycloalkyl, heterocycloalkyl, aryl, and heteroaryl.

In some embodiments, the organometallic composition is in crystalline form. Further, in other embodiments, the mechanochromic properties of the luminogen of the organometallic composition are exhibited when the composition is ground, and then quickly cooled from a melted state. In other embodiments, the organometallic composition exhibits triboluminescence when crystal of the composition are pressurized, fractured, or ground.

Further, in some embodiments, the present subject matter relates to a method of synthesizing an organometallic composition containing luminogen with AIE properties and tribolumescence, comprising: (a) reacting an diphenyl oxalated ester solution with hydrogen peroxide to obtain an with a four-membered ring; and (b) reacting the four membered ring with a dye such that an excited dye molecule is produced along with carbon dioxide wherein radiative relaxation of the excited state generates light emission. In some embodiments, NSTPE is used as a dye molecule, which emits a bluish-green light. Further, in other embodiments, during the synthesis of the organometallic compound, a cation and an anion are formed. Specifically, an anion is formed when the four membered ring is decomposed. In one embodiment, when the cation and anion are recombined, an excited NSTPE dye molecule is produced.

In further studying the concept of Triboluminescence, crystal structures of Cu(I)IPy(PPh$_3$)$_2$ (LX-1) and [Cu(I)IPy(PPh$_3$)]$_2$ (LX-2) were prepared. Methods of preparation of LX-1 and LX-2 are discussed in the examples below. Further, LX-1 and LX-2 were studied, and are represented by the formulae:

LX-1

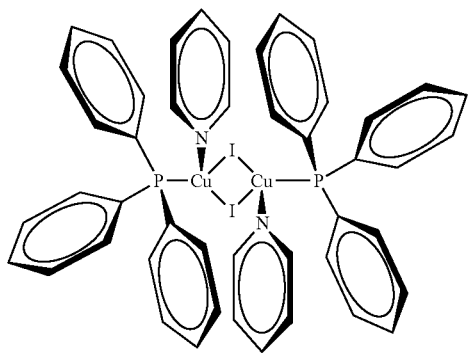

-continued

LX-2

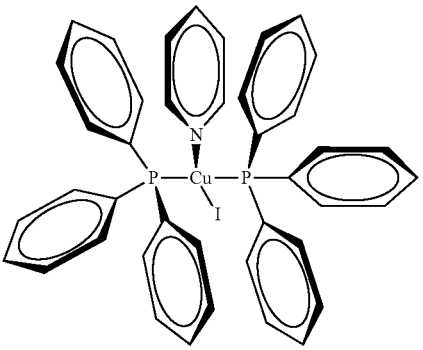

Figure 26A:
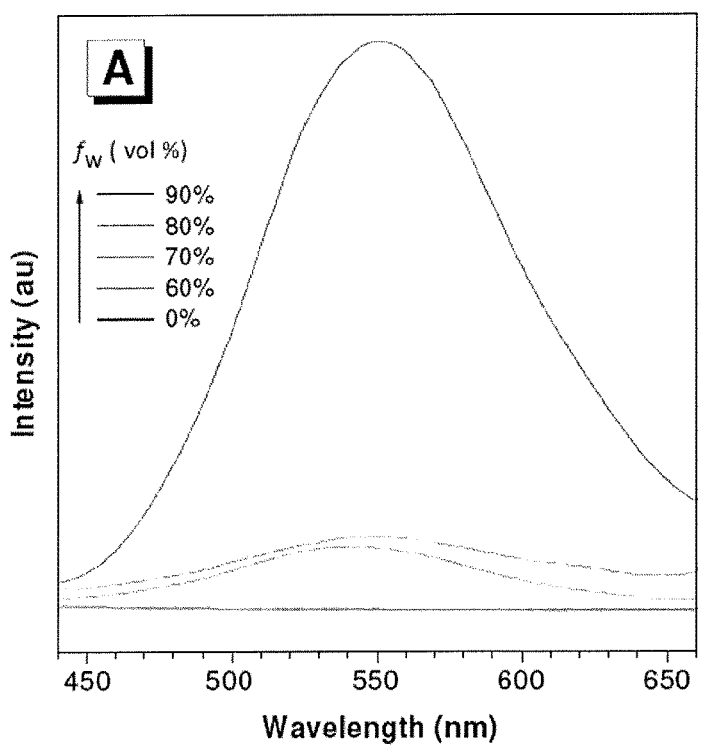
FIGS. 26A and B are graphical diagrams depicting PL spectra of LX-1 in pyridine and pyridine/water mixtures.
Figure 26B:
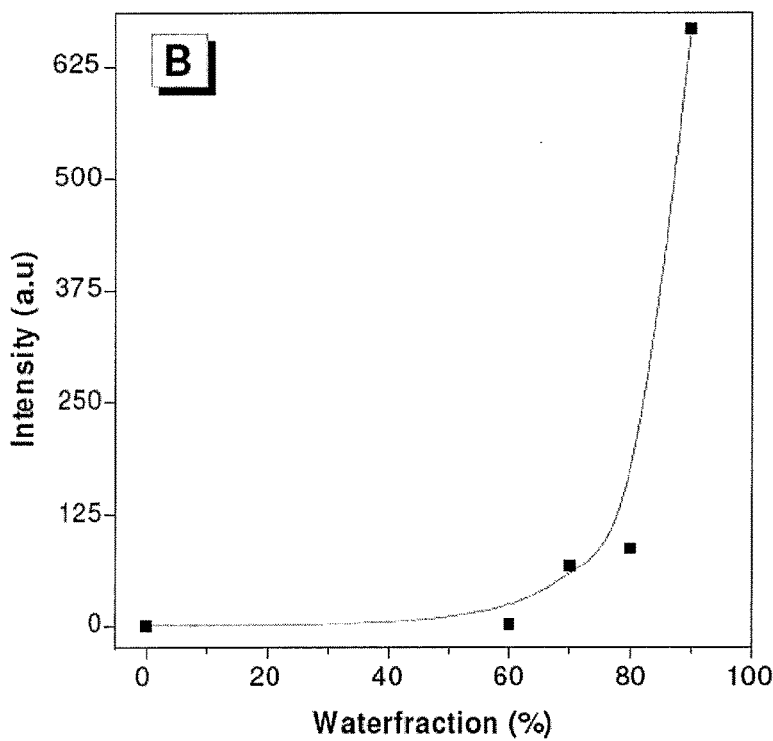
FIG. 26B shows change in PL intensity with the composition of the pyridine/water mixture of LX-1. Dye concentration: 20 µM; excitation wavelength: 360 nm.
Figure 27A:
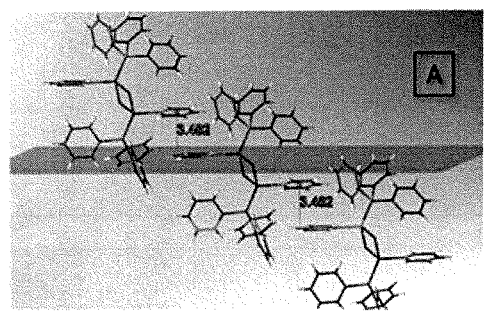
FIGS. 27A-D are graphical diagrams depicting π interaction in crystals.
Figure 27B:
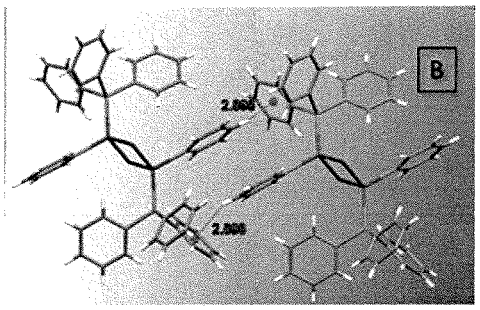
Figure 27C:
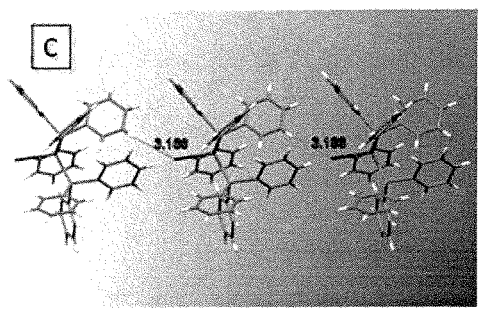
Figure 27D:
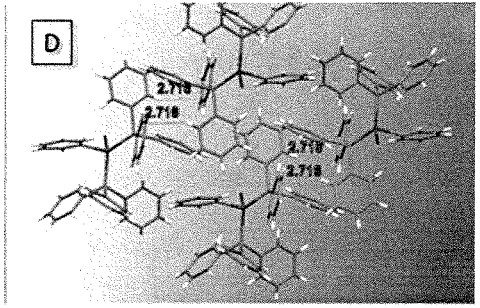

In one embodiment, PL studies on LX-1 showed that LX-1 is AIE active as shown in FIG. 26. As LX-1 is incapable of dissolving the THF, the PL study is performed in pyridine and its mixtures. In pure pyridine, LX-1 is non-emissive state, probably due to the triphenylphosphine and the pyridine rotors, which consume the energy of excited state through non-radiative relaxation channels. When aggregates form, these motions are restricted, thus enabling the excited state to decay radiatively. Aggregation starts to form in 80% pyridine/water mixture. Afterwards, the emission intensity starts to rise swiftly. At 90% water content, the emission intensity is more than 6-fold higher than that at 80% aqueous mixture.

In another embodiment, on studying the characteristics of LX-2, it was found that LX-2 emit faintly in the solution state. However, it was seen that it emits intensely in the solid state revealing that it was also AIE-active. Further, it was seen that the emission of LX-2 has a longer wavelength that allows it to be differentiated from LX-1.

Further, in an embodiment, on studying the crystal structure of LX-1 and LX-2, as shown in FIG. 27, intermolecular π-π stacking is found in between pyridine rings of LX-1 with distance of 3.482 Å. Instead of π-π stacking the proton of pyridine ring points its head to the nearest phenyl ring π. center of neighboring phenyl ring with intermolecular distance of 2.898 Å. Compared to CH-π interaction, the π-π stacking is much weaker in LX-1 crystals. A unique Cu—I•••H interaction with a distance of 3.168 Å was seen in LX-2. Even tighter intermolecular interaction is found among the phenyl rings of triphenylphosphine ligands. The proton of one phenyl rings interacts with the π center of neighboring phenyl rings with an intermolecular distance of 2.761 Å. No stacking between pyridine rings was found in LX-2. Due to this, it can be inferred that while LX-1 and LX-2 have no mechanochromic property, they are endowed with triboluminescence.

In one embodiment, it was seen that the loose packing of crystals of LX-1 endows it with novel mechanochromic property. In another embodiment, by simply grinding its crystals, its emission shifts by more than 70 nm, probably due to the disruption of the constraint posed by the crystal lattice, which now makes the molecule to adopt a more planar conformation. Since LX-2 possesses no such packing but a highly crowed structure, its crystal emits to show large emission shift upon grinding. Repeatable triboluminescence can be achieved by recrystallizing the crashed powder from pyridine solution.

The mechanism can be proposed as follows. Both triboluminescence and photoluminescence originates form the radiative decay of the excited state. Thus, the external forces elucidates similar as photon to pump the dye molecule to its excited state, whose radiative decay gives light emission. However, the energy generated by force is unknown. According to the structure of the LX-2, it exhibits multiple intermolecular Cu—I . . . H interactions with the distance of 3.168 A. These interactions are loss upon applying an external force, but on the other hand, induce charge separation due to the newly created tribological interactions at the molecular level. The copper (I) core generates hole by losing and electron, while the phenyl ring accepts the electron to become negatively-charged. When the Fe charges on the surface of the crashed site are recombined by pressure, an excited state is generated.

Since the non-radiative relaxation channels are blocked in the solid state by restricting the molecular rotation in AIE materials, it permits the excited state to decay to give bright emission. In one embodiment, no triboluminescence is detected in LX-1, probably due to its electron-poor copper (I) iodine bridge center, which is less likely to generate charge and hence excited state generation. Thus it was advantageously identified that copper (I) in LX-2 is essential for such phenomenon.

In one embodiment of the present application, materials that exhibited chemiluminesce and AIE properties were developed. Further, materials that possessed these properties in solid state were developed.

In another embodiment, the key species to trigger chemiluminescence of luminogenic material is discussed. DD (as shown in the reaction below) is regarded as a carbon dioxide dimer with high energy. In one embodiment, first, DD is achieved by reaction of oxalyl chloride and hydrogen peroxide, and second, the concentration of DD collected in a container and DD is then introduced to AIE materials. The experiment was simplified, and further explained in the examples below.

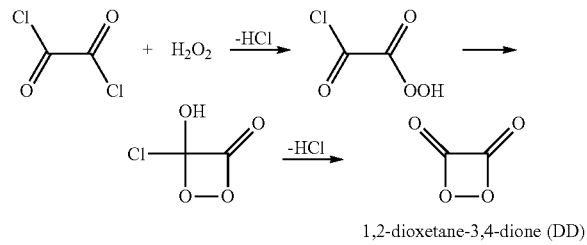

1,2-dioxetane-3,4-dione (DD)

EXAMPLES

Preparation of TPE and its Derivatives

Benzophenone, palladium on activated charcoal (Pd/C), zinc dust, dibenzosuberone and all the benzophenone derivatives were purchased from Aldrich and used without further purification. Tetrahydrofuran (THF) was freshly distillated on sodium benzophenone ketyl under nitrogen immediately prior to use.

$^1$H and $^{13}$C NMR spectra were measured on a Bruker AV 300 spectrometer in deuterated chloroform using tetramethylsilane (TMS; δ=0) as the internal reference. Absorption spectra were measured on a Milton Roy Spectronic 3000 Array spectrophotometer. Photoluminescence were recorded on a Perkin-Elmer LS 55 spectrofluorometer. High resolution mass spectra (HRMS) were recorded on a GCT premier CAB048 mass spectrometer operating in MALDI-TOF mode. Single crystal X-ray diffraction intensity data were collected at 100 K on a Bruker-Nonices Smart Apex CCD diffractometer with graphite monochromated Mo Kα radiation. Processing of the intensity data was carried out using the SAINT and SADABS routines, and the structure and refinement were conducted using the SHELTL suite of X-ray programs (version 6.10). Ground-state geometries of the silole molecules were optimized using the density functional theory (DFT) with B3LYP hybrid functional at the basis set level of 6-31G*, and the unrestricted formalism (UB3LYP) was adopted for the ion-state geometries. All the theoretical calculations were performed using Gaussian 03 package in a power leader workstation.

Preparation of Nanoaggregates

Stock solutions of all AIE active compounds in THF with a concentration of 20 mM were prepared. Aliquots (1 mL) of the stock solutions were transferred to 10 mL volumetric flasks. After adding appropriate amounts of THF, water was added dropwise under vigorous stirring to furnish 20 μM solutions with defined fractions of water (0-90 vol %). Spectral measurements of the resultant solutions or aggregate suspensions were performed immediately.

General Synthesis of TPE

Synthesis of 1,1,2,2-tetraphenylethene (TPE)

In an ice-cooled suspension of Zn dust (2.48 g, 38.4 mmol) in 50 mL of THF were added TiCl$_4$ (2.14 mL, 19.2 mmol). Into the reflux suspension, benzophenone dissolved in THF (10 mL) was injected (1 g, 5.5 mmol). After refluxing for 2 h, the reaction mixture was cooled to room temperature and filtered. The solvent was evaporated under vacuum and the crude product was purified on a silica gel column using hexane/DCM mixture (10:1 v/v) as eluent. TPE was obtained as a white solid in 83.5% yield. $^1$H NMR (300 MHz, CDCl$_3$), δ (TMS, ppm): 7.07-7.11 (m, 12H), 7.00-7.04 (m, 8H). $^{13}$C NMR (75 MHz, CDCl$_3$), δ (ppm): 144.1, 142.3, 131.7, 127.9, 126.7. HRMS (MALDI-TOF): m/z: 332.1567 (M$^+$, calcd 332.1565). Elemental Analysis: Calcd (%): C, 93.94; H, 6.06. Found (%): C, 93.67; H, 6.12.

Synthesis of 1,1,2,2-tetraphenylethane (s-TPE)

A suspension of 500 mg of TPE in 50 mL of methanol was hydrogenated at atmospheric pressure in the presence of 300 mg of 10% palladium/carbon. Hydrogen was allowed to adsorb for 2 h before reaction termination. The mixture was filtered and the solvent was then evaporated under vacuum. The crude product was purified on a silica gel column using DCM as eluent. s-TPE was isolated as a white solid in 91% yield. $^1$H NMR (300 MHz, CDCl$_3$), δ (TMS, ppm): 7.09-7.20 (m, 12H), 7.00-7.05 (m, 8H), 4.79 (s, 2H). $^{13}$C NMR (75 MHz, CDCl$_3$), δ (ppm): 143.8, 128.9, 128.5, 126.2, 56.7. HRMS (MALDI-TOF): m/z: 334.1721 (M$^+$, calcd 334.1722). Elemental Analysis: Calcd (%): C, 93.37; H, 6.63. Found (%): C, 93.32; H, 6.73.

Shown below is the general procedure to synthesize TPE and its derivative and their hydrogenated products.

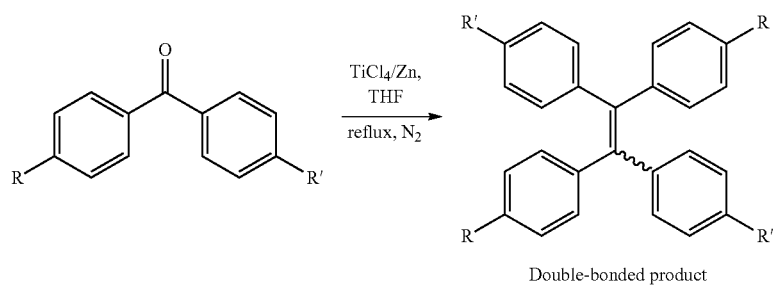

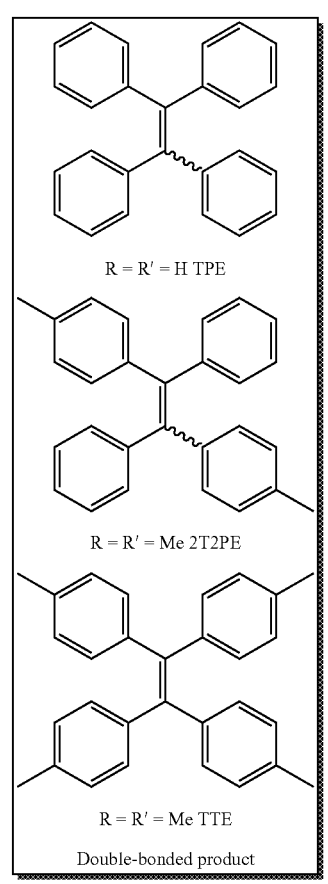

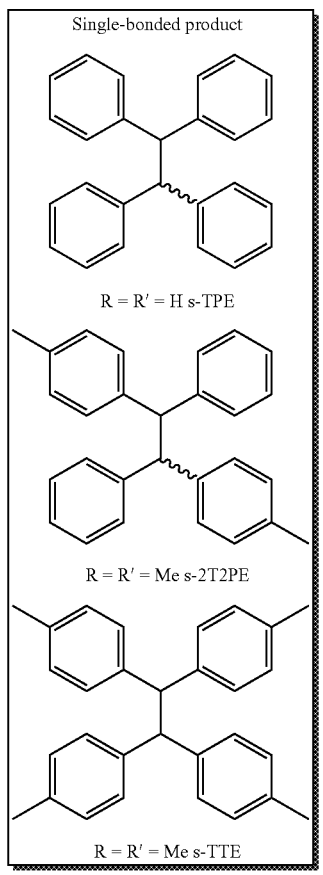

Synthesis of 1,2-diphenyl-1,2-di-p-tolylethene (2T2PE)

Following the general procedure of TPE synthesis with 4-methylbenzophenone (1.08 g, 5.5 mmol), Zn dust (2.48 g, 38.4 mmol) and TiCl$_4$ (2.14 mL, 19.2 mmol) as reactants. 2T2PE was obtained as white solid in 56% yield (555.2 mg).

Synthesis of 1,2-diphenyl-1,2-di-p-tolylethane (s-2T2PE)

It was obtained as a white solid from 500 mg of 2T2PE in 85% yield in the same way as s-TPE. $^{13}$C NMR (75 MHz, CDCl$_3$), δ (ppm): 144.7, 144.6, 141.3, 141.2, 135.8, 129.6, 129.1, 129.0, 128.8, 128.7, 126.4, 56.53, 143.8, 128.9, 128.5, 126.2, 21.7, 21.6.

Synthesis of 1,1,2,2-tetra-p-tolylethene (TTE)

Following the general procedure of TPE synthesis with 4,4'-dimethylbenzophenone (1.48 g, 5.5 mmol), Zn dust (2.48 g, 38.4 mmol) and TiCl$_4$ (2.14 mL, 19.2 mmol) as reactants. TTE was obtained as a white solid in 78% yield (555.2 mg). $^1$H NMR (300 MHz, CDCl$_3$), δ (TMS, ppm): 6.88 (s, 16H), 2.25 (s, 12H). HRMS (MALDI-TOF): m/z: 388.5224 (M$^+$, calcd: 388.5459).

Synthesis of 1,1,2,2-tetra-p-tolylethane (s-TTE)

Following the synthetic procedure for s-TPE, TTE was obtained as white solid in 89% yield. $^1$H NMR (300 MHz, CDCl$_3$), δ (TMS, ppm): 7.03-7.04 (d, 8H), 6.88-6.91 (m, 8H), 4.68 (s, 2H), 2.17 (s, 12H). $^{13}$C NMR (75 MHz, CDCl$_3$), δ (ppm): 141.7, 135.6, 129.5, 128.9, 56.0, 21.6. HRMS (MALDI-TOF): m/z 390.5733 (M$^+$, calcd: 390.5618).

Synthesis of 10,10',11,11'-tetrahydro-5H,5'H-5,5'bidibenzo[a,d][7]annulene (ls-TPE)

The compound was prepared according to the synthetic procedure for TPE using dibenzosuberone (1 g, 0.865 mL, 4.8 mmol), Zn dust (1.342 g, 20.6 mmol) and TiCl$_4$ (1.16 mL, 10.6 mmol). ls-TPE was obtained as a white powder in 23% yield. $^1$H NMR (300 MHz, CDCl$_3$), δ (TMS, ppm): 7.06-6.99 (m, 4H), 6.98-6.95 (m, 4H), 6.72-6.68 (m, 4H), 6.55-6.53 (m, 4H), 4.78 (s, 2H), 3.74-3.80 (m, 4H), 3.01-3.07 (m, 4H). $^{13}$C NMR (75 MHz, CDCl$_3$), δ (ppm): 139.7, 139.6, 132.2, 130.4, 126.7, 125.5, 61.1, 34.3. HRMS (MALDI-TOF): m/z 386.2032 (M calcd: 386.2035).

Crystal Preparation:

Single crystals of s-TPE and ls-TPE were grown at room temperature from their DCM/MeOH mixtures and analyzed on a Bruker-Nonius Smart Apex CCD diffractometer with graphite-monocromated Mo Kα radiation at 100 K. The intensity data were produced under the SAINT and SAD-ABS routines, and the structure solution and refinement were carried out by the SHELXTL suit of X-ray programs (version 6.10). Their crystal data are provided in Tables 1-3 below.

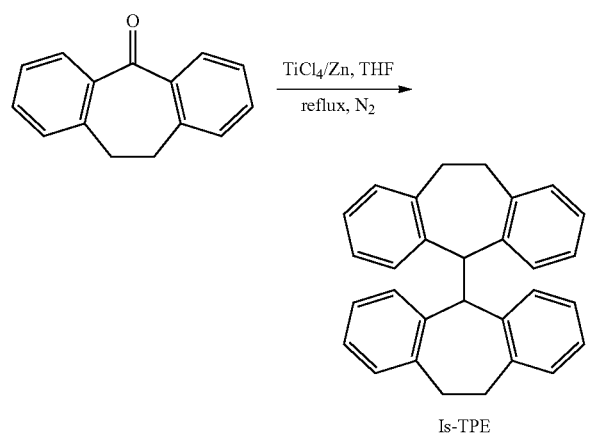

ls-TPE

TABLE 1

Atomic coordinates (x104) and equivalent isotropic displacement parameters

| | x | y | z | U(eq)* |
|---|---|---|---|---|
| C(1) | 5074(2) | 4221(7) | 2153(2) | 27(1) |
| C(1A) | 4859(2) | 2716(7) | 2830(2) | 27(1) |
| C(11) | 5934(1) | 3264(5) | 1928(1) | 58(1) |
| C(12) | 6458(1) | 4951(3) | 2076(1) | 38(1) |
| C(13) | 7200(1) | 4734(3) | 1842(1) | 33(1) |
| C(14) | 7423(1) | 2812(3) | 1463(1) | 37(1) |
| C(15) | 6905(1) | 1104(3) | 1317(1) | 48(1) |
| C(16) | 6165(1) | 1338(4) | 1547(1) | 61(1) |
| C(21) | 4590(1) | 3688(4) | 1463(1) | 54(1) |
| C(22) | 4613(1) | 5635(4) | 1034(1) | 62(1) |
| C(23) | 4170(1) | 5886(3) | 389(1) | 54(1) |
| C(24) | 3689(1) | 4159(4) | 163(1) | 45(1) |
| C(25) | 3661(1) | 2201(3) | 584(1) | 41(1) |
| C(26) | 4108(1) | 1972(3) | 1236(1) | 41(1) |

*U(eq) is defined as one third of the trace of the orthogonalized U$^{ij}$ tensor

TABLE 2

Crystal Data and Structure Refinement for s-TPE

| | |
|---|---|
| Empirical formula | C26H22 |
| Formula weight | 334.44 |
| Temperature | 133(2) K |
| Wavelength | 1.54178 Å |
| Crystal system | Monoclinic |

TABLE 2-continued

Crystal Data and Structure Refinement for s-TPE

| | | |
|---|---|---|
| Space group | C2/c | |
| Unit cell dimensions | a = 17.6477(19) Å | α = 90°. |
| | b = 5.8820(7) Å | β = 91.238(8)°. |
| | c = 17.6454(16) Å | γ = 90°. |
| Volume | 1831.2(3) Å$^3$ | |
| Z | 4 | |
| Density (calculated) | 1.213 Mg/m$^3$ | |
| Absorption coefficient | 0.514 mm$^{-1}$ | |
| F(000) | 712 | |
| Crystal size | 0.28 × 0.12 × 0.08 mm$^3$ | |
| Theta range for data collection | 5.01 to 67.47°. | |
| Index ranges | −21 <= h <= 21, −7 <= k <= 7, −21 <= l <= 21 | |
| Reflections collected | 4812 | |
| Independent reflections | 1594 [R(int) = 0.0495] | |
| Completeness to theta = 66.50° | 97.2% | |
| Absorption correction | Semi-empirical from equivalents | |
| Max. and min. transmission | 1.00 and 0.91 | |
| Refinement method | Full-matrix least-squares on F$^2$ | |
| Data/restraints/parameters | 1594/0/128 | |
| Goodness-of-fit on F$^2$ | 1.015 | |
| Final R indices [I > 2sigma(I)] | R1 = 0.0541, wR2 = 0.1467 | |
| R indices (all data) | R1 = 0.0576, wR2 = 0.1506 | |
| Extinction coefficient | 0.0029(6) | |
| Largest diff. peak and hole | 0.186 and −0.241 e · Å$^{-3}$ | |

TABLE 3

Crystal data and structure refinement for ls-TPE

| | | |
|---|---|---|
| Empirical formula | C30H26 | Temperature |
| Formula weight | 386.51 | Unit cell dimensions |
| | | b = 10.3395(6) Å |
| | | c = 10.4893(7) Å |
| Volume | 1030.68(12) Å$^3$ | |
| Z | 2 | |
| Density (calculated) | 1.245 Mg/m$^3$ | |
| Absorption coefficient | 0.527 mm$^{-1}$ | |
| F(000) | 412 | |
| Crystal size | 0.4 × 0.38 × 0.35 mm$^3$ | ~= 98.128(6)°. |
| Theta range for data collection | 10.36 to 66.99°. | ~= 103.710(6)°. |
| | | ~= 91.394(5)°. |
| Index ranges | −10 <= h <= 11, −10 <= k <= 12, −12 <= l <= 12 | |
| Reflections collected | 6388 | |
| Independent reflections | 3473 [R(int) = 0.0213] | |
| Completeness to theta = 66.50°: | 94.42% | |
| Absorption correction | Semi-empirical from equivalents | |
| Max. and min. transmission | 1.00000 and 0.95200 | |
| Refinement method | Full-matrix least-squares on F$^2$ | |
| Data/restraints/parameters | 3473/0/271 | |
| Goodness-of-fit on F$^2$ | 1.005 | |
| Final R indices [I > 2sigma(I)] | R1 = 0.0336, wR2 = 0.0854 | |
| R indices (all data) | R1 = 0.0360, wR2 = 0.0873 | |
| Largest diff. peak and hole | 0.179 and −0.138 e · Å$^{-3}$ | |

Synthesis and Properties if DBT-Functionalized AIE Materials

THF was distilled from sodium benzophenone ketyl under dry nitrogen immediately prior to use. All other chemicals and regents were purchased from Aldrich (USA) and used as received without further purification. $^1$H and $^{13}$C NMR spectra were measured on a Bruker AV 300 spectrometer in deuterated chloroform using tetramethylsilane (TMS;=0) as the internal reference. Absorption spectra were measured on a Milton Roy Spectronic 3000 Array spectrophotometer. Photoluminescence were recorded on a Perkin-Elmer LS 55 spectrofluorometer. High-resolution mass spectra (HRMS) were recorded on a GCT premier CAB048 mass spectrometer operating in MALDI-TOF mode. Single crystal X-ray diffraction intensity data were collected at 100 K on a Bruker-Nonices Smart Apex CCD diffractometer with graphite monochromated Mo Kα radiation. Processing of the intensity data was carried out using the SAINT and SADABS routines, and the structure and refinement were conducted using the SHELTL suite of X-ray programs (version 6.10). Ground-state geometries of the silole molecules were optimized using the density functional theory (DFT) with B3LYP hybrid functional at the basis set level of 6-31G*, and the unrestricted formalism (UB3LYP) was adopted for the ion-state geometries. All the theoretical calculations were performed using Gaussian 03 package in a power leader workstation.

Preparation of Nanoaggregates

Stock solutions of all AIE active compounds in THF with a concentration of 2 mM were prepared. Aliquots (1 mL) of the stock solutions were transferred to 10 mL volumetric flasks. After adding appropriate amounts of THF, water was added dropwise under vigorous stirring to furnish 20 μM solutions with defined fractions of water (0-90 vol %). Spectral measurements of the resultant solutions or aggregate suspensions were performed immediately.

Transient Electroluminescence:

4,4'-Bis[N-(1-naphthyl)-N-phenylamino]biphenyl (NPB) were purified by a train sublimation method. Organic LEDs were fabricated on a glass substrate coated with ITO (sheet resistance 30 Ω/sq) using a conventional vacuum vapor deposition in a vacuum of $2\times10^{-4}$ Pa. The emitting area of the EL devices was 4 mm$^2$. The organic layers and electrodes were grown by means of conventional vacuum deposition. A quartz crystal oscillator placed near the substrate was used to measure the thickness of the thin films, which were calibrated ex situ using Ambios Technology XP-2 surface profilometer. The absorption spectra of the silole thin films were studied using the quartz substrates. An Agilent 8114A 100V/2 programmable pulse generator was used to apply rectangular voltage pulse to the devices. The repetition rate of the pulse was 1 kHz, and the pulse length was 10 μs. The time-dependent EL signals were detected by the 50-Ω input resistance of a digital oscilloscope (Agilent Model 54815A, 500 MHz/2 Gs/s), together with a Hamamatsu photomultiplier (time resolution: 0.65 ns) located directly on top of the emitting devices.

Synthesis

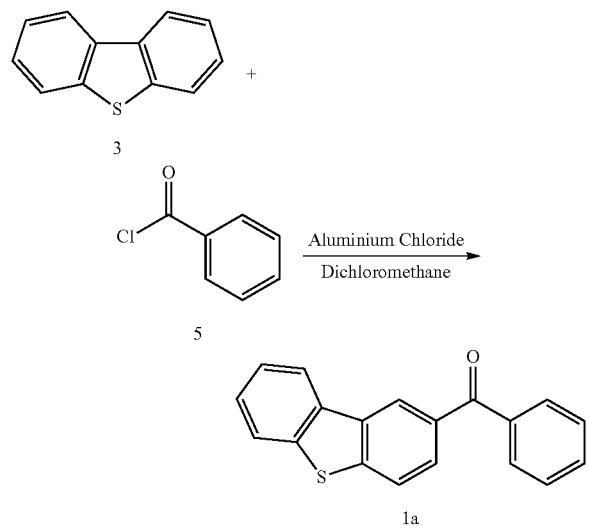

Dibenzo[b,d]thiophen-2-yl(phenyl)methanone (1a)

To a solution of dibenzothiophene (5.0 g, 27 mmol) in 50 mL of dry DCM, benzoyl chloride (3.4 mL, 30 mmol) was added under nitrogen. AlCl$_3$ (5.9 g, 44 mmol) was then added into the reaction mixtures in five separate portions at room temperature. The reaction mixture is refluxed for 3 hours. After cooling to room temperature, the mixture was poured into 100 mL water. Chloroform (50 mL×3) was used to wash the aqueous phase and the combined organic solution was dried with Mg$_2$SO$_4$. The product was purified by column chromatography to give 4.6 g pale white power with 90% yield. R$_f$=0.5 (hexane:chloroform=1:4). $^1$H NMR (300 MHz, CDCl$_3$), δ (TMS, ppm): 8.61 (s, 1H), 8.21-8.19 (m, 1H), 7.97-7.86 (m, 5H), 7.64-7.62 (m, 1H), 7.55-7.49 (m, 4H). MALDI-TOF Found at m/z: 289.0628 (M$^+$, calcd: 289.0642).

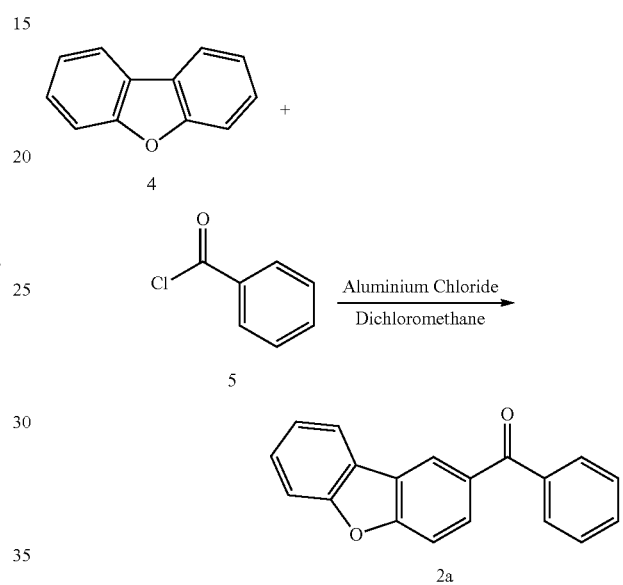

Dibenzo[b,d]furan-2-yl(phenyl)methanone (2a)

To a solution of dibenzofuran (2.0 g 12 mmol) in 50 mL of dry DCM, benzoyl chloride (1.6 mL, 13 mmol) was added under nitrogen. AlCl$_3$ (2.59 g, 19 mmol) was then added into the reaction mixtures in five separate portions at room temperature. The reaction mixture is reluxed for 3 hours. After cooling to room temperature, the mixture was poured into 100 mL water. Chloroform (50 mL×3) was used to wash the aqueous phase and the combined organic solution was dried with Mg$_2$SO$_4$. The product was purified by column chromatography to give 2.4 g pale white power with 75% yield. R$_f$=0.5 (hexane:chloroform=1:4). $^1$H NMR (300 MHz, CDCl$_3$), δ (TMS, ppm): 8.47 (s, 1H), 8.0-7.86 (d, 2H), 7.87-7.84 (d, J=1.5, 2H), 7.66-7.61 (m, 3H), 7.56-7.52 (m, 3H), 7.37-7.40 (m, 1H). MALDI-TOF: m/z: 273.0726 (M$^+$, calcd: 273.0871).

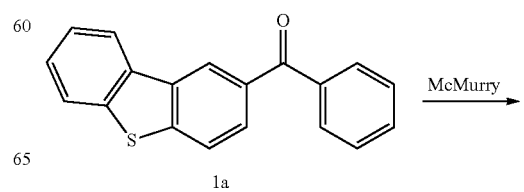

-continued

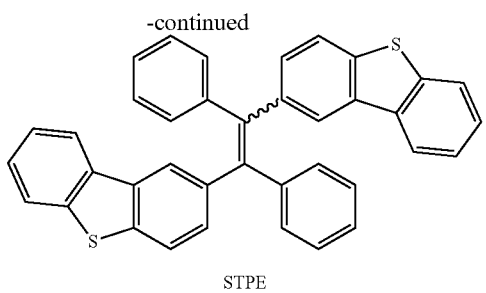

1,2-bis(dibenzo[b,d]thiophen-2-yl)-1,2-diphenylethene (STPE)

Zinc dust (1.15 g, 17.7 mmol) was placed in a two neck flask under nitrogen. 200 mL of THF was added, and then TiCl$_4$ (0.97 mL, 8.83 mmol) was added dropwise in the ice bath. The dark brown suspension was stirred in the ice bath for 10 min and then warmed to room temperature. After 20 min-refluxing, 1a (1.0 g, 3.68 mmol) dissolved in 5 mL THF was added dropwise. The reaction mixture was then refluxed overnight. The reaction was quenched by 50 mL 2M HCl aqueous solution. The product was washed with chloroform (50 mL×3). The combined organic phase was dried over Mg$_2$SO$_4$ and the product was purified by column chromatography to give 0.8 g light yellow powder in 80% yield. R$_f$=0.4 (hexane:chloroform=1:10). $^1$H NMR (300 MHz, CDCl$_3$), δ (TMS, ppm): 7.88-7.75 (d, 2H), 7.60-7.50 (m, 2H), 7.43-7.29 (m, 4H), 7.21-7.08 (m, 16H). $^{13}$C NMR (75 MHz, CDCl$_3$), δ (TMS, ppm): (m, 2H), 7.43-7.29 (m, 4H), 7.21-7.08 (m, 16H). $^{13}$C NMR (75 MHz, CDCl$_3$), δ (TMS, ppm): (m, 2H), 7.43-7.29 (m, 4H), 7.21-7.08 (m, 16H). $^{13}$C NMR (75 MHz, CDCl$_3$), δ (TMS, ppm): 131.96, 130.70, 128.53, 128.42, 128.38, 127.57, 127.21, 127.11, 126.86, 126.02, 124.69, 119.18, 110.91. MALDI-TOF: m/z 544.2123 (M$^+$, calcd 544.1815).

Synthesis of STPE and OTPE

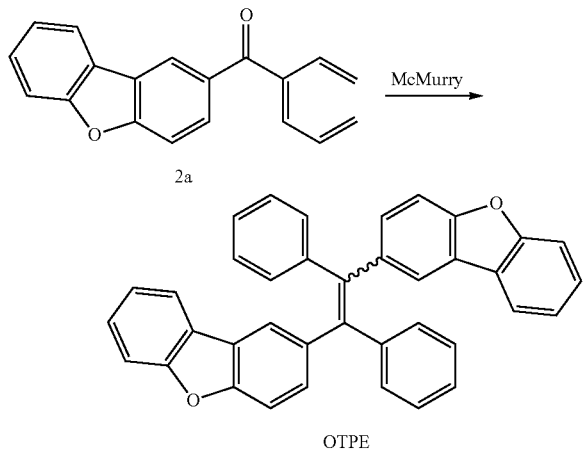

1,2-bis(dibenzo[b,d]furan-2-yl)-1,2-diphenylethene (OTPE)

Zinc dust (0.57 g, 8.8 mmol) was placed in a two neck flask under nitrogen. 200 mL of THF was added, and then TiCl$_4$ (0.49 mL, 4.4 mmol) was added dropwise in the ice bath. The dark brown suspension was stirred in the ice bath for 10 min and then warmed to room temperature. After 20 min-refluxing, 2a (0.5 g, 1.83 mmol) dissolved in 5 mL THF was added dropwise. The reaction mixture was then refluxed overnight. The reaction was quenched by 50 mL 2M HCl aqueous solution. The product was washed with chloroform (50 mL×3). The combined organic phase was dried over Mg$_2$SO$_4$ and the product was purified by column chromatography to give 0.35 g light yellow powder in 74% yield. R$_f$=0.4 (hexane:chloroform=1:10). $^1$H NMR (300 MHz, CDCl$_3$), δ (TMS, ppm): 7.74-7.64 (m, 2H), 7.51-7.37 (m, 4H), 7.29-7.19 (m, 4H), 7.17-7.06 (m, 14H). $_{13}$C NMR (75 MHz, CDCl$_3$), $^{TM}$ (TMS, ppm): 144.68, 144.64, 142.88, 141.77, 141.50, 141.45, 140.23, 138.22, 133.52, 132.51, 132.07, 131.96, 130.70, 128.53, 128.42, 128.38, 127.57, 127.21, 127.11, 126.86, 126.02, 124.69, 119.18, 110.91. MALDI-TOF: m/z 512.1768 (M$_+$, calcd 512.1776).

TABLE 4

| Crystal data and structure refinement for E-STPE | |
|---|---|
| Identification code | E-STPE |
| Empirical formula | C38H24S2 |
| Formula weight | 544.69 |
| Temperature | 173(2) K |
| Wavelength | 1.54178 Å |
| Crystal system | Monoclinic |
| Space group | C2/c |
| Unit cell dimensions | a = 27.593(7) Å  α = 90°. |
|  | b = 9.461(3) Å   β = 117.13(3)°. |
| Volume | c = 24.034(6) Å  γ = 90°. |
|  | 5584(3) Å$^3$ |
| Z | 8 |
| Density (calculated) | 1.296 Mg/m$^3$ |
| Absorption coefficient | 1.916 mm$^{-1}$ |
| F(000) | 2272 |
| Crystal size | 0.12 × 0.08 × 0.02 mm$^3$ |
| Theta range for data collection | 3.60 to 67.45°. |
| Index ranges | −32 <= h <= 32, −11 <= k <= 11, −26 <= l <= 28 |
| Reflections collected | 17204 |
| Independent reflections | 4971 [R(int) = 0.1938] |
| Completeness to theta = 66.50° | 98.8% |
| Absorption correction | Semi-empirical from equivalents |
| Max. and min. transmission | 1.00 and 0.76 |
| Refinement method | Full-matrix least-squares on F$^2$ |
| Data/restraints/parameters | 4971/0/361 |
| Goodness-of-fit on F$^2$ | 1.008 |
| Final R indices [I > 2sigma(I)] | R1 = 0.0512, wR2 = 0.0834 |
| R indices (all data) | R1 = 0.1742, wR2 = 0.1233 |
| Largest diff. peak and hole | 0.212 and −0.220 e · Å$^{-3}$ |

TABLE 5

| Crystal data and structure refinement for Z-STPE | |
|---|---|
| Identification code | Z-STPE |
| Empirical formula | C38H24S2 |
| Formula weight | 544.69 |
| Temperature | 298 K |
| Wavelength | 0.71073 Å |
| Crystal system | Monoclinic |
| Space group | P2(1)/c |
| Unit cell dimensions | a = 10.3620(16) Å; α = 90°. |
|  | b = 11.0761(17) Å; β = 92.463(2)°. |
|  | c = 24.511(4) Å; γ = 90°. |
| Volume | 2810.6(7) Å$^3$ |
| Z | 4 |
| Density (calculated) | 1.287 Mg/m$^3$ |
| Absorption coefficient | 0.216 mm$^{-1}$ |
| F(000) | 1136 |
| Crystal size | 0.2 × 0.15 × 0.14 mm$^3$ |
| Theta range for data collection | 1.66 to 26.99°. |

TABLE 5-continued

Crystal data and structure refinement for Z-STPE

| | |
|---|---|
| Index ranges | −13 <= h <= 8, −14 <= k <= 14, −31 <= l <= 31 |
| Reflections collected | 16064 |
| Independent reflections | 6026 [R(int) = 0.0357] |
| Completeness to theta = 26.99° | 98.1% |
| Absorption correction | Semi-empirical from equivalents |
| Max. and min. transmission | 1 and 0.911974 |
| Refinement method | Full-matrix least-squares on $F^2$ |
| Data/restraints/parameters | 6026/0/361 |
| Goodness-of-fit on $F^2$ | 1.001 |
| Final R indices [I > 2sigma(I)] | R1 = 0.0489, wR2 = 0.1003 |
| R indices (all data) | R1 = 0.0967, wR2 = 0.1110 |
| Largest diff. peak and hole | 0.221 and −0.204 e · Å$^{-3}$ |

Synthesis and Development of AIE Luminescent Materials Containing DBT

THF was distilled from sodium benzophenone ketyl under dry nitrogen immediately prior to use. All other chemicals and regents were purchased from Aldrich (USA) and used as received without further purification. $^1$H and $^{13}$C NMR spectra were measured on a Bruker AV300 spectrometer in deuterated chloroform using tetramethylsilane (TMS; δ=0) as the internal reference. Absorption spectra were measured on a Milton Roy Spectronic 3000 Array spectrophotometer. Photoluminescence were recorded on a Perkin-Elmer LS 55 spectrofluorometer. High resolution mass spectra (HRMS) were recorded on a GCT premier CAB048 mass spectrometer operating in MALDI-TOF mode. Single crystal X-ray diffraction intensity data were collected at 100 K on a Bruker-Nonices Smart Apex CCD diffractometer with graphite monochromated Mo Kα radiation. Processing of the intensity data was carried out using the SAINT and SADABS routines, and the structure and refinement were conducted using the SHELTL suite of X-ray programs (version 6.10). Ground-state geometries of the silole molecules were optimized using the density functional theory (DFT) with B3LYP hybrid functional at the basis set level of 6-31G*, and the unrestricted formalism (UB3LYP) was adopted for the ion-state geometries. All the theoretical calculations were performed using Gaussian 03 package in a power leader workstation.

Preparation of Nanoaggregates:

Stock solutions of all AIE active compounds in THF with a concentration of 2 mM were prepared. Aliquots (1 mL) of the stock solutions were transferred to 10 mL volumetric flasks. After adding appropriate amounts of THF, water was added dropwise under vigorous stirring to furnish 20 μM solutions with defined fractions of water (0-90 vol %). Spectral measurements of the resultant solutions or aggregate suspensions were performed immediately.

Transient Electroluminescence:

NPB were purified by a train sublimation method. Organic LEDs were fabricated on a glass substrate coated with ITO (sheet resistance 30 Ω/sq) using a conventional vacuum vapor deposition in a vacuum of 2×10-4 Pa. The emitting area of the EL devices was 4 mm2. The organic layers and electrodes were grown by means of conventional vacuum deposition. A quartz crystal oscillator placed near the substrate was used to measure the thickness of the thin films, which were calibrated ex situ using Ambios Technology XP-2 surface profilometer. The absorption spectra of the silole thin films were studied using the quartz substrates. An Agilent 8114A 100V/2 programmable pulse generator was used to apply rectangular voltage pulse to the devices. The repetition rate of the pulse was 1 kHz, and the pulse length was 10 μs. The time-dependent EL signals were detected by the 50-Ω input resistance of a digital oscilloscope (Agilent Model 54815A, 500 MHz/2 Gs/s), together with a Hamamatsu photomultiplier (time resolution: 0.65 ns) located directly on top of the emitting devices.

Synthesis of STPE-OX

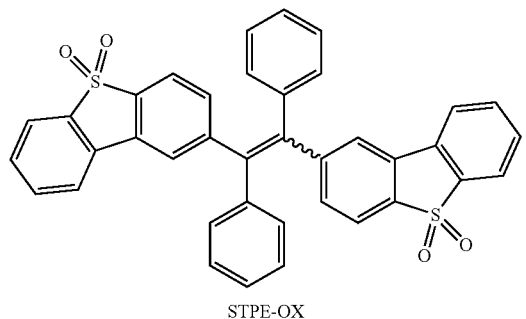 [SMILES: O=S1(=O)c2ccccc2-c2cc(C(=C(c3ccccc3)c3ccc4c(c3)-c3ccccc3S4(=O)=O)c3ccccc3)ccc21]

STPE-OX

Synthesis of 2,2'-(1,2-diphenylethene-1,2-diyl)bis (dibenzo[b,d]thiophene 5,5-dioxide) (STPE-OX)

STPE (1 g) is dissolved in DCM along with excess of m-CPBA (2.0 g), reaction is allowed maintain in the room temperature. TLC indicates with complete reaction of higher polarity products oxidized from STPE. Wash the product with chloroform (50 mL×3) and collect the organic phase, dry with Mg2SO4 and purified by column chromatography to give 0.65 g of light lemon power with a yield of 80% (hexane:DCM=1:2). 1H NMR (300 MHz CDCl3), (TMS, ppm): 7.88-7.75 (d, 2H), 7.60-7.50 (m, 2H), 7.43-7.29 (m, 4H), 7.21-7.08 (m, 16H). 13C NMR (75 MHz, CDCl3), (TMS, ppm): 144.68, 144.64, 142.88, 141.77, 141.50, 141.45, 140.23, 138.22, 133.52, 132.51, 132.07, 131.96, 130.70, 128.53, 128.42, 128.38, 127.57, 127.21, 127.11, 126.86, 126.02, 124.69, 119.18, 110.91. MALDI-TOF: m/z 544.2123 (M+, calcd 544.1815).

General Procedure of "One-Pot" Synthesis of dibenzo[b,d]thiophen-2-yl(4-(diphenylamino)-phenyl)methanone (3, FB-CO-DBT, as shown in flowchart below) Under and inert atmosphere, 4-fluorobenzoic acid (1 g, 7.14 mmol) was charged into a two neck flask equipped with a condenser. Then, 2 mL of SOCl2 were injected, followed by two drops of DMF. The reaction was refluxed for 2 h until the solution became transparent. Excess SOCl2 was vacuumed out of the flask through a NaH-filled tube. The resulting acylchloride was used without further purification. A solution of dibenzothiophene (1.32 g, 7.14 mmol) in 50 mL of dry DCM was injected directly into the carbonyl chloride flask. Following that, AlCl3 (1.05 g, 7.85 mmol) was added into the flask in five separated portions at room temperature. The reaction mixture is allowed to warm back to room temperature and then refluxed for three hours. After cooling down it to room temperature again, the mixture was carefully poured into 100 mL of water. Chloroform (50 mL×3) was used to wash the aqueous phase. The organic layers were collected and dried with Mg2SO4. The final product was purified by column chromatography to give 1.56 g of a bright white power (FB-CO-DBT) with a yield of 73% (Rf=0.55, hexane:chloroform=1:4). Full characterization was not deemed necessary at this stage.

Synthesis scheme and structures of NSTPE

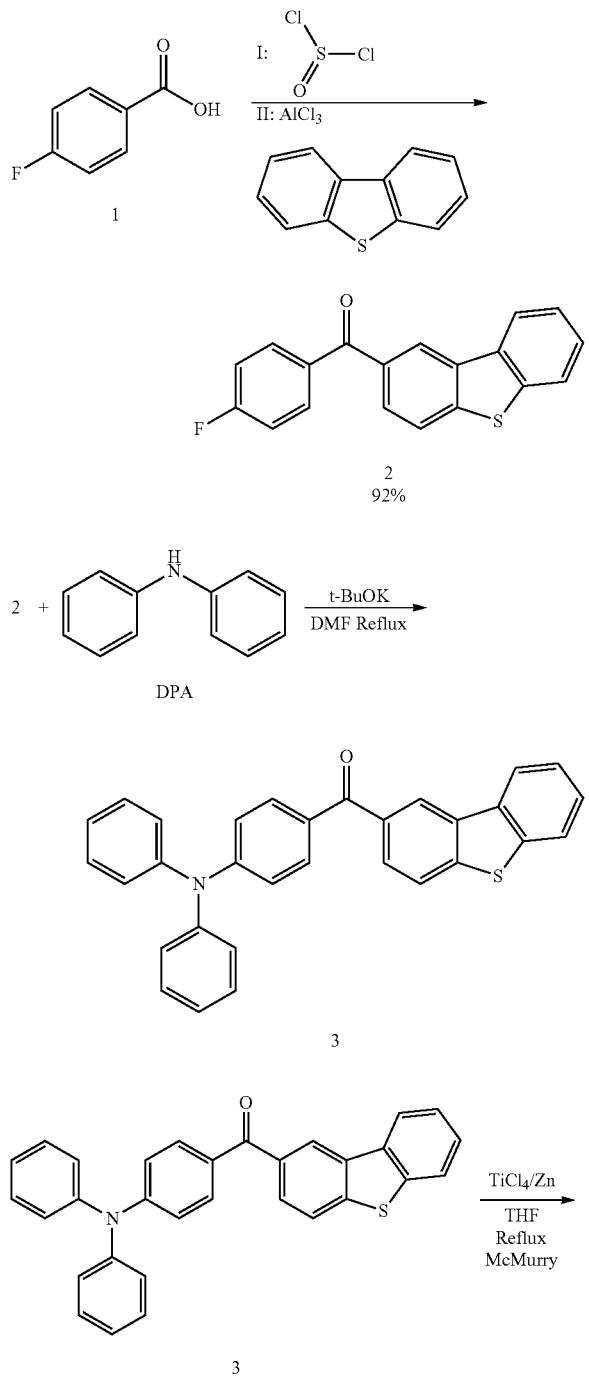

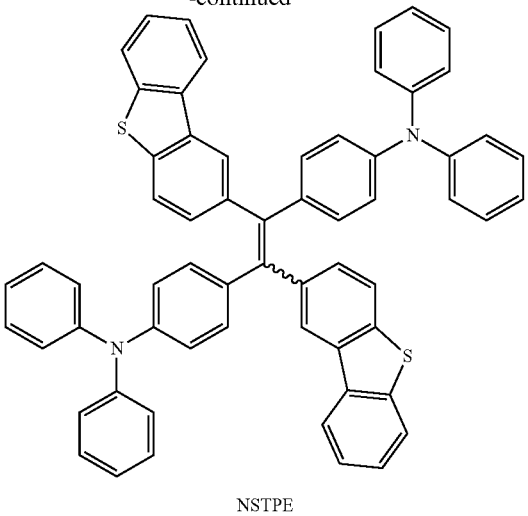

NSTPE

Synthesis of dibenzo[b,d]thiophene-2-yl(4-diphenyl amino)phenyl)methanone (TPA-CO-DBT)

In a two neck flask equipped with a condenser, FB-CO-DBT (1.0 g, 3.3 mmol), diphenylamine (1.11 g, 3.6 mmol) and t-BuOK (0.5 g, 4.3 mmol) were charged. Following that, 50 mL DMF were injected to dissolve the reactants. By doing so, the mixture switches from light to dark brown. The mixture is refluxed 4 hours. After cooling down to room temperature, the mixture was carefully poured into 100 mL of water. Chloroform (50 mL×3) was used to wash the aqueous phase. The organic layers were collected and dried with $Mg_2SO_4$. The final product was purified by column chromatography to give 0.52 g of a bright yellow power (TPA-CO-DBT) with a yield of 40%. $_1$H NMR (300 MHz, CDCl3), δ (TMS, ppm): 8.47 (s, 1H), 8.0-7.86 (d, J=2.1, 2H), 7.87-7.84 (d, J=1.5, 2H), 7.66-7.61 (m, 3H), 7.56-7.52 (m, 3H), 7.37-7.40 (m, 1H). MALDI-TOF: m/z: 455.1389 (M+, calcd: 455.1344). MALDI-TOF: m/z: 455.1389 (M+, calcd: 455.1344).

Synthesis of 4,4'-(1,2-bis(dibenzo[b,d]thiophen-2-yl)ethene-1,2-diyl)-bis(N,N-diphenylaniline) (NSTPE, as Shown Below)

The same procedure as with the OSTPE synthesis was used. Zinc dust (0.37 g, 0.57 mmol), $TiCl_4$ (0.32 mL, 2.90 mmol), TPA-CO-DBT (0.6 g, 0.13 mmol) were used the same way than before. The final product is purified by column chromatography to give 0.24 g of light yellow power with a yield of 41% ($R_f$=0.4, hexane:chloroform=1:10). $^1$H NMR (300 MHz, $CDCl_3$), δ (TMS, ppm): 7.95-7.86 (m, 4H), 7.70-7.67 (m, 2H), 7.47-7.44 (m, 4H), 7.29-7.21 (m, 4H), 7.11-7.09 (m, 4H), 7.05-6.94 (m, 8H), 6.89-6.87 (m, 12H), 6.78-6.76 (m, 4H). 13C NMR (75 MHz, $CDCl_3$), δ (TMS, ppm): 144.68, 144.64, 142.88, 141.77, 141.50, 141.45, 140.23, 138.22, 133.52, 132.51, 132.07, 131.96, 130.70, 128.53, 128.42, 128.38, 127.57, 127.21, 127.11, 126.86, 126.02, 124.69, 119.18, 110.91. MALDI-TOF: m/z 878.2789 (M+, calcd 878.2789).

"One-pot" synthesis scheme leading to NSTPE

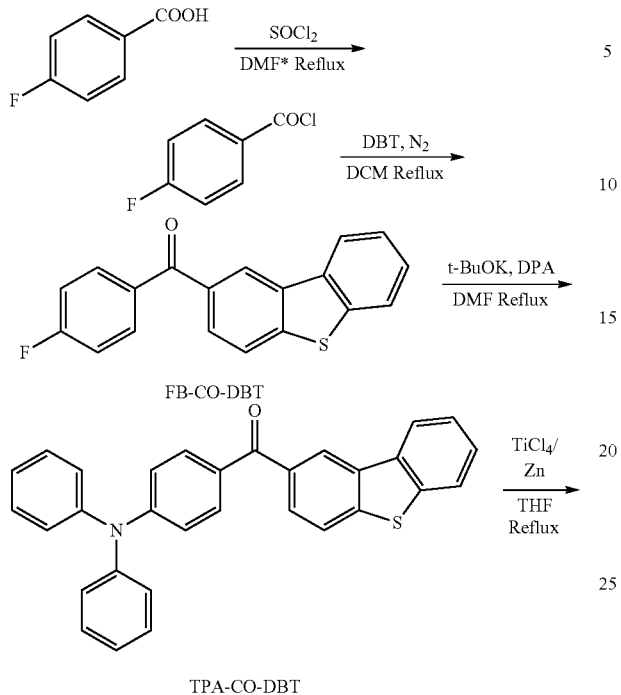

Synthesis of 1,2-bis(dibenzo[b,d]thiophen-2-yl)-1,2-bis(4-methoxyphenyl) ethene (MxSTPE, as Shown Below)

The same procedure as for the NSTPE compound was used. Reactants used: 4-Methoxybenzoic acid (1.5 g); DBT (1.32 g); AlCl₃ (3 g); TiCl4 (2.5 mL); Zn Dust (1 g). Product yield: 75% (0.85 g). ¹H NMR (300 MHz, CDCl₃), δ (TMS, ppm): 7.90-7.69 (m, 6H), 7.61-7.47 (m, 4H), 7.41-7.17 (m, 4H), 7.05-7.00 (m, 4H), 6.71-6.59 (m, 4H), 3.77 (s, 3H), 3.70 (s, 3H). ¹³C NMR (75 MHz, CDCl₃), δ (TMS, ppm): 158.75, 141.59, 141.39, 140.38, 140.29, 133.44, 131.57, 130.88, 129.48, 127.73, 125.71, 125.07, 124.47, 123.07, 122.64, 122.51, 122.28, 118.75, 113.91, 24.41, 23.67. MALDI-TOF: m/z 604.1544 (M+, calcd 604.1530).

Synthesis of MxSTPE

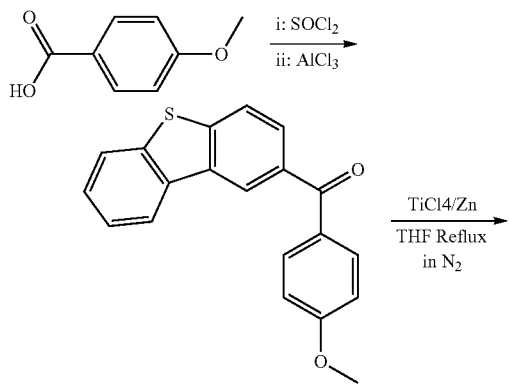

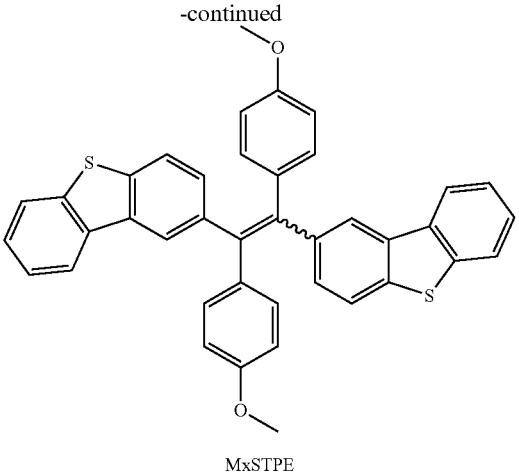

MxSTPE

Synthesis of 1,2-bis(dibenzo[b,d]thiophen-2-yl)-1,2-bis(4-toluyl)ethene (TSTPE)

The same procedure as for the NSTPE compound was used. Reactants used: p-toluic acid (2 g); DBT (1.5 g); AlCl₃ (3.3 g); TiCl₄ (3 mL), Zn Dust (1.5 g). Product yield: 60% (1 g). ¹H NMR (300 MHz, CDCl₃), δ (TMS, ppm): 7.90-7.74 (m, 6H), 7.59-7.48 (m, 2H), 7.40-7.34 (m, 4H), 7.20-7.18 (m, 2H), 7.02-6.99 (m, 4H), 6.96-6.86 (m, 4H), 2.29 (s, 3H), 2.21 (s, 3H). ¹³C NMR (75 MHz, CDCl₃), δ (TMS, ppm): 141.55, 141.41, 141.32, 141.15, 141.10, 140.30, 138.17, 138.10, 136.92, 136.83, 136.16, 135.94, 132.10, 132.02, 131.24, 129.27, 129.21, 127.18, 125.10, 125.05, 124.90, 124.86, 123.43, 123.39, 122.64, 122.602, 122.30, 21.94, 21.85. MALDI-TOF: m/z 572.1758 (M+, calcd 572.1632).

Synthesis of 4, 4'-(1, 2-bis(dibenzoyl[b.d]thiophen-2-yl)ethane-1,2-diyl)-bis(N, N-diphenylaniline) (NSTPE)

The same procedure as with the 202SE synthesis was used. Zinc dust (0.37 g, 0.57 mmol), TiCl₄ (0.32 mL, 2.90 mmol), TPA-CO-DBT (0.6 g, 0.13 mmol) were used the same way than before. The final product is purified by column chromatography to give 0.24 g of light yellow power with a yield of 41% (R_f=0.4, hexane:chloroform=1:10). ¹H NMR (300 MHz, CDCl₃), δ (TMS ppm): 7.88-7.75 (d, 2H), 7.60-7.50 (m, 2H), 7.43-7.29 (m, 4H), 7.21-7.08 (m, 16H). 13C NMR (75 MHz, CDCl₃), δ (TMS, ppm): 144.68, 144.64, 142.88, 141.77, 141.50, 141.45, 140.23, 138.22, 133.52, 132.51, 132.07, 131.96, 130.70, 128.53, 128.42, 128.38, 127.57, 127.21, 127.11, 126.86, 126.02, 124.69, 119.18, 110.91. MALDI-TOF: m/z 625.2455 (M+, calcd).

Synthesis of 2-(1-(4-iodophenyl)-2,2-diphenylvinyl) dibenzo[b,d]thiophene (Compound 4 in Chart A Below)

An addition of n-butyllithium (2.5 M in hexanes, 9.8 mmol) to a solution of diphenylmethane (1.5 g, 8.9 mmol) in THF (100 mL) at 0° C. produced an orange-red solution of diphenylmethyllithium within 30 min. To this highly colored solution was added 2 (3.73 g, 9.0 mmol) at 0° C., and the resulting mixture was allowed to warm to room temperature and was stirred for 6 h. The reaction was quenched with saturated aqueous ammonium chloride solution followed by a standard aqueous workup, affording the corresponding alcohol in nearly quantitative yield. The crude alcohol was dissolved in THF and refluxed in the presence of a catalytic amount of concentrated sulfonic acid with removal of water to afford 2-(1-(4-iodophenyl)-2,2-diphenylvinyl)dibenzo[b,d]thiophene (4) in 83% isolated yield (4.3 g). $R_f$=0.5 (hexane:chloroform=1:4). Full characterization was not deemed necessary at this stage.

Synthesis of bis(4-((4-(1-(dibenzo[b,d]thiophen-2-yl)-2,2-diphenylvinyl)phenyl) ethynyl)phenyl) methanone (Compound 5 in Chart A Below)

Synthesized by minor modified Sonogashira reaction. Reactants are introduced in the triethylamine solution 50 mL in a nitrogen protection one neck 150 mL flask at room temperature with two days: 4 (1.3 g, 2.3 mmol), PdCl$_2$(PPh$_3$)$_2$ (0.11 g, 0.15 mmol), bis(4-ethynylphenyl)methanone (1.06 g, 4.6 mmol), CuI (0.2 g), PPh$_3$ (0.2) g. The crude is dried with silica gel loaded for column chromatography to give 1.02 g of pale yellow power, with a yield of 82%. $R_f$=0.5 (hexane:chloroform=1:4). $^1$H NMR (300 MHz, CDCl$_3$), δ (TMS, ppm): 7.88-7.85 (m, 2H), 7.81-7.75 (m, 8H), 7.60-7.56 (m, 6H), 7.43-7.30 (m, 8H), 7.15-7.07 (m, 26H). $^{13}$C NMR (75 MHz, CDCl$_3$), δ (TMS, ppm): 145.34, 144.09, 144.06, 143.98, 143.93, 142.96, 140.51, 140.43, 140.32, 138.52, 137.19, 136.10, 136.01, 135.27, 132.92, 132.32, 132.03, 131.02, 130.95, 130.66, 129.29, 128.55, 128.43, 127.84, 127.48, 127.34, 126.32, 125.76, 125.13, 125.02, 123.822, 123.465, 123.19, 122.77, 122.42, 122.23, 121.66, 121.33, 121.26, 93.55, 89.67. Full characterization was not deemed necessary at this stage.

Synthesis of 2-(bis(4-((4-(1-(dibenzo[b,d]thiophen-2-yl)-2,2-diphenylvinyl)phenyl) ethynyl)phenyl) methylene)malononitrile (Compound 6 in Chart A Shown Below)

Reaction are taken place in ambient temperature with 1 g of malenitile and 200 mg of 5 in present of pyridine 5 mL and ethanol 50 mL and reflux overnight. The crude is dried with silica gel loaded for column chromatography to give 60 mg of orange power, with a yield of 23.4%. $R_f$=0.5 (hexane:chloroform=1:4). $^1$H NMR (300 MHz, CDCl$_3$), δ (TMS, ppm): 7.90-7.83 (m, 2H), 7.81-7.75 (m, 8H), 7.60-7.56 (m, 6H), 7.43-7.30 (m, 8H), 7.15-7.07 (m, 26H). $^{13}$C NMR (75 MHz, CDCl$_3$), δ (TMS, ppm): 148.30, 147.62, 146.14, 144.56, 144.03, 142.98, 142.96, 140.51, 140.43, 140.32, 138.52, 137.19, 136.10, 136.01, 135.27, 132.92, 132.32, 132.03, 131.02, 130.95, 130.66, 129.29, 128.55, 128.43, 127.84, 127.48, 127.34, 126.32, 125.76, 125.13, 125.02, 123.822, 123.465, 123.19, 122.77, 122.42, 122.23, 121.66, 121.33, 121.26.

Chart A-Synthesis scheme and structures of DiCyan-DBTPE

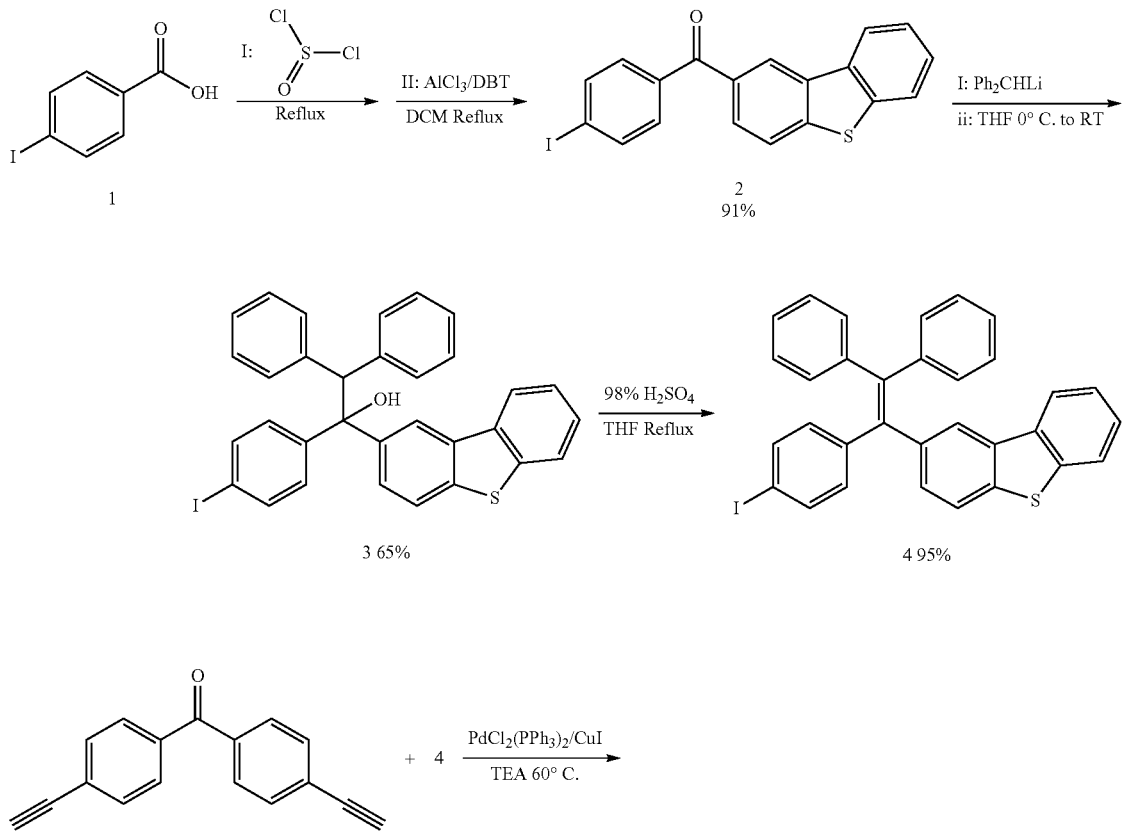

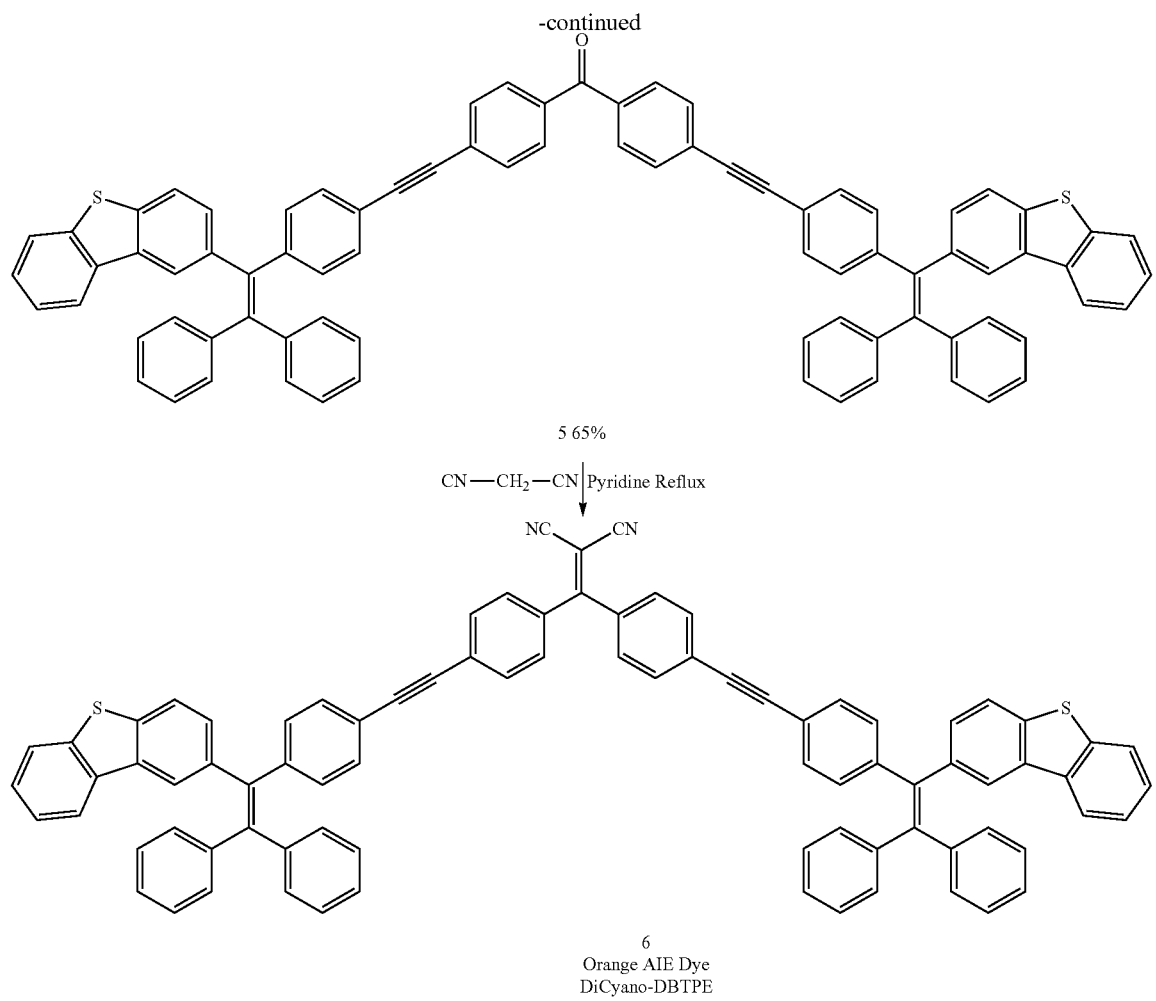

6
Orange AIE Dye
DiCyano-DBTPE

TABLE 6

Crystal data and structure refinement for STPE-OX.

| | |
|---|---|
| Identification code | STPE-OX |
| Empirical formula | C39H28O5S2 |
| Formula weight | 640.7 |
| Temperature | 173(2) |
| Wavelength | 1.54178 |
| Crystal system | Monoclinic |
| Space group | C2/c |
| Unit cell dimensions | a = 11.9007(3) Å  α = 90°. |
| | b = 12.6975(2) Å  β = 93.441(2)°. |
| | c = 20.4717(4) Å  γ = 90°. |
| Volume | 3087.88(11) Å$^3$ |
| Z | 4 |
| Density (calculated) | 1.378 Mg/m3 |
| Absorption coefficient | 1.941 mm$^{-1}$ |
| F(000) | 1336 |
| Crystal size | 0.35 × 0.28 × 0.05 mm$^3$ |
| Theta range for data collection | 5.10 to 67.50°. |
| Index ranges | −11 <= h <= 14, −12 <= k <= 15, −24 <= l <= 23 |
| Reflections collected | 9918 |
| Independent reflections | 2704 [R(int) = 0.0932] |
| Completeness to theta = 66.50° | 96.9% |
| Absorption correction | Semi-empirical from equivalents |
| Max. and min. transmission | 1.00 and 0.61 |
| Refinement method | Full-matrix least-squares on F$^2$ |
| Data/restraints/parameters | 2704/1/208 |
| Goodness-of-fit on F$^2$ | 1.028 |
| Final R indices [I > 2sigma(I)] | R1 = 0.0491, wR2 = 0.1299 |
| R indices (all data) | R1 = 0.0528, wR2 = 0.1336 |
| Largest diff. peak and hole | 0.726 and −0.370 e · Å$^{-3}$ |

TABLE 7

Atomic coordinates (×10$^4$) and equivalent isotropic displacement parameters (Å$^2$ × 10$^3$) for E-STPE. U(eq) is defined as one third of the trace of the orthogonalized U$^{ij}$ tensor.

| | x | y | z | U(eq) |
|---|---|---|---|---|
| S(1) | 2125(1) | 10956(1) | 4190(1) | 32(1) |
| O(1) | 2858(1) | 10773(1) | 4760(1) | 47(1) |
| O(2) | 2505(1) | 11714(1) | 3728(1) | 43(1) |
| C(1) | 698(1) | 6094(1) | 3098(1) | 29(1) |
| C(2) | 1380(2) | 5381(1) | 2796(1) | 35(1) |
| C(3) | 1651(2) | 4423(2) | 3092(1) | 43(1) |
| C(4) | 1251(2) | 4176(1) | 3693(1) | 42(1) |
| C(5) | 579(2) | 4891(1) | 4001(1) | 40(1) |
| C(6) | 309(2) | 5845(1) | 3712(1) | 34(1) |
| C(10) | 332(2) | 7109(1) | 2778(1) | 31(1) |
| C(11) | 778(2) | 8070(1) | 3130(1) | 30(1) |
| C(12) | 73(2) | 8817(1) | 3394(1) | 33(1) |
| C(13) | 555(2) | 9675(1) | 3738(1) | 32(1) |
| C(14) | 1719(2) | 9769(1) | 3783(1) | 31(1) |
| C(15) | 2437(2) | 9036(1) | 3544(1) | 35(1) |
| C(16) | 1949(2) | 8167(1) | 3227(1) | 36(1) |

TABLE 7-continued

Atomic coordinates (×10⁴) and equivalent isotropic displacement parameters ($Å^2 \times 10^3$) for E-STPE. U(eq) is defined as one third of the trace of the orthogonalized $U^{ij}$ tensor.

|       | x       | y        | z       | U(eq)  |
|-------|---------|----------|---------|--------|
| C(17) | −14(2)  | 10508(1) | 4098(1) | 35(1)  |
| C(18) | 739(2)  | 11238(1) | 4389(1) | 34(1)  |
| C(19) | 411(2)  | 12063(2) | 4771(1) | 43(1)  |
| C(20) | −732(2) | 12159(2) | 4862(1) | 55(1)  |
| C(21) | −1491(2)| 11444(2) | 4582(1) | 59(1)  |
| C(22) | −1152(2)| 10614(2) | 4194(1) | 49(1)  |
| O(1S) | 1052(4) | 1633(4)  | 2475(3) | 93(1)  |
| C(1S) | 75(12)  | 1942(4)  | 2458(8) | 78(2)  |

TABLE 8

Bond lengths [Å] and angles [°] for E-STPE.

| | | | |
|---|---|---|---|
| S(1)—O(1) | 1.4325(15) | S(1)—O(2) | 1.4412(14) |
| S(1)—C(18) | 1.7597(19) | S(1)—C(14) | 1.7746(16) |
| C(1)—C(2) | 1.387(2) | C(1)—C(6) | 1.402(2) |
| C(1)—C(10) | 1.498(2) | C(2)—C(3) | 1.388(3) |
| C(3)—C(4) | 1.382(3) | C(4)—C(5) | 1.387(3) |
| C(5)—C(6) | 1.378(3) | C(10)—C(10)#1 | 1.345(3) |
| C(10)—C(11) | 1.498(2) | C(11)—C(12) | 1.397(2) |
| C(11)—C(16) | 1.402(3) | C(12)—C(13) | 1.400(2) |
| C(13)—C(14) | 1.389(2) | C(13)—C(17) | 1.478(2) |
| C(14)—C(15) | 1.373(2) | C(15)—C(16) | 1.390(3) |
| C(17)—C(22) | 1.386(3) | C(17)—C(18) | 1.397(3) |
| C(18)—C(19) | 1.377(3) | C(19)—C(20) | 1.389(3) |
| C(20)—C(21) | 1.382(3) | C(21)—C(22) | 1.394(3) |
| O(1S)—C(1S) | 1.225(14) | | |
| O(1)—S(1)—O(2) | 116.27(9) | O(1)—S(1)—C(18) | 112.19(9) |
| O(2)—S(1)—C(18) | 110.57(8) | O(1)—S(1)—C(14) | 112.35(8) |
| O(2)—S(1)—C(14) | 110.27(8) | C(18)—S(1)—C(14) | 92.80(8) |
| C(2)—C(1)—C(6) | 119.12(15) | C(2)—C(1)—C(10) | 121.90(15) |
| C(6)—C(1)—C(10) | 118.95(15) | C(1)—C(2)—C(3) | 120.27(16) |
| C(4)—C(3)—C(2) | 120.34(17) | C(3)—C(4)—C(5) | 119.65(17) |
| C(6)—C(5)—C(4) | 120.45(17) | C(5)—C(6)—C(1) | 120.17(17) |
| C(10)#1-C(10)—C(11) | 125.44(9) | C(10)#1-C(10)—C(1) | 120.71(9) |
| C(11)—C(10)—C(1) | 113.85(14) | C(12)—C(11)—C(16) | 120.07(14) |
| C(12)—C(11)—C(10) | 122.42(15) | C(16)—C(11)—C(10) | 117.39(15) |
| C(11)—C(12)—C(13) | 119.04(16) | C(14)—C(13)—C(12) | 118.55(15) |
| C(14)—C(13)—C(17) | 112.93(14) | C(12)—C(13)—C(17) | 128.46(16) |
| C(15)—C(14)—C(13) | 123.84(15) | C(15)—C(14)—S(1) | 125.83(14) |
| C(13)—C(14)—S(1) | 110.33(12) | C(14)—C(15)—C(16) | 116.98(17) |
| C(15)—C(16)—C(11) | 121.32(16) | C(22)—C(17)—C(18) | 118.86(16) |
| C(22)—C(17)—C(13) | 128.37(16) | C(18)—C(17)—C(13) | 112.72(16) |
| C(19)—C(18)—C(17) | 123.32(17) | C(19)—C(18)—S(1) | 126.01(14) |
| C(17)—C(18)—S(1) | 110.67(13) | C(18)—C(19)—C(20) | 117.18(18) |
| C(21)—C(20)—C(19) | 120.49(18) | C(20)—C(21)—C(22) | 121.92(19) |
| C(17)—C(22)—C(21) | 118.23(18) | | |

TABLE 9

Anisotropic displacement parameters ($Å^2 \times 10^3$) for E-STPE. The anisotropic displacement factor exponent takes the form: $-2\pi^2 [h^2 a^{*2} U^{11} + \ldots + 2 h k a^* b^* U^{12}]$

|       | $U^{11}$ | $U^{22}$ | $U^{33}$ | $U^{23}$ | $U^{13}$ | $U^{12}$ |
|-------|------|------|------|------|------|------|
| S(1)  | 34(1) | 24(1) | 37(1) | −5(1) | −4(1) | −4(1) |
| O(1)  | 45(1) | 48(1) | 47(1) | −7(1) | −15(1) | −5(1) |
| O(2)  | 48(1) | 27(1) | 54(1) | 0(1) | 6(1) | −5(1) |
| C(1)  | 36(1) | 22(1) | 27(1) | −1(1) | −5(1) | −3(1) |
| C(2)  | 46(1) | 30(1) | 29(1) | −2(1) | −1(1) | 5(1) |
| C(3)  | 51(1) | 31(1) | 45(1) | −6(1) | −6(1) | 11(1) |
| C(4)  | 56(1) | 24(1) | 45(1) | 6(1) | −12(1) | 2(1) |
| C(5)  | 49(1) | 39(1) | 32(1) | 7(1) | −3(1) | −3(1) |
| C(6)  | 40(1) | 30(1) | 31(1) | −2(1) | 0(1) | 1(1) |
| C(10) | 42(1) | 20(1) | 30(1) | −2(1) | −1(1) | 0(1) |
| C(11) | 42(1) | 19(1) | 29(1) | 2(1) | −4(1) | −2(1) |
| C(12) | 35(1) | 26(1) | 36(1) | −4(1) | −5(1) | −2(1) |
| C(13) | 37(1) | 25(1) | 32(1) | −3(1) | −5(1) | −1(1) |
| C(14) | 38(1) | 21(1) | 33(1) | −2(1) | −3(1) | −4(1) |
| C(15) | 35(1) | 28(1) | 41(1) | 0(1) | −1(1) | 0(1) |
| C(16) | 42(1) | 24(1) | 40(1) | −1(1) | 2(1) | 2(1) |
| C(17) | 37(1) | 29(1) | 39(1) | −6(1) | −1(1) | −1(1) |
| C(18) | 38(1) | 28(1) | 36(1) | −5(1) | 0(1) | −3(1) |
| C(19) | 51(1) | 34(1) | 45(1) | −15(1) | 1(1) | −5(1) |
| C(20) | 52(1) | 48(1) | 65(1) | −28(1) | 8(1) | 4(1) |
| C(21) | 42(1) | 59(1) | 76(2) | −30(1) | 9(1) | 2(1) |
| C(22) | 37(1) | 46(1) | 64(1) | −25(1) | −1(1) | −4(1) |

TABLE 10

Hydrogen coordinates (×10⁴) and isotropic displacement parameters ($Å^2 \times 10^3$) for E-STPE.

|       | x    | y    | z    | U(eq) |
|-------|------|------|------|-------|
| H(2A) | 1662 | 5548 | 2384 | 42    |
| H(3A) | 2114 | 3936 | 2881 | 51    |

TABLE 10-continued

Hydrogen coordinates (×10⁴) and isotropic displacement parameters ($Å^2 \times 10^3$) for E-STPE.

|       | x     | y     | z    | U(eq) |
|-------|-------|-------|------|-------|
| H(4A) | 1435  | 3519  | 3894 | 51    |
| H(5A) | 304   | 4722  | 4415 | 48    |
| H(6A) | −143  | 6335  | 3929 | 40    |
| H(12A)| −722  | 8744  | 3341 | 39    |
| H(15A)| 3231  | 9119  | 3593 | 42    |
| H(16A)| 2419  | 7627  | 3073 | 43    |
| H(19A)| 943   | 12546 | 4963 | 52    |
| H(20A)| −993  | 12722 | 5119 | 66    |
| H(21A)| −2268 | 11519 | 4656 | 70    |
| H(22A)| −1685 | 10133 | 4001 | 59    |
| H(1S) | 1367  | 1699  | 2856 | 112   |
| H(1S1)| −20   | 2428  | 2823 | 118   |
| H(1S2)| −430  | 1339  | 2496 | 118   |
| H(1S3)| −105  | 2307  | 2043 | 118   |

TABLE 11

Torsion angles [°] for STPE-OX.

| | |
|---|---|
| C(6)—C(1)—C(2)—C(3) | 1.4(3) |
| C(10)—C(1)—C(2)—C(3) | −176.48(17) |
| C(1)—C(2)—C(3)—C(4) | −0.5(3) |
| C(2)—C(3)—C(4)—C(5) | −0.3(3) |
| C(3)—C(4)—C(5)—C(6) | 0.0(3) |
| C(4)—C(5)—C(6)—C(1) | 0.9(3) |
| C(2)—C(1)—C(6)—C(5) | −1.6(3) |
| C(10)—C(1)—C(6)—C(5) | 176.30(17) |
| C(2)—C(1)—C(10)—C(10)#1 | 64.2(3) |
| C(6)—C(1)—C(10)—C(10)#1 | −113.6(2) |
| C(2)—C(1)—C(10)—C(11) | −115.45(18) |
| C(6)—C(1)—C(10)—C(11) | 66.7(2) |
| C(10)#1-C(10)—C(11)—C(12) | 62.3(3) |
| C(1)—C(10)—C(11)—C(12) | −118.04(18) |
| C(10)#1-C(10)—C(11)—C(16) | −121.9(2) |
| C(1)—C(10)—C(11)—C(16) | 57.8(2) |
| C(16)—C(11)—C(12)—C(13) | 1.9(2) |
| C(10)—C(11)—C(12)—C(13) | 177.64(15) |
| C(11)—C(12)—C(13)—C(14) | 2.2(2) |
| C(11)—C(12)—C(13)—C(17) | −174.89(16) |
| C(12)—C(13)—C(14)—C(15) | −4.0(3) |
| C(17)—C(13)—C(14)—C(15) | 173.49(16) |
| C(12)—C(13)—C(14)—S(1) | 176.05(13) |
| C(17)—C(13)—C(14)—S(1) | −6.43(18) |
| O(1)—S(1)—C(14)—C(15) | −57.51(18) |
| O(2)—S(1)—C(14)—C(15) | 73.95(17) |
| C(18)—S(1)—C(14)—C(15) | −172.91(16) |
| O(1)—S(1)—C(14)—C(13) | 122.42(13) |
| O(2)—S(1)—C(14)—C(13) | −106.12(13) |
| C(18)—S(1)—C(14)—C(13) | 7.02(13) |
| C(13)—C(14)—C(15)—C(16) | 1.5(3) |
| S(1)—C(14)—C(15)—C(16) | −178.61(13) |
| C(14)—C(15)—C(16)—C(11) | 2.9(3) |
| C(12)—C(11)—C(16)—C(15) | −4.6(3) |
| C(10)—C(11)—C(16)—C(15) | 179.48(15) |
| C(14)—C(13)—C(17)—C(22) | −175.2(2) |
| C(12)—C(13)—C(17)—C(22) | 2.1(3) |
| C(14)—C(13)—C(17)—C(18) | 2.2(2) |
| C(12)—C(13)—C(17)—C(18) | 179.44(17) |
| C(22)—C(17)—C(18)—C(19) | 0.1(3) |
| C(13)—C(17)—C(18)—C(19) | −177.53(18) |
| C(22)—C(17)—C(18)—S(1) | −179.22(16) |
| C(13)—C(17)—C(18)—S(1) | 3.12(19) |
| O(1)—S(1)—C(18)—C(19) | 59.4(2) |
| O(2)—S(1)—C(18)—C(19) | −72.20(19) |
| C(14)—S(1)—C(18)—C(19) | 174.92(18) |
| O(1)—S(1)—C(18)—C(17) | −121.30(14) |
| O(2)—S(1)—C(18)—C(17) | 107.12(14) |
| C(14)—S(1)—C(18)—C(17) | −5.76(14) |
| C(17)—C(18)—C(19)—C(20) | −0.2(3) |
| S(1)—C(18)—C(19)—C(20) | 179.04(17) |
| C(18)—C(19)—C(20)—C(21) | 0.5(4) |
| C(19)—C(20)—C(21)—C(22) | −0.8(4) |

TABLE 11-continued

Torsion angles [°] for STPE-OX.

| | |
|---|---|
| C(18)—C(17)—C(22)—C(21) | −0.4(3) |
| C(13)—C(17)—C(22)—C(21) | 176.9(2) |
| C(20)—C(21)—C(22)—C(17) | 0.7(4) |

Symmetry transformations used to generate equivalent atoms: #1 −x, y, −z + ½

Composition and Synthesis of Aggregation-Induced Emission Materials for Triboluminescence and Chemiluminescence THF was distilled from sodium benzophenone ketyl under dry nitrogen immediately prior to use. All other chemicals and regents were purchased from Aldrich (USA) and used as received without further purification. Hydrogen peroxide (30% by weight) was purchased from Honeywell without purification. $^1$H and $^{13}$C NMR spectra were measured on a Bruker AV 300 spectrometer in deuterated chloroform using tetramethylsilane (TMS; δ=0) as the internal reference. Absorption spectra were measured on a Milton Roy Spectronic 3000 Array spectrophotometer. Photoluminescence (PL) were recorded on a Perkin-Elmer LS 55 spectrofluorometer. High resolution mass spectra (HRMS) were recorded on a GCT premier CAB048 mass spectrometer operating in MALDI-TOF mode. Single crystal X-ray diffraction intensity data were collected at 100 K on a Bruker-Nonices Smart Apex CCD diffractometer with graphite monochromated Mo Kα radiation. Processing of the intensity data was carried out using the SAINT and SADABS routines, and the structure and refinement were conducted using the SHELTL suite of X-ray programs (version 6.10). Ground-state geometries of the molecules were optimized using the density functional theory (DFT) with B3LYP hybrid functional at the basis set level of 6-31G*, and the unrestricted formalism (UB3LYP) was adopted for the ion-state geometries. All the theoretical calculations were performed using Gaussian 03 package in a power leader workstation Synthesis of [CuPy(PPh$_3$)$_2$]I (LX-1) and ([CuPy(PPh3)]I)$_2$) (LX-2)

A pyridine solution (25 mL) containing CuI (0.95 g, 5 mmol) and PPh$_3$ (1.31 g, 5 mmol) was stirred at 70° C. for 3 hours, after which the mixture was cooled slowly for four dats. Yellow crystal were grown at the bottom. Followed by filtration and washing, the crystal with toluene (5 mL×3), the copper (I) compounds were separated by their emission colors.

TABLE 12

Crystal Data and Structure for LX-1

| | | |
|---|---|---|
| Identification code | LX-1 | |
| Empirical formula | C46H40Cu2I2N2P2 | |
| Formula weight | 1063.62 | |
| Temperature | 298.15 K | |
| Wavelength | 0.71073 Å | |
| Crystal system | Monoclinic | |
| Space group | C2/c | |
| Unit cell dimension | a = 26.092(4) Å | α = 90°. |
| | b = 14.495(2) Å | β = 95.226(2)°. |
| | c = 11.3510(18) Å | γ = 90°. |
| Volume | 4275.2(11) Å$^3$ | |
| Z | 4 | |
| Density (calculated) | 1.652 Mg/m$^3$ | |
| Absorption coefficient | 2.548 mm$^{-1}$ | |
| F(000) | 2096 | |

TABLE 12-continued

Crystal Data and Structure for LX-1

| | |
|---|---|
| Crystal size | 0.2 × 0.18 × 0.18 mm$^3$ |
| Theta range for data collection | 1.57 to 26.00°. |
| Index ranges | −32 <= h <= 31, |
| | −17 <= k <= 16, |
| | −13 <= l <= 13 |
| Reflections collected | 11682 |
| Independent reflections | 4178 [R(int) = 0.0267] |
| Completeness to theta = 25.00° | 99.4% |
| Absorption correction | Semi-empirical from equivalents |
| Max. and min. transmission | 1 and 0.889485 |
| Refinement method | Full-matrix least-squares on F$^2$ |
| Data/restraints/parameters | 4178/0/245 |
| Goodness-of-fit on F$^2$ | 1.006 |
| Final R indices [I > 2sigma(I)] | R1 = 0.0382, wR2 = 0.0819 |
| R indices (all data) | R1 = 0.0553, wR2 = 0.0876 |
| Largest diff. peak and hole | 0.795 and −0.264 e · Å$^{-3}$ |

TABLE 13

Crystal data and structure refinement for LX-2

| | |
|---|---|
| Identification code | LX-2 |
| Empirical formula | C41H35CuINP2 |
| Formula weight | 794.08 |
| Temperature | 173.00(14) K |
| Wavelength | 1.5418 Å |
| Crystal system | Triclinic |
| Space group | P-1 |
| Unit cell dimensions | a = 9.8491(4) Å   α = 81.735(5)°. |
| | b = 10.4720(7) Å   β = 85.608(4)°. |
| | c = 19.4841(11) Å   γ = 63.581(5)°. |
| Volume | 1780.84(17) Å$^3$ |
| Z | 2 |
| Density (calculated) | 1.481 Mg/m$^3$ |
| Absorption coefficient | 8.739 mm$^{-1}$ |
| F(000) | 800 |
| Crystal size | 0.25 × 0.2 × 0.2 mm$^3$ |
| Theta range for data collection | 4.59 to 66.99°. |
| Index ranges | −11 <= h <= 6, |
| | −12 <= k <= 12, |
| | −23 <= l <= 23 |
| Reflections collected | 10305 |
| Independent reflections | 6142 [R(int) = 0.0754] |
| Completeness to theta = 66.50° | 96.8% |
| Absorption correction | Semi-empirical from equivalents |
| Max. and min. transmission | 1.00000 and 0.63076 |
| Refinement method | Full-matrix least-squares on F$^2$ |
| Data/restraints/parameters | 6142/0/415 |
| Goodness-of-fit on F$^2$ | 1.001 |
| Final R indices [I > 2sigma(I)] | R1 = 0.0572, wR2 = 0.1417 |
| R indices (all data) | R1 = 0.0658, wR2 = 0.1482 |
| Largest diff. peak and hole | 1.169 and −0.937 e · Å$^{-3}$ |

Synthesis of Compounds Exhibiting Chemiluminescence in Solid State

A piece of cotton soaked with AIE material is placed on the top of a beaker, where reaction of oxalyl chloride and hydrogen peroxide takes please. The capture of DD (1,2-dioxetane-3,4-dione), (represented by the formula

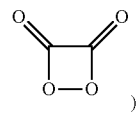

by the AIE dye then triggers the latter to emit intensely in the absence of any UV irradiation. For better observation, dibenzothiophene-functionalized ethane (NSTPE) is used as the dye molecule because it emits greenish-yellow light (528 nm), in which human eye is very sensitive to this specific wavelength. Since cotton possesses numerous porous, it is regarded as the best choice for capturing DD. AS NSTPE is AIE-active, the AIE cotton is made by dipping the cotton (50 mg in weight) to the dichloromethane solution of NSTPE (5 G L-1) followed by solvent evaporation in fume hood at room temperature. After stretching the cotton to a size similar to the diameter of the beaker, the experiment is ready to demonstrate.

After dropping oxalyl chloride into the hydrogen peroxide solution, DD is instantly generated and evaporates to the mouth of the beaker. As the cotton has random shape, emission was observed constantly from different parts where DD strokes.

The stained cotton, its four-membered ring composes generating and anion carbon dioxide and one neutral carbon dioxide. A cation of NSTPE is also formed under such reaction. Recombination of the charges pumps the dye to the excited state. Since the RIR mechanism has forbidden relaxation of excited state, strong emission is therefore observed in NSTPE.

The solid-state chemiluminescence of NSTPE and STPE can also be demonstrated by their casted films on glass slices. Hydrogen peroxide is first injected on the surface of dye-deposited slices followed by addition of oxalyl chloride to the H2O2 droplets. It is seen that the center part becomes dark because the generation of DD has forced the hydrogen peroxide to move out. The generated DD encounters the luminogenic molecules, which induces them to emit. The light emission extinguishes quickly before another drop of oxalyl chloride is added.

With the information contained herein, various departures from precise descriptions of the present subject matter will be readily apparent to those skilled in the art to which the present subject matter pertains, without departing from the spirit and the scope of the below claims. The present subject matter is not considered limited in scope to the procedures, properties, or components defined, since the preferred embodiments and other descriptions are intended only to be illustrative of particular aspects of the presently provided subject matter. Indeed, various modifications of the described modes for carrying out the present subject matter which are obvious to those skilled in chemistry, biochemistry, or related fields are intended to be within the scope of the following claims.

We claim:

1. A TPE derivative composition having a luminogen exhibiting aggregation induced emission comprising:
   at least one luminogen having a backbone structure selected from a group consisting of

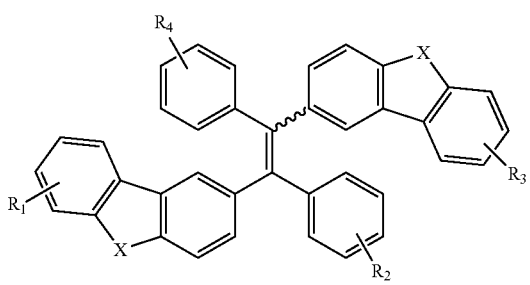

wherein $R_1$, $R_2$, $R_3$, and $R_4$ each can be independently selected from the group consisting of hydrogen, alkyl, unsaturated alkyl, heteroalkyl, cycloalkyl, heterocycloalkyl, aryl, and heteroaryl; and wherein each X is independently selected from the group consisting of O, S, Se, Te, C, Si, Ge, P, As, and Sb, wherein the luminogen is STPE when X is sulphur, STPE having the formula

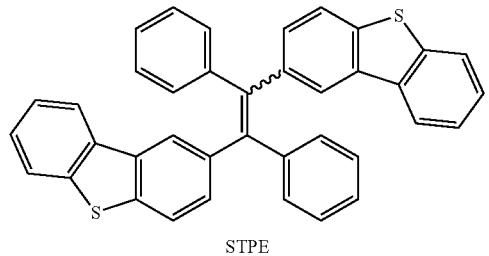

STPE

2. A TPE derivative composition having a luminogen exhibiting aggregation induced emission comprising:
at least one luminogen having a backbone structure selected from a group consisting of

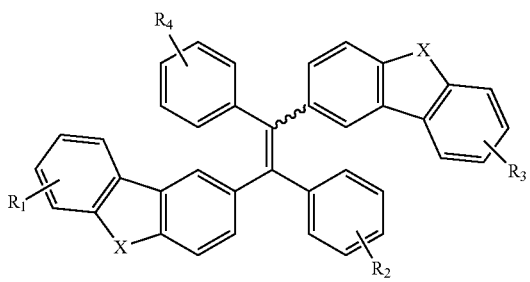

wherein $R_1$, $R_2$, $R_3$, and $R_4$ each can be independently selected from the group consisting of hydrogen, alkyl, unsaturated alkyl, heteroalkyl, cycloalkyl, heterocycloalkyl, aryl, and heteroaryl; and wherein each X is independently selected from the group consisting of O, S, Se, Te, C, Si, Ge, P, As, and Sb, wherein the luminogen is OTPE when X is oxygen, OTPE having the formula

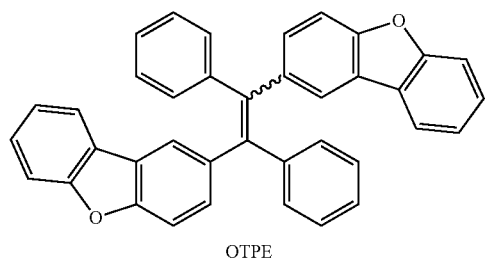

OTPE

3. The composition of claim 1, wherein the luminogen is insoluble in water.

4. The composition of claim 1, wherein the luminogen is soluble in organic solvents.

5. The composition of claim 1, wherein the luminogen is soluble in DCM, chloroform and THF.

6. The composition of claim 1, wherein the luminogen is resistant to high voltage.

7. The composition of claim 1, wherein STPE emits red light or green light mixed with blue emissions.

8. The composition of claim 1, wherein the luminogen emits light in solid state.

9. The composition of claim 1, wherein each X can further include a hydrogen, alkyl, heteroalkyl, cycloalkyl, heterocycloalkyl, aryl, heteroaryl, or a combination thereof.

10. The composition of claim 1, wherein the luminogen is used in electroluminescent devices.

11. The composition of claim 2, wherein the luminogen is insoluble in water.

12. The composition of claim 2, wherein the luminogen is soluble in organic solvents.

13. The composition of claim 2, wherein the luminogen is soluble in DCM, chloroform and THF.

14. The composition of claim 2, wherein the luminogen is resistant to high voltage.

15. The composition of claim 2, wherein STPE emits red light or green light mixed with blue emissions.

16. The composition of claim 2, wherein the luminogen emits light in solid state.

17. The composition of claim 2, wherein each X can further include a hydrogen, alkyl, heteroalkyl, cycloalkyl, heterocycloalkyl, aryl, heteroaryl, or a combination thereof.

18. The composition of claim 2, wherein the luminogen is used in electroluminescent devices.

* * * * *

UNITED STATES PATENT AND TRADEMARK OFFICE
CERTIFICATE OF CORRECTION

PATENT NO. : 9,929,363 B2
APPLICATION NO. : 14/908341
DATED : March 27, 2018
INVENTOR(S) : Benzhong Tang, Ni Xie and Wing Yip Lam It is certified that error appears in the above-identified patent and that said Letters Patent is hereby corrected as shown below:

On the Title Page

Item (60), "Related U.S. Application Data", please delete "Provisional application no. 61/958,746, filed on Aug. 5, 2013" and replace with "Provisional application no. 61/958,743, filed on Aug. 5, 2013".

Signed and Sealed this
Sixteenth Day of April, 2019

Andrei Iancu
*Director of the United States Patent and Trademark Office*